(12) United States Patent
Berardinelli

(10) Patent No.: US 10,175,654 B2
(45) Date of Patent: Jan. 8, 2019

(54) SMARTWATCH DEVICE AND METHOD

(71) Applicant: Raymond A. Berardinelli, Gallitzin, PA (US)

(72) Inventor: Raymond A. Berardinelli, Gallitzin, PA (US)

(*) Notice: Subject to any disclaimer, the term of this patent is extended or adjusted under 35 U.S.C. 154(b) by 0 days.

(21) Appl. No.: 15/947,038

(22) Filed: Apr. 6, 2018

(65) Prior Publication Data

US 2018/0224804 A1     Aug. 9, 2018

Related U.S. Application Data

(63) Continuation of application No. 15/487,493, filed on Apr. 14, 2017, now Pat. No. 9,939,784, and a
(Continued)

(51) Int. Cl.
| | |
|---|---|
| *H04W 4/02* | (2018.01) |
| *H04B 1/3827* | (2015.01) |
| *H04M 1/60* | (2006.01) |
| *G04B 47/06* | (2006.01) |
| *G06F 1/16* | (2006.01) |
| *G06F 21/35* | (2013.01) |
| *H04L 12/54* | (2013.01) |

(Continued)

(52) U.S. Cl.
CPC ....... *G04B 47/063* (2013.01); *G04B 37/1486* (2013.01); *G04G 9/0064* (2013.01); *G04G 21/08* (2013.01); *G06F 1/163* (2013.01); *G06F 21/35* (2013.01); *H04L 12/54* (2013.01); *H04M 1/7253* (2013.01); *H04W 4/027* (2013.01); *G06F 2200/1637* (2013.01); *G06K 9/00335* (2013.01); *H04M 2250/12* (2013.01); *H04W 4/80* (2018.02); *H04W 8/005* (2013.01); *H04W 76/14* (2018.02)

(58) Field of Classification Search
CPC ..... H04B 5/0043; H04B 1/385; H04W 8/005; H04W 4/008; H04W 76/023; H04W 4/025; H04M 1/7253; H04M 2250/12; H04M 1/6058; H04M 1/05; G04G 9/0064; G04F 21/08; G04B 7/063; G04B 37/1486

See application file for complete search history.

(56) References Cited

U.S. PATENT DOCUMENTS

| | | | |
|---|---|---|---|
| 9,272,186 B2* | 3/2016 | Reich ................. | A63B 24/0062 |
| 9,939,784 B1* | 4/2018 | Berardinelli ........... | G06F 1/163 |

(Continued)

*Primary Examiner* — Andrew Wendell
(74) *Attorney, Agent, or Firm* — Nils H. Ljungman & Associates

(57) ABSTRACT

A smartwatch device and method. The abstract of the disclosure is submitted herewith as required by 37 C.F.R. § 1.72(b). As stated in 37 C.F.R. § 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

16 Claims, 42 Drawing Sheets

Related U.S. Application Data continuation-in-part of application No. PCT/US2016/055752, filed on Oct. 6, 2016.

(60) Provisional application No. 62/341,864, filed on May 26, 2016, provisional application No. 62/338,658, filed on May 19, 2016, provisional application No. 62/317,958, filed on Apr. 4, 2016, provisional application No. 62/237,664, filed on Oct. 6, 2015.

(51) Int. Cl.
| | |
|---|---|
| *H04M 1/725* | (2006.01) |
| *G04B 37/14* | (2006.01) |
| *G04G 9/00* | (2006.01) |
| *G04G 21/08* | (2010.01) |
| *G06K 9/00* | (2006.01) |
| *H04W 4/80* | (2018.01) |
| *H04W 76/14* | (2018.01) |
| *H04W 8/00* | (2009.01) |

(56) References Cited

U.S. PATENT DOCUMENTS

| | | | |
|---|---|---|---|
| 2014/0104419 A1* | 4/2014 | Metzler | G01C 15/002 348/140 |
| 2014/0187990 A1* | 7/2014 | Banet | A61B 5/6822 600/515 |
| 2016/0327915 A1* | 11/2016 | Katzer | G04B 19/04 |
| 2017/0026610 A1* | 1/2017 | Kwon | H04N 5/9202 |
| 2017/0201611 A1* | 7/2017 | Donley | H04M 1/7253 |
| 2017/0216668 A1* | 8/2017 | Burton | G04F 10/00 |

\* cited by examiner

FIG. 6
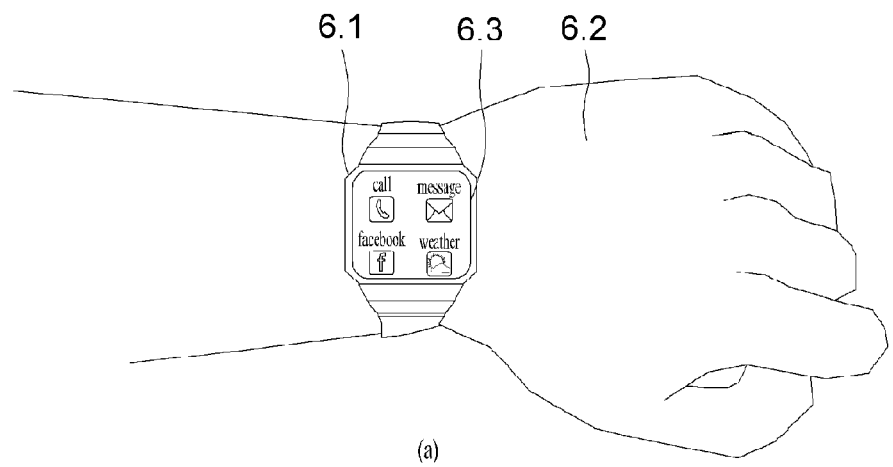
(a)
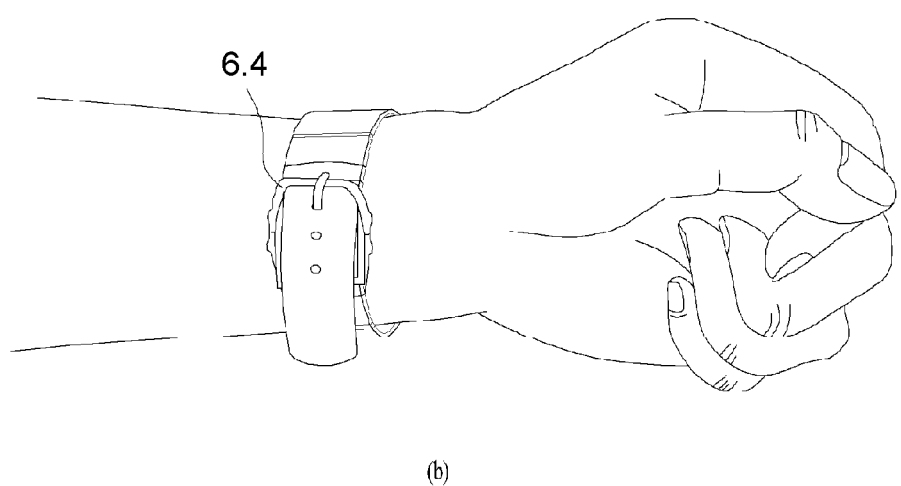
(b)

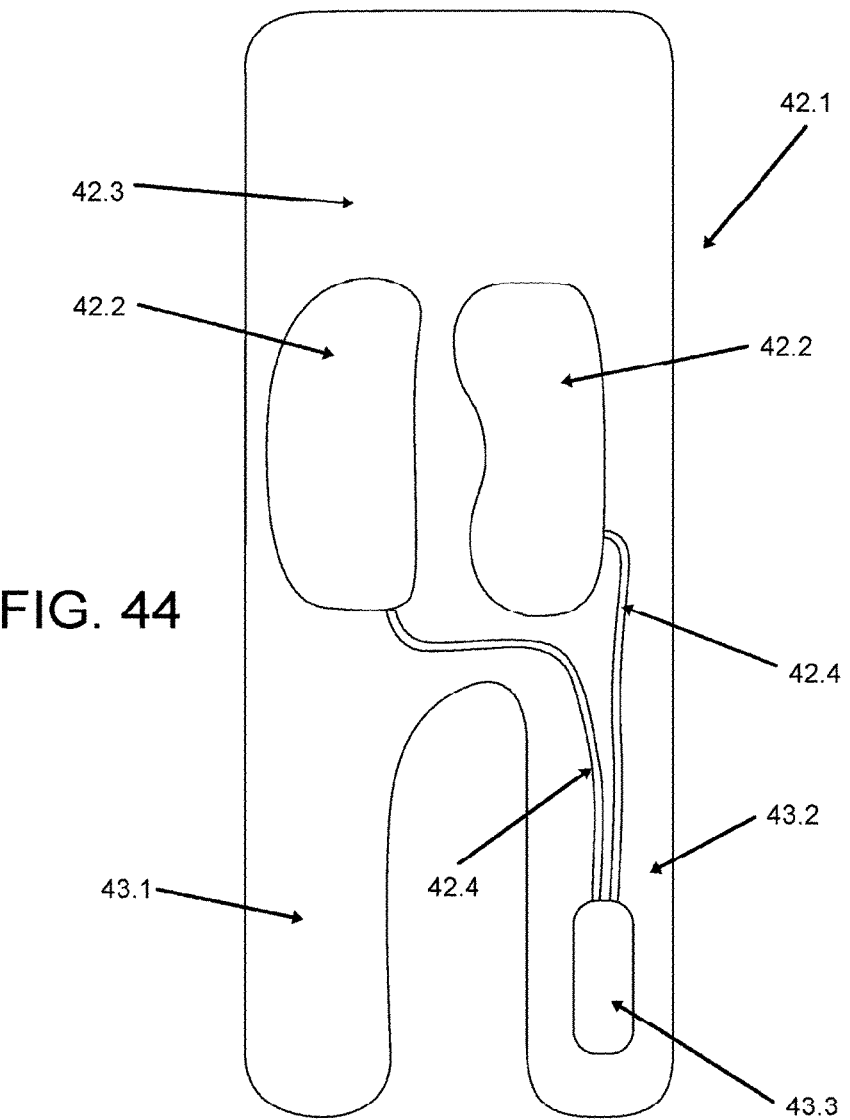

SMARTWATCH DEVICE AND METHOD

CONTINUING APPLICATION DATA

This application is a continuation of U.S. patent application Ser. No. 15/487,493, filed on Apr. 14, 2017. This application is also a Continuation-In-Part application of International Patent Application No. PCT/US2016/055752, filed on Oct. 6, 2016, which claims benefit of U.S. Provisional Patent Application No. 62/237,664, filed on Oct. 6, 2015, U.S. Provisional Patent Application No. 62/317,958, filed on Apr. 4, 2016, U.S. Provisional Patent Application No. 62/338,658, filed on May 19, 2016, and U.S. Provisional Patent Application No. 62/341,864, filed on May 26, 2016. International Patent Application No. PCT/US2016/055752 was pending as of the filing date of this application. The United States was an elected state in International Patent Application No. PCT/US2016/055752.

BACKGROUND

1. Technical Field

The present application relates to a smartwatch device and method.

2. Background Information

Background information is for informational purposes only and does not necessarily admit that subsequently mentioned information and publications are prior art.

A smartwatch is a computerized wristwatch with functionality that is enhanced beyond timekeeping. Some early models of smartwatches could only perform the most basic of tasks, such as mathematical calculations, translations from one language to another, and playing simple electronic games. In contrast, most modern smartwatches are effectively wearable computers. Many run mobile applications (apps) using a mobile operating system.

Some smartwatches function as portable media players. Such smartwatches can replace other media players, like CD players, DVD players, MP3 players, etc., by offering playback of FM radio, audio files, and video files to the user, either over a built-in speaker or via a connected listening device, such as headphones or a headset, which could be wired or wireless. Some smartwatches, also known as "watch phones," are designed to replace a mobile or cellular telephone. These models have full mobile phone capability, and can be used to make or answer phone calls.

Smartwatches can be designed with a substantial variety of internal hardware components. Most have a rechargeable battery and graphical display. Many include a touch screen or similar interface. Peripheral devices may possibly include, but are not limited to, such devices as a camera, thermometer, accelerometer, altimeter, barometer, compass, global positioning system (GPS) receiver, audio speaker, and digital memory card that is recognized as a mass storage device by a computer. In addition to hardware, the smartwatch can include a variety of software to perform different tasks and functions, such as, but not limited to, displaying a map, a personal scheduler or calendar, a calculator, and various kinds of watch faces and displays. The smartwatch may also be designed to communicate with a number of different external devices, such as, but not limited to, different types of sensors, a wireless headset, a heads-up display, a computer, or a server.

It should be understood that smartwatches are part of the general category of wearable devices. Any discussion herein relating to smartwatches also should be considered as including other wearable devices that may be worn on parts of the body aside from the wrist or arm, as is common with smartwatches. For example, some wearable devices may comprise bands or straps to allow wearing on the head, torso, or legs in addition to arms. Other wearable devices are articles of clothing, such as shirts, vests, pants, glasses, gloves, and jackets, with technological components built in to the clothing. These wearable devices could have similar components and functions as a smartwatch disclosed herein.

Like other computers, a smartwatch may be used to collect information from internal or external sensors. A smartwatch may also be used to control other instruments or computers, or retrieve data from them. The smartwatch may support wireless technologies like Wi-Fi®, Bluetooth®, and GPS. For many purposes, a "wristwatch computer" simply serves as a front end for a remote system, communicating by various radio technologies.

Many current smartwatch models are completely functional as standalone products. Some serve as sport watches, with the GPS tracking unit being used to record exercise data, such as travel time, distance, and location. For example, after a workout, data can be uploaded onto a computer or online to create a log of activities for analysis or sharing. Some smartwatches can serve as full GPS watches, displaying maps and current coordinates, and recording tracks. Users can "mark" their current location and then edit the entry's name and coordinates, which enables navigation to those new coordinates.

Some smartwatches function as "sport watches," which often include activity tracker or fitness tracker features as seen in GPS watches made for outdoor sports. Functions may include training programs, stopwatch, speed display, GPS tracking unit, route tracking, dive computer, heart rate monitor compatibility, and cadence sensor compatibility. Smartwatches also walk through tutorials/videos on the watch face.

Other smartwatches can cooperate with an app in a smartphone to carry out their functions. These smartwatches may be little more than timepieces unless they are paired, usually wirelessly, with a mobile phone. Some of these smartwatches only work with a phone that runs the same mobile operating system, whereas others use an operating system unique to the smartwatch, or otherwise are able to work with most smartphones. When paired, a smartwatch may function as a remote access point for the phone, which generally allows the smartwatch to display data such as calls, SMS messages, e-mails, and calendar invites, and any data that may be made available by relevant phone apps.

Current smartwatches and electronic fitness tracker designs often incorporate wireless technology (such as Wi-Fi® and Bluetooth®) or have heart-rate and oxygen saturation and blood pressure monitoring capabilities. Smartwatches and fitness trackers can be designed to allow users to track complex motions requiring the use of motion sensors such as gyroscopes, accelerometers, compasses, and pressure sensors, fusing the sensor outputs into a single and accurate data stream for use as input commands in consumer electronics devices, and ongoing run-time calibration to ensure an optimal user experience.

OBJECT OR OBJECTS

An object of the present application may be to provide a smartwatch device and method.

SUMMARY

Smartwatches, as discussed above, can be used in different areas or industries to perform different functions usually performed by computers, electronic devices, or other devices. Such smartwatches can handle, store, and communicate data, much like a computer. Other smartwatches incorporate detection and measurement devices, such as motion sensors, monitors, gyroscopes, accelerometers, compasses, pressure sensors, and GPS and tracking devices. The present application describes smartwatch devices and methods of using smartwatch devices.

BRIEF DESCRIPTION OF THE DRAWINGS

FIG. 6 is a view showing a smart watch according to one exemplification of the disclosure;

FIGS. 42, 43, and 44 show an exemplification of a glove device.

DESCRIPTION OF EXEMPLIFICATION OR EXEMPLIFICATIONS

Figure 1:
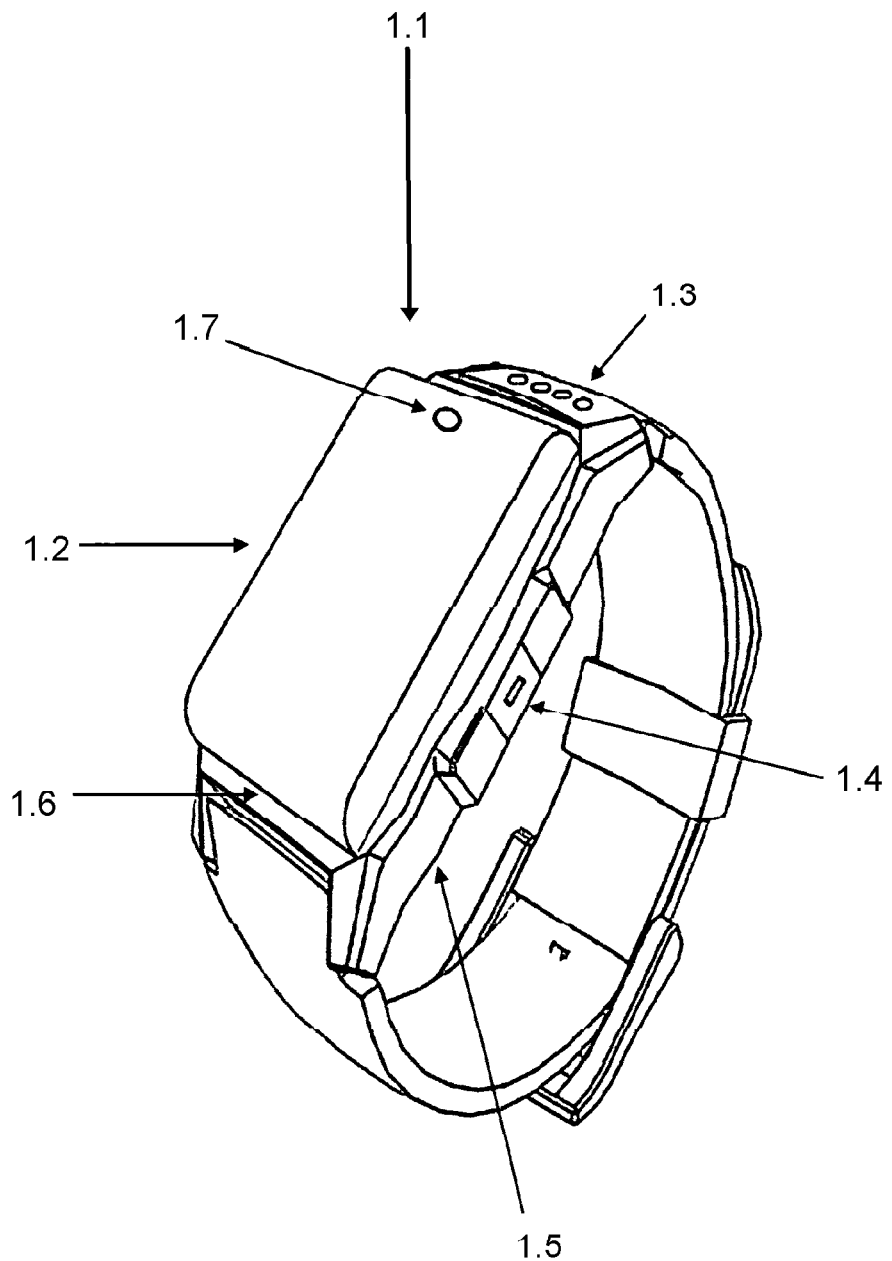
FIG. 1 shows an exemplification of a smartwatch.

Referring now to the present application in more detail, in FIG. 1 there is shown a smartwatch device 1.1, which utilizes a touch screen graphical user interface 1.2. The smartwatch device 1.1 utilizes both an internal rechargeable battery, as well as an external battery charging connecting points 1.3. An external charge can also be fed to the smartwatch device by way of the wired data transfer connection in the form of the MicroUSB connector 1.4. The smartwatch device 1.1 maintains multiple sub-systems including accelerometer, GPS system, GMS chip slot, Micro SD memory slot, processing unit, WiFi, Bluetooth and cellular transmitter/receiver inside the primary casing 1.5. A water resistant sealed casing 1.6 is shown and front-facing camera 1.7.

Figure 2:
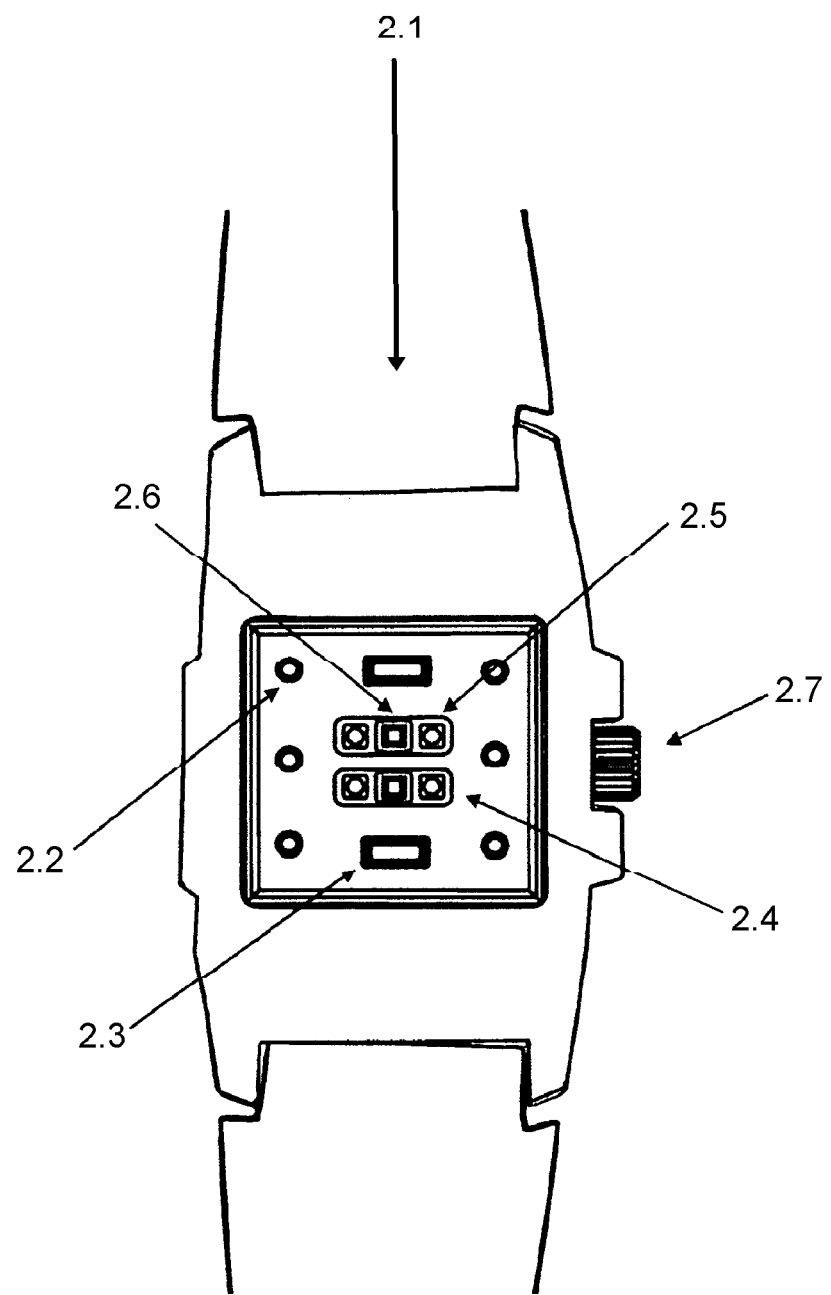
FIG. 2 shows an exemplification of a smartwatch.

The smartwatch device 2.1 of FIG. 2 includes tracking sensor systems, such as but not limited to both temperature sensors 2.2, pulse sensors 2.3, other sensors 2.4, a series of reflective light emitting diodes (LED) 2.5, including but not limited to 660 nanometer and 940 nanometer wavelengths, and receiving units 2.6. The smartwatch device 2.1 also includes a side facing camera and lighting source 2.7.

Figure 3:
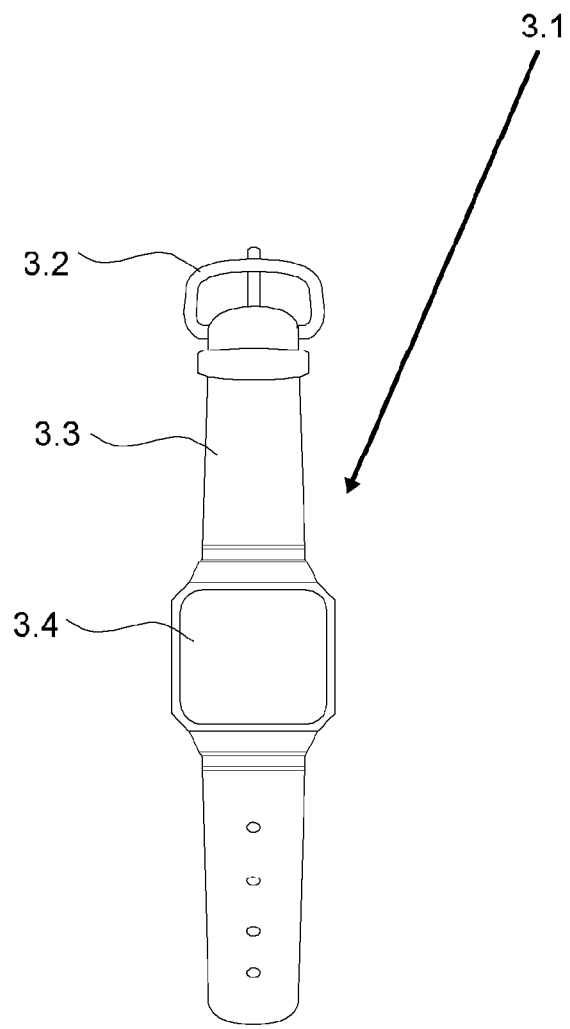
FIG. 3 is a rear view of a smart watch, according to an exemplification of the disclosure.

As shown in FIG. 3, according to the disclosure, a smart watch 3.1 may detect whether the smart watch 3.1 is worn using a wearing sensor unit. For example, the smart watch 3.1 may detect whether the smart watch 3.1 is worn using a proximity sensor. Alternatively, the smart watch 3.1 may detect whether the smart watch 3.1 is worn using a sensor included in a buckle 3.2 of the smart watch 3.1. If the smart watch 3.1 is buckled, the smart watch 3.1 may determine that the smart watch 3.1 is worn by a user. Alternatively, the smart watch 3.1 may detect whether the smart watch 3.1 is worn using a touch sensor included in a rear surface of a main body 3.4 or a band 3.3 of the smart watch 3.1. If the smart watch 3.1 senses touch of the user on the rear surface of the main body 3.4 or the band 3.3, the smart watch 3.1 may determine that the smart watch 3.1 is worn by the user. That is, the smart watch 3.1 may determine whether the smart watch 3.1 is worn by the user using the above-described sensors. In the disclosure, at least one of the above sensors for providing sensing results to be referred for determination is referred to as the wearing sensor unit.

According to the disclosure, the smart watch 3.1 may detect movement of the smart watch 3.1 using a movement sensor unit. For example, the smart watch 3.1 may detect movement of the smart watch 3.1 using a proximity sensor. Alternatively, the smart watch 3.1 may detect movement of the smart watch 3.1 using a touch sensor included in a rear surface of the main body 3.4 or the band 3.3. In addition, the smart watch 3.1 may include at least one of a gyro sensor, an acceleration sensor, and a gravity sensor. As such, the smart watch 3.1 may detect movement by detecting the position of the smart watch 3.1 on an arm of the user.

According to one possible exemplification, the smart watch 3.1 may detect movement by detecting a position where the smart watch 3.1 is worn and then measuring a time when a signal varies as the smart watch 3.1 moves. Alternatively, the smart watch 3.1 may detect movement of the smart watch 3.1 based on variation in coordinates of the smart watch 3.1 detected on the arm. That is, the smart watch 3.1 may detect movement of the smart watch 3.1 on the arm using the above-described sensors. In the disclosure, at least one of the above sensors for providing sensing results to be referred for determination is referred to as the movement sensor unit.

The above-described sensors included in the smart watch 3.1 may be formed as separate elements or at least one integrated element. According to an exemplification, the wearing sensor unit and the movement sensor unit may be an integrated sensor unit. The integrated sensor unit may simultaneously or substantially simultaneously detect whether the smart watch 3.1 is worn and movement of the smart watch 3.1, and may transmit a signal regarding the detected results to the processor.

The display unit may display visual information. In this case, the visual information may include at least one of a still image, a moving image, and text and may refer to information visually recognizable by the user. In addition, the visual information may be a result of execution of various types of digital content by the smart watch 3.1.

According to the disclosure, the display unit may display information regarding a function performed by the processor or feedback information regarding the performed function as the visual information.

The processor may perform a function based on signals received from the wearing sensor unit and the movement sensor unit. When the smart watch 3.1 is worn by the user, the processor may detect movement of the smart watch 3.1 on the arm to obtain the direction and distance of movement. In addition, the processor may perform a function by determining whether the obtained direction and distance of movement of the smart watch 3.1 correspond to a predetermined direction and distance of movement.

Here, the performed function may include a function related to capture of a screen image and storing of the captured image, a function related to control of an external device, a function related to payment, a function related to link connection to or link disconnection from a portable device, a function related to execution of a search mode, a function related to bookmarking, a function related to display of visual information, a function related to switching on or off of a setup value, a function related to returning to a previous operation, a function related to separation of user interface structures, and a function related to reception of a call signal. However, functions performed by the smart watch 3.1 are not limited to the above-listed functions.

In addition, the processor may determine whether to operate each unit of the smart watch 3.1. The processor may set an on or off state of each unit. According to one possible exemplification, in order to prevent, restrict, and/or minimize the smart watch 3.1 from performing unintended functions, the processor may set the wearing sensor unit or the movement sensor unit not to detect input. As such, the smart watch 3.1 may perform a function only as desired by the user. The elements may be mounted in the form of one integrated chip or a plurality of separate chips based on design of the smart watch 3.1.

The smart watch 3.1 may include a rotation sensor unit for detecting rotation of the smart watch 3.1 about a rotation axis thereof. The smart watch 3.1 may also include a front-surface touch sensor unit for sensing additional touch on a front surface of the main body 3.4 or the band 3.3. The smart watch 3.1 may further include a tightness sensor unit for detecting how tightly the band 3.3 is fastened. In addition, the smart watch 3.1 may include a storage unit for storing digital data. The rotation sensor unit may include at least one of a gyro sensor, an acceleration sensor, and a gravity sensor. The rotation sensor unit may detect rotation of the smart watch 3.1 about a rotation axis thereof. In this case, the smart watch 3.1 may obtain the direction and distance of rotation. The processor may perform a function by determining whether the direction and distance of rotation correspond to a predetermined direction and distance of rotation.

The front-surface touch sensor unit may be formed in the front surface of the main body 3.4 or the band 3.3 of the smart watch 3.1. The front-surface touch sensor unit may detect an additional input signal. In this case, the additional input signal may be different from an input signal sensed by the wearing sensor unit and the movement sensor unit. The front-surface touch sensor unit may detect additional touch input of the user on the front surface of the main body 3.4 or the band 3.3.

The storage unit may store a variety of digital data such as video, audio, image, and application. According to the disclosure, the processor may store an image captured by performing a function, or history information regarding performed functions, in the storage unit. According to one possible exemplification, the smart watch 3.1 may store programs used for control by the processor, or may temporarily store input/output data. The storage unit may include a variety of digital data storage devices such as flash memory, random access memory (RAM), and a solid state drive (SSD). The tightness sensor unit may detect how tightly the band 3.3 of the smart watch 3.1 is fastened. Here, the tightness sensor unit may include at least one of a pressure sensor, a proximity sensor, and an infrared sensor. In this case, the processor may adjust a threshold distance corresponding to a reference value regarding the distance of movement of the smart watch 3.1, based on the detected tightness. The above-described sensors included in the smart watch 3.1 may be formed as separate elements or at least one integrated element.

Figure 4:
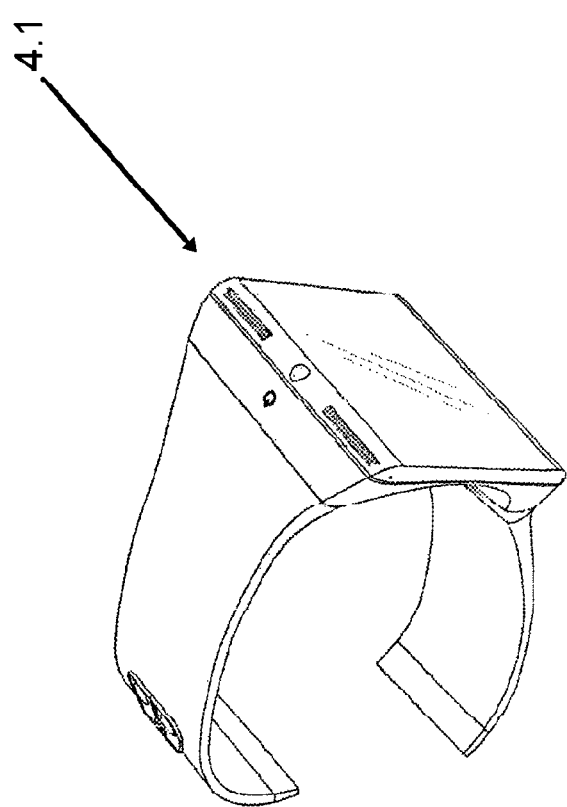
FIG. 4 shows a perspective view of a smartwatch according to at least one possible exemplification.
Figure 5:
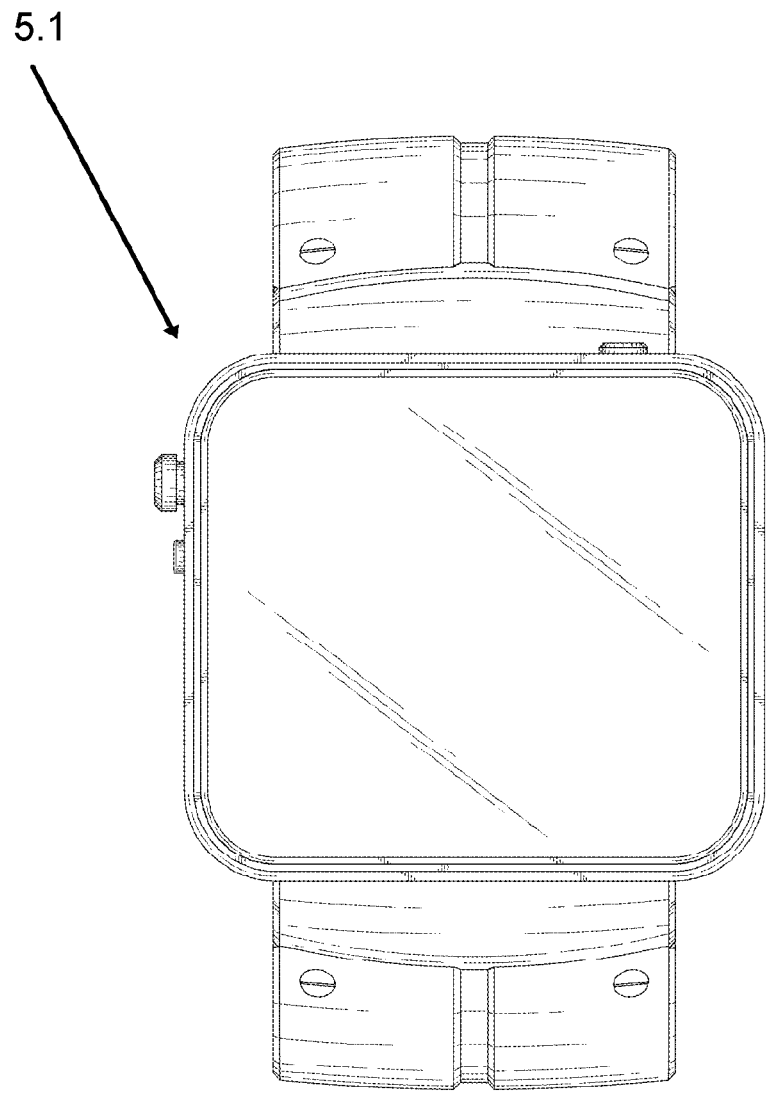
FIG. 5 shows a front view of a smartwatch according to at least one possible exemplification.

FIG. 4 shows a perspective view of a smartwatch 4.1 according to at least one possible exemplification of the present application. FIG. 5 shows a front view of a smartwatch 5.1 according to at least one possible exemplification of the present application. FIG. 6 is a view showing the smart watch according to one exemplification of the disclosure. FIG. 6 shows a state in which the smart watch 3.1 is worn by the user designated by reference numeral 6.2. In other words, FIG. 6 shows a worn mode.

As shown by (a), the face 6.3 of the smart watch 6.1, disposed on the wrist of a user 6.2, is pointing toward the view of the user 6.2, such that the buckle (not shown) is pointing away from the view of the user 6.2. As shown by (b), the buckle 6.4 of the smart watch 6.1, disposed on the wrist of a user 6.2, is pointing toward the view of the user 6.2, such that the face 6.3 (not shown) is pointing away from the view of the user 6.2. By the user 6.2 rotating his or her wrist, the user 6.2 can rotate the view of the smartwatch 6.1. The smartwatch 6.1 can be configured with sensors to determine such rotation and/or movement, which can be used to control the programming of the smartwatch 6.1 or to input into a program of the smartwatch 6.1.

Figure 7:
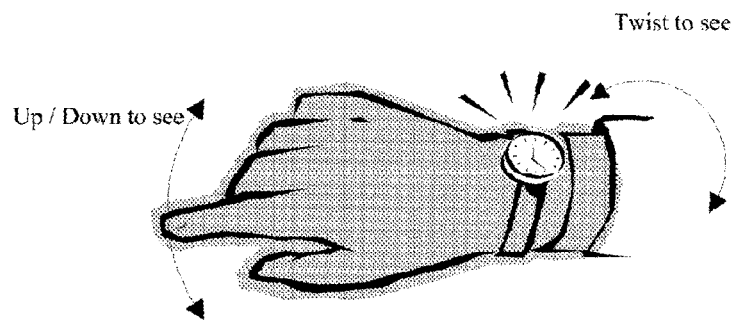
FIG. 7 illustrates a schematic diagram of an exemplary gesture to be detected.

FIG. 7 illustrates a schematic diagram of an exemplary gesture to be detected consistent with the disclosed exemplifications. The gesture to be detected is defined as two initial movements and a stop motion to take a look for information (i.e., a lookup gesture). The two initial movements include moving up-down to take a smart wearable device in front of a user's eyes and twisting the smart wearable device to bring a display screen (e.g., a touch screen) of the smart wearable device in front of the user's eyes.

When the smart wearable device is a smartwatch, if the lookup gesture (a sequence of movements) is detected, it may indicate that a user of the smartwatch wants to see information displayed on the display screen of the smartwatch. Therefore, the display screen of the smartwatch is turned on to show the information. While the second motion (i.e., a stop motion) is being detected, the user does not intend to see the display screen if the user keeps the up-down and/or twist motion. In addition to this scenario, an angle of the display screen may be detected because the user may not watch the display screen when the display screen points to certain angles.

Figure 8:
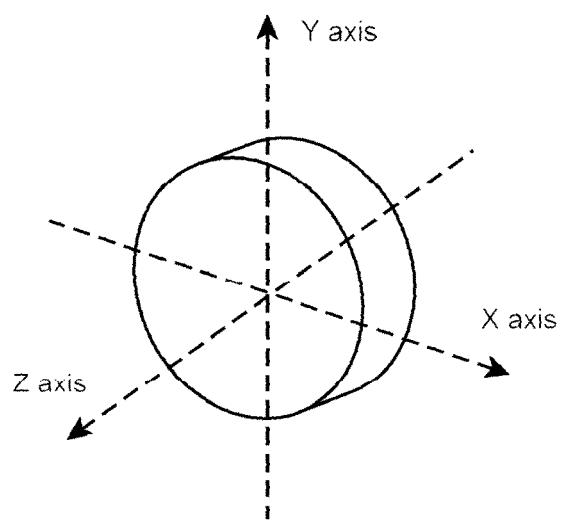
FIG. 8 shows three axes of a smart wearable device consistent with the disclosed exemplifications.

FIG. 8 shows three axes of a smart wearable device consistent with the disclosed exemplifications. As shown in FIG. 8, a three-dimensional (3D) coordinate system on a smart wearable device (e.g., a smartwatch) is established, where an X axis (i.e., horizontal axis) direction is from left to right horizontally; a Y axis (i.e., vertical axis) direction is from bottom to top vertically; and a Z axis direction is from back to front and perpendicular to a display screen of the smart wearable device. If the Z axis of the smart wearable device shares the direction of the display screen as shown in FIG. 8, a stop motion is detected by tracking the direction of the Z axis. That is, the direction of the display screen (i.e., the center of the Z axis) is not out of range to be aligned to the user's eyes for a predefined waiting period, the stop motion is detected.

A mapping relationship between a set of pre-defined gestures and a set of power management functions needs to be established. The set of pre-defined gestures may include at least one lookup gesture. Other swipe gestures (e.g., a swipe gesture) may also be included in the set of pre-defined gestures. The set of power management functions may include at least one function for turning on the display screen of the wearable device. Other power management functions (e.g., adjusting screen brightness) may also be included in the set of power management functions. In one application scenario, a user views time and/or his/her health index (e.g., heart rate) by using a smartwatch on his/her wrist. The power for the display screen of the smartwatch may be controlled by detecting the lookup gesture which indicates that the user wants to check information on the display screen. That is, a mapping relationship between the lookup gesture and the function for turning on the display screen of the wearable device is established.

Figure 9:
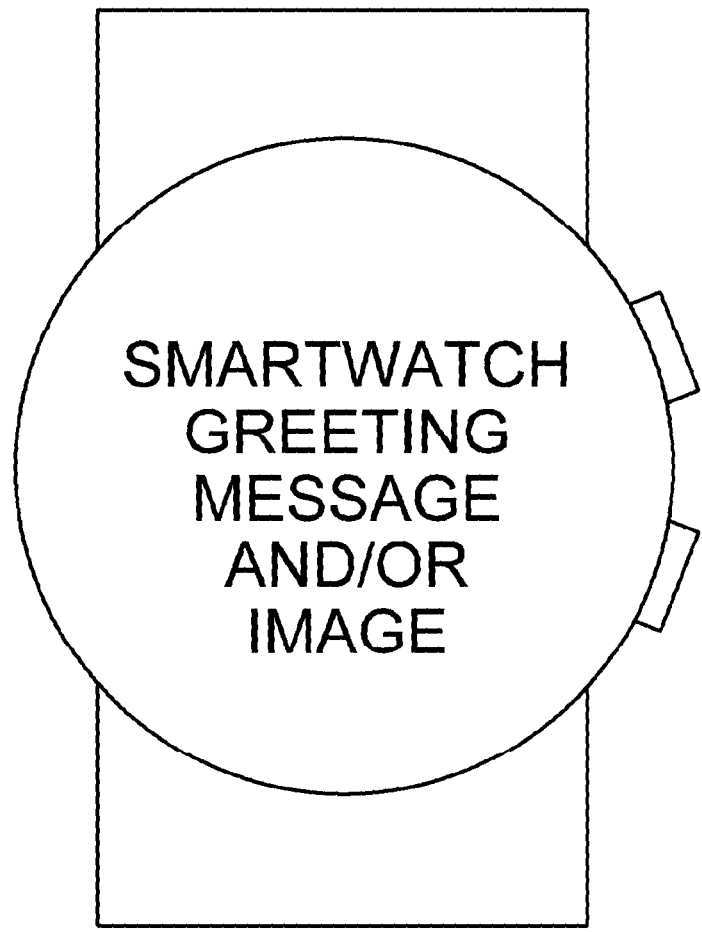
FIG. 9 shows a smartwatch with a display according to a possible exemplification.
Figure 10:
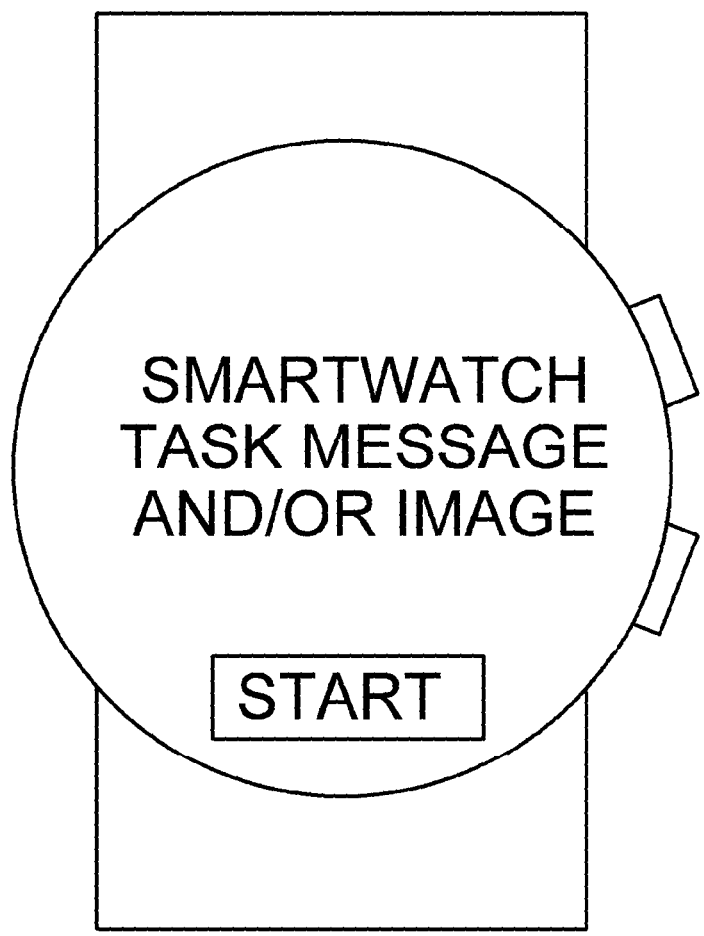
FIG. 10 shows a smartwatch with a display according to a possible exemplification.
Figure 11:
FIG. 11 shows a smartwatch with a display according to a possible exemplification.
Figure 12:
FIG. 12 shows a smartwatch with a display according to a possible exemplification.
Figure 13:
FIG. 13 shows a smartwatch with a display according to a possible exemplification.
Figure 14:
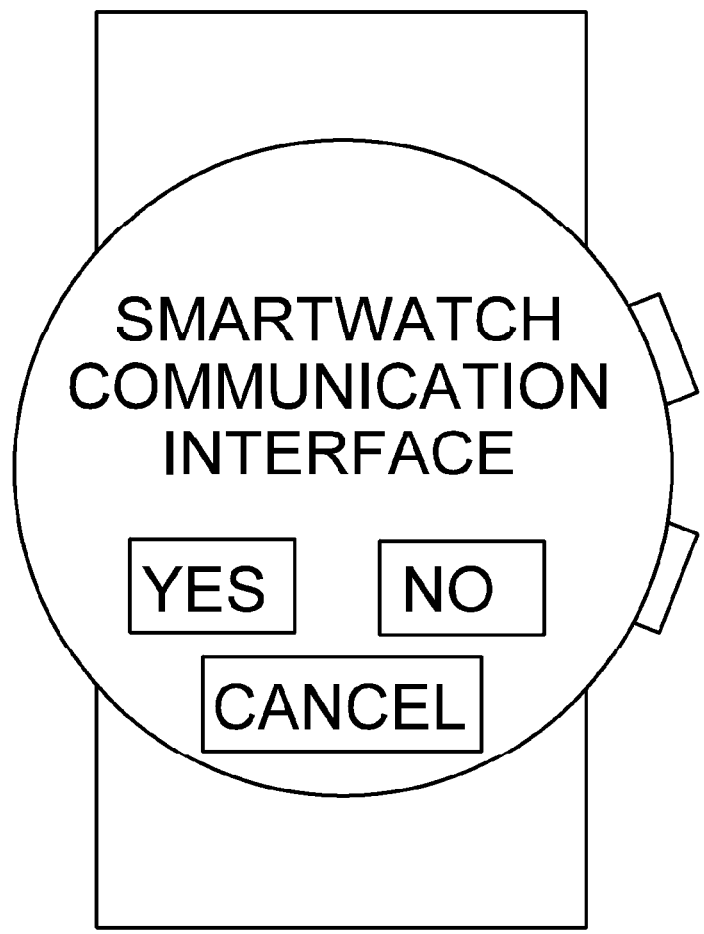
FIG. 14 shows a smartwatch with a display according to a possible exemplification.

Smartwatches can be used for communication and delivery of information to a user. In an exemplification according to FIG. 9, the smartwatch can initially display a welcome or greeting message or image. Such an initial screen could display several different types of general information, such as information about the smartwatch, the user, or the provider of the smartwatch. As seen in FIG. 10, the smartwatch can provide a smartwatch task message to the user. The user can press a button on the display, such as a "start" or "begin" to start the task. As seen in FIG. 11, a smartwatch task adjustment message can also be displayed. The user can use this feature to choose an adjustment to the task by using the plus or minus buttons for an increase or decrease. In other exemplifications, other adjustments could be made available. If the user is unsure about an adjustment, a help button could be included, which is represented by the question mark symbol. As seen in FIG. 12, a smartwatch task message or image could be accessed or provided to the user, such as a question regarding the task or other function, to which the user could answer yes or no. As seen in FIG. 13, the smartwatch could also include a smartwatch task timer to countdown or record the length of time of a task. As seen in FIG. 14, the smartwatch could also have a communication interface to allow the user to communicate with another person, who is using another smartwatch, a mobile device, a smart phone, a tablet, a mobile phone, a computer, or a computer server portal.

Figure 15:
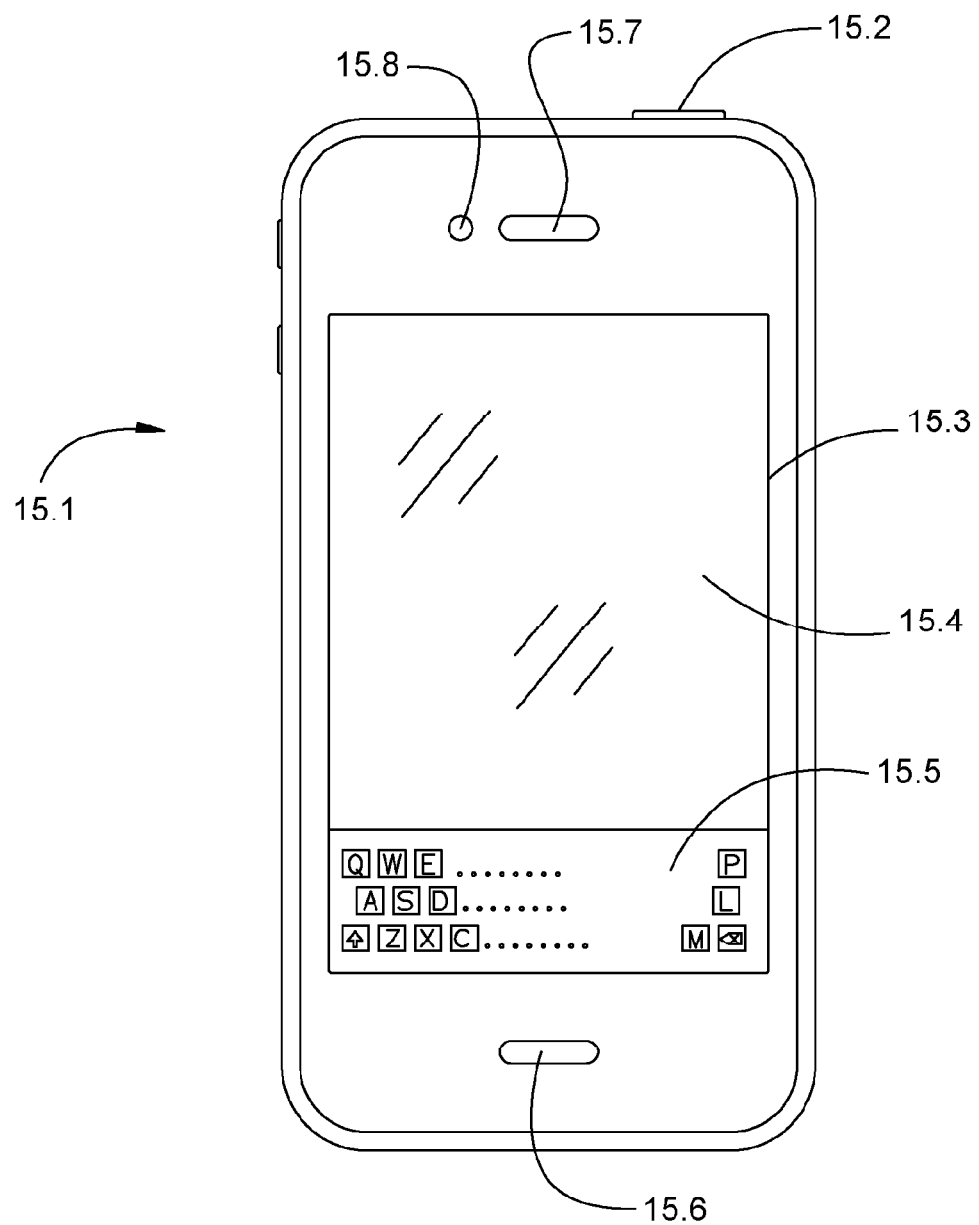
FIG. 15 is a schematic depiction of an exemplary electronic device.

FIG. 15 is a schematic depiction of an exemplary electronic device 15.1 for carrying out aspects of the present disclosure, in this instance, social media communications with similar devices, as discussed in greater detail below. It will be appreciated by those skilled in the art that the electronic device 15.1 shown and described herein is illustrative, and that variations on electronic device 15.1 can include, without limitation, a cellular telephone, tablet or like network access device.

Referring to FIG. 15, electronic device 15.1 comprises a housing 15.2 that supports a display 15.3. Display 15.3 can comprise one or more light emitters such as an array of light emitting diodes (LED), liquid crystals, plasma cells, or organic light emitting diodes (OLED) or the like. A touch-sensitive membrane 15.4 is overlaid on display 15.3 and configured to function as an input device for electronic device 15.1. As a non-limiting example, electronic device 15.1 can be configured to selectively show or hide a virtual keyboard 15.5. Other types of input devices, other than touch membrane 15.4, or in addition to touch membrane 15.4, are contemplated. For example, a physical keyboard, touch-pad, joystick or trackball or track-wheel may be employed to enable inputs to be made to electronic device 15.1. The electronic device 15.1 further comprises a microphone 15.6, speaker 15.7 and camera 15.8 (although one camera is shown in the drawings, the electronic device may comprise a plurality of cameras, including front and rear facing cameras, as known in the art).

Figure 16:
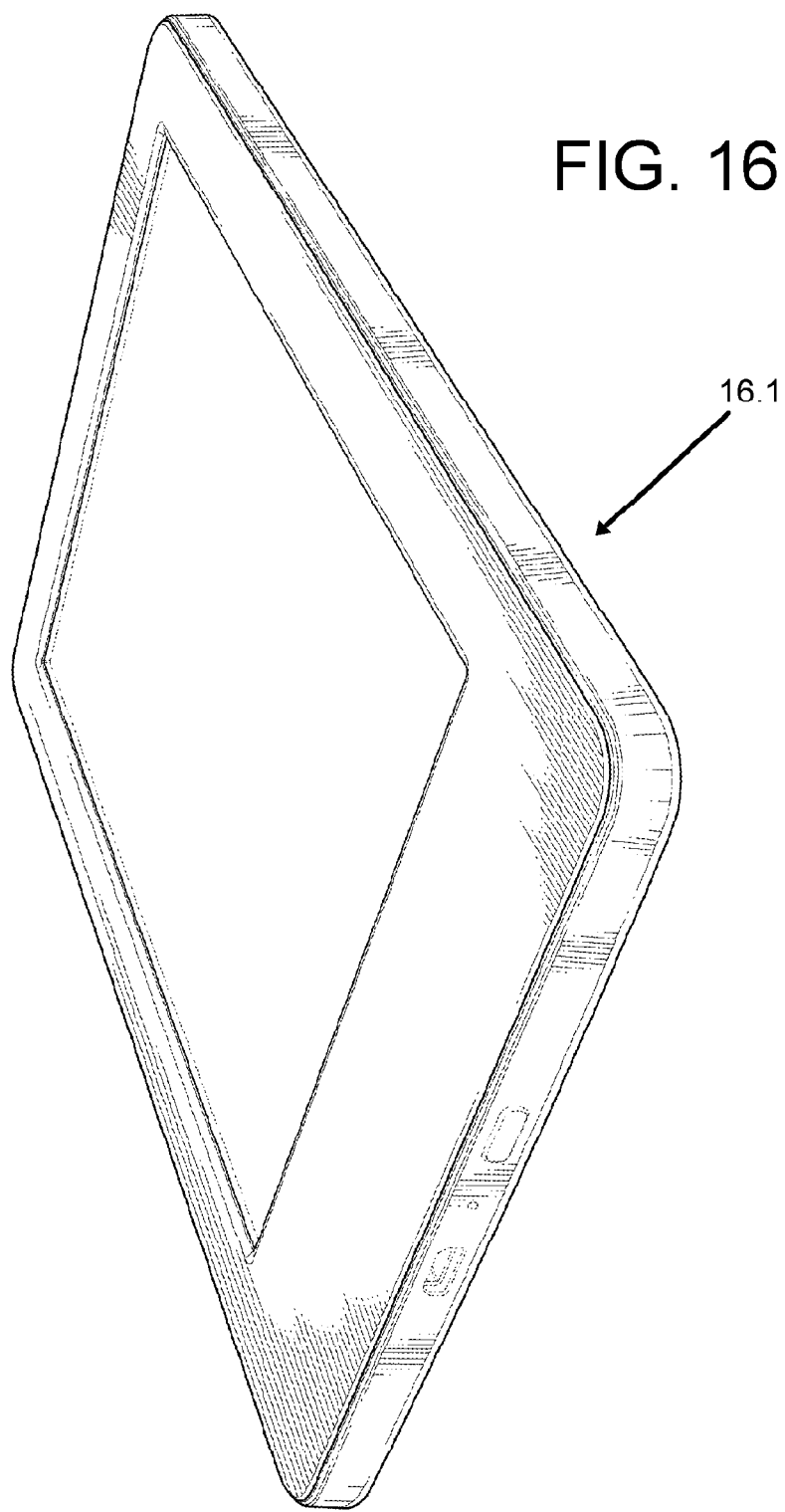
FIG. 16 is a front perspective view of a tablet computing device.
Figure 17:
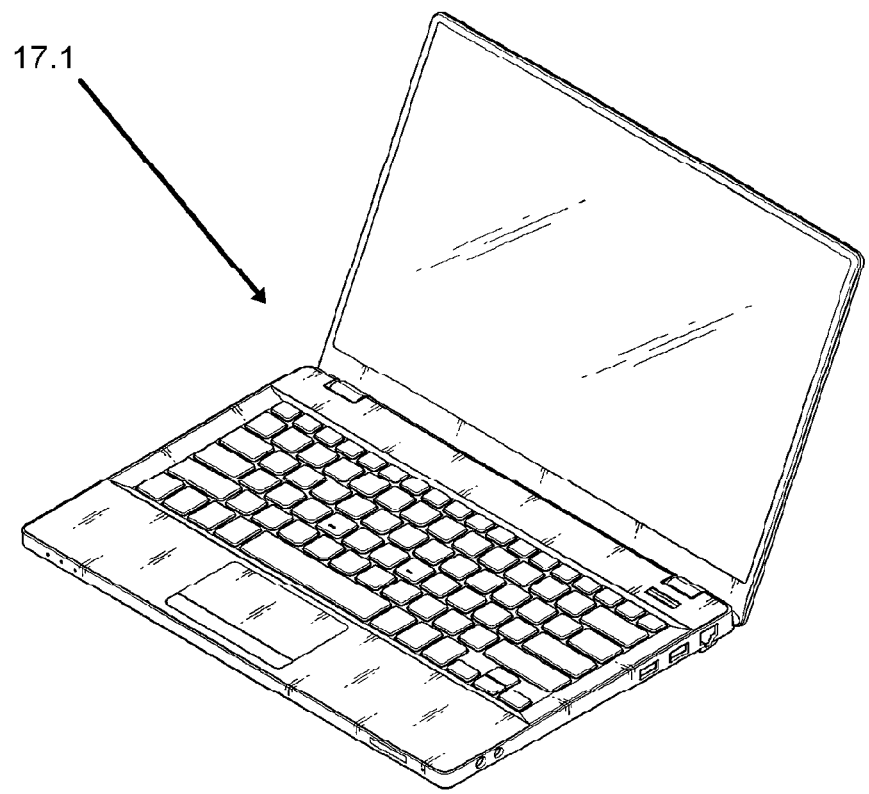
FIG. 17 is a front, right side, perspective view of a laptop computer.
Figure 18:
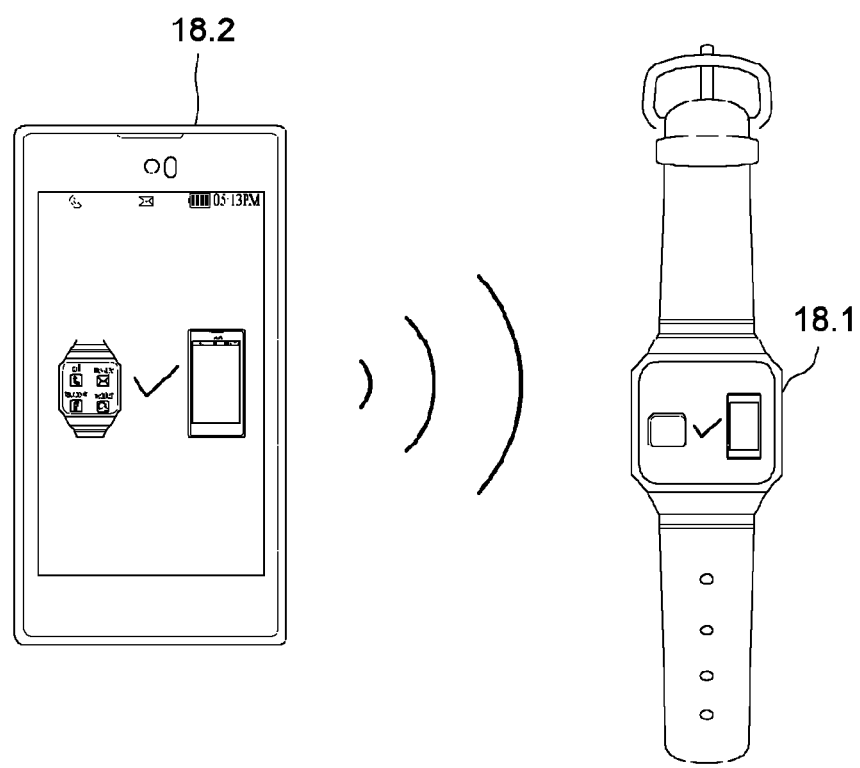
FIG. 18 is a view showing pairing between a smart watch and an external digital device.

FIG. 16 is a front perspective view of a tablet computing device 16.1, which may be utilized in the present application. FIG. 17 is a front, right side, perspective view of a laptop computer 17.1, which may be utilized in the present application. FIG. 18 is a view showing pairing between the smart watch and an external digital device according to one exemplification of the disclosure. FIG. 18 shows pairing of the smart watch 18.1 with the external digital device 18.2, such as a smart-phone. Here, the external digital device 18.2 may include a smart-phone, a laptop computer, or a Portable Multimedia Player (PMP), for example.

Pairing refers to connection for data transmission/reception between the smart watch 18.1 and the external digital device 18.2. When performing pairing, the smart watch 18.1 and the external digital device 18.2 may establish communication to realize bidirectional data transmission/reception. In the disclosure, pairing may be performed via Bluetooth, Near Field Communication (NFC), etc. In one example, pairing may be performed via a user input using the smart watch 18.1 or the external digital device 18.2. Here, the user input may include touch input, voice input, etc. For example, the smart watch 18.1 may provide a separate button or user interface for communication with the external digital device 18.2. In addition, the user may realize communication between the smart watch 18.1 and the external digital device 18.2 via user input using the button or the user interface. Once communication is established, the smart watch 18.1 may transmit or receive data to or from the external digital device 18.2 through an open session.

In the disclosure, the smart watch 18.1 may perform pairing with the external digital device 18.2 using the communication unit (not shown). In addition, through pairing, the smart watch 18.1 may receive a notification indicating at least one event that is scheduled to occur after detecting the take-off signal, from the external digital device 18.2. In addition, the smart watch 18.1 may provide the user with the notification received from the external digital device 18.2.

Although not shown in FIG. 18, when performing pairing with the external digital device 18.2, the smart watch 18.1 may display an indicator, representing pairing success, on the display unit. In addition, when released from pairing with the external digital device 18.2, the smart watch 18.1 may display an indicator, representing that pairing has been released, on the display unit.

Figure 19:
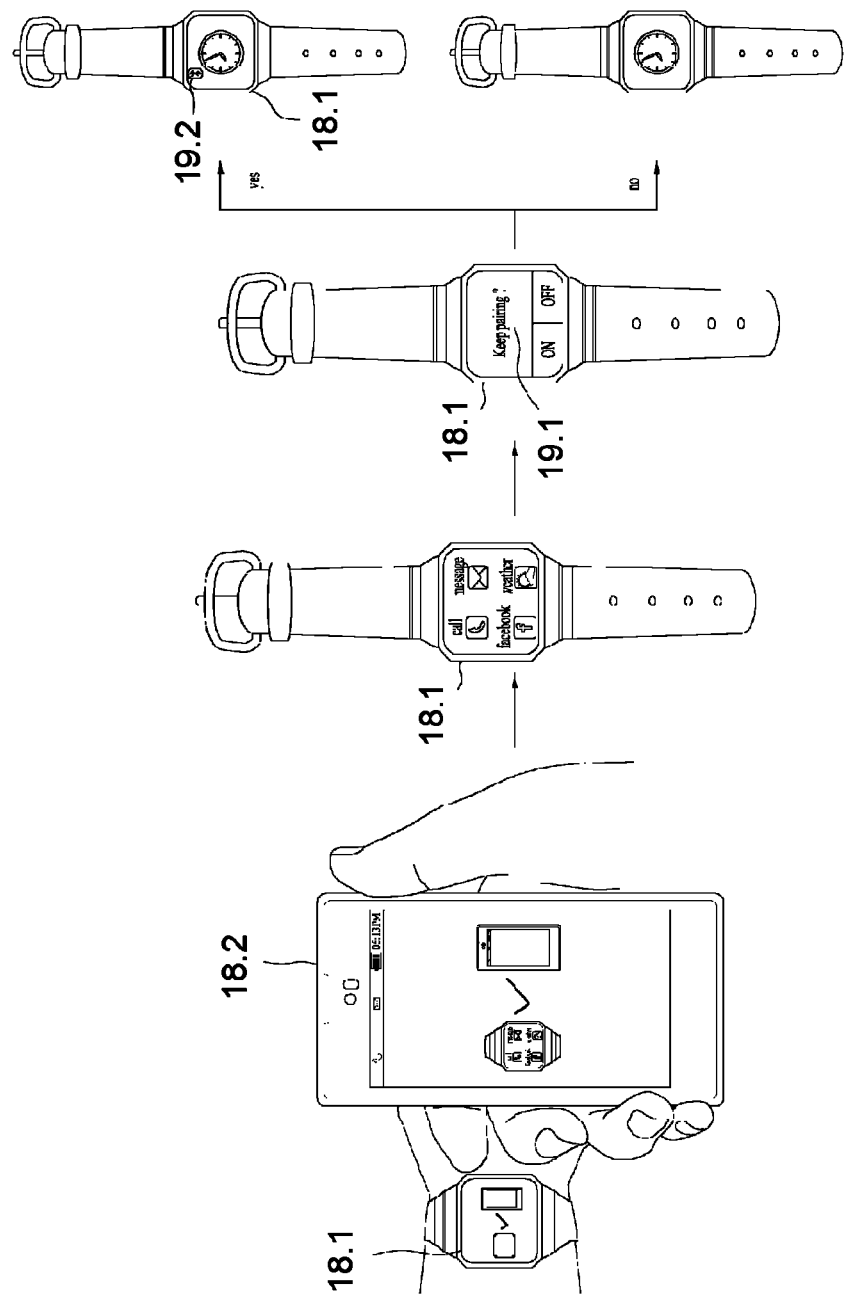
FIG. 19 is a view showing a second exemplification of a control method for a smart watch.

FIG. 19 is a view showing a second exemplification of a control method for the smart watch according to the disclosure. FIG. 19 shows whether or not to unpair between the smart watch 18.1 and the external digital device 18.2 if the smart watch 18.1 is switched from a worn mode to an unworn mode.

First, in a worn mode of the smart watch 18.1, the smart watch 18.1 may perform pairing with the external digital device 18.2. As described above with reference to FIG. 18, once pairing is completed, the smart watch 18.1 may transmit or receive data via communication with the external digital device 18.2. Next, the smart watch 18.1 may detect a take-off signal. Next, the smart watch 18.1 may be switched to an unworn mode in response to the detected take-off signal. In this case, the smart watch 18.1 may display a pairing interface 19.1 on the display unit. The pairing interface 19.1 is used to set whether or not to unpair between the smart watch 18.1 and the external digital device 18.2. In one exemplification, when detecting an input signal with regard to the unpairing, the smart watch 18.1 may unpair with the external digital device 18.2. Here, the smart watch 18.1 may display an indicator that represents the unpairing on the display unit. In another exemplification, when detecting an input signal with regard to the maintenance of pairing, the smart watch 18.1 may remain paired with the external digital device 18.2. Here, the smart watch 18.1 may display an indicator 19.2 representing that pairing is maintained, on the display unit. For example, referring to FIG. 19, the smart watch 18.1 may display the indicator 19.2, representing that Bluetooth communication is continued, on the display unit.

Meanwhile, upon detecting a take-off signal, the smart watch 18.1 may unpair with the external digital device 18.2, rather than displaying the pairing interface 19.1 on the display unit, according to automatic setting. In addition, upon detecting a take-off signal, the smart watch 18.1 may remain paired with the external digital device 18.2, rather than displaying the pairing interface 19.1 on the display unit, according to automatic setting. Here, the setting may include setting by user input, or automatic setting with regard to the smart watch 18.1, for example. Through the exemplifications described above, the smart watch 18.1 may set or unpair according to whether or not the smart watch 18.1 is in use, which may reduce consumption of battery power.

Figure 20:
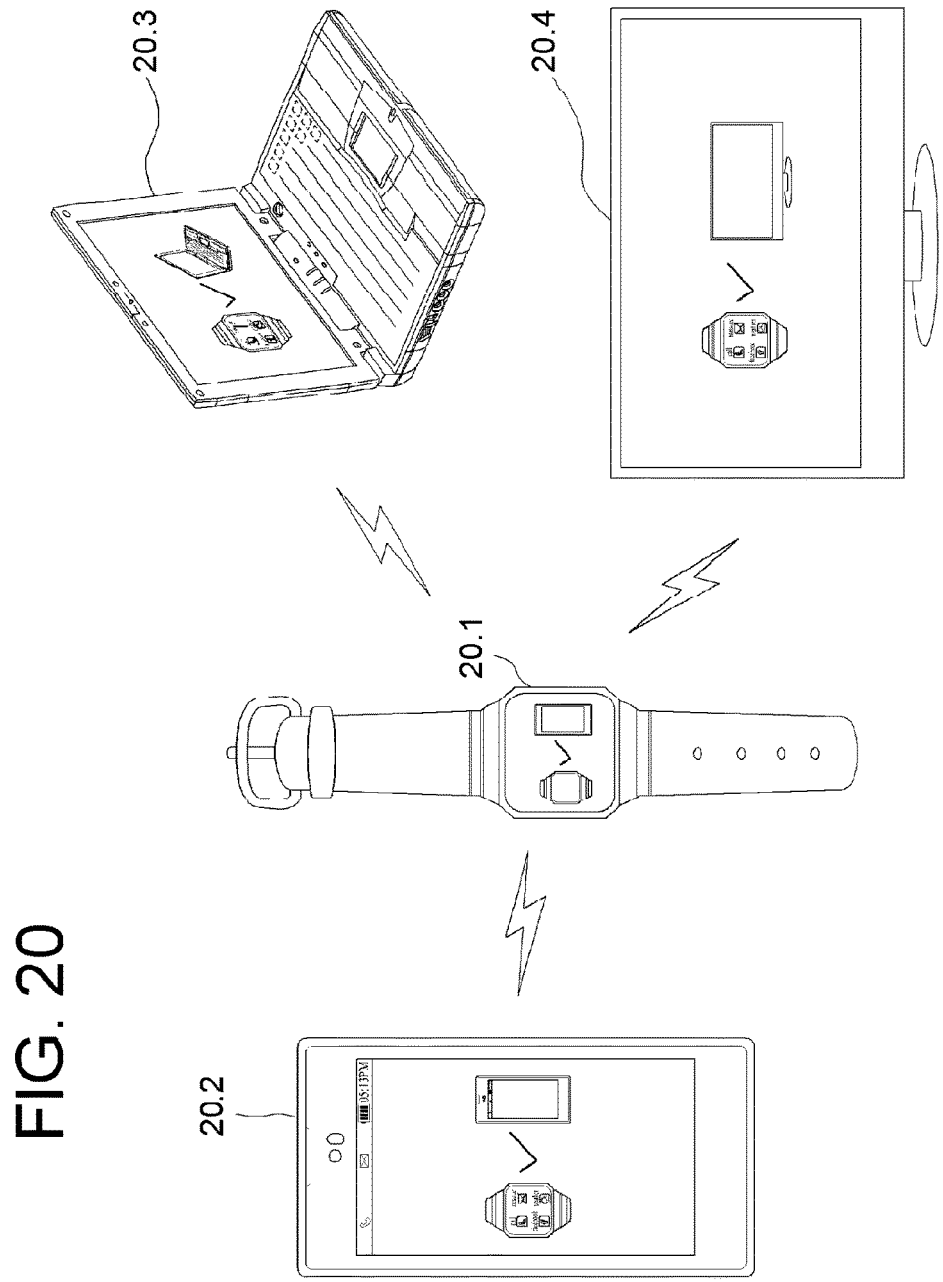
FIG. 20 is a diagram illustrating pairing of a smart watch with an external digital device.

FIG. 20 is a diagram illustrating pairing of a smart watch with an external digital device. FIG. 20 illustrates pairing performed between the smart watch 20.1 and an external digital device 20.2 such as a smart phone. The external digital device 20.2 may be a digital device that can perform communication with the smart watch 20.1. For example, the external digital device 200 may include a smart phone, a notebook computer 20.3, an Internet Protocol Television (IPTV) 20.4, etc. as shown in FIG. 20.

Pairing refers to connection for data transmission/reception between the smart watch 20.1 and the external digital device 20.2. When pairing is performed, the smart watch 20.1 and the external digital device 20.2 communicate with each other to enable two-way data transmission/reception. In this disclosure, the smart watch 20.1 may be paired with the external digital device 20.2 using a communication unit (not shown). In addition, in this disclosure, pairing may be performed through Bluetooth, Near Field Communication (NFC), etc. As an example, pairing may be performed through user input using the smart watch 20.1 or the external digital device 20.2. The user input may include touch input and voice input. For example, the smart watch 20.1 may provide a separate button or a user interface for communication with the external digital device 20.2. The user may perform communication between the smart watch 20.1 and the external digital device 20.2 through user input using the button or the user interface.

If communication access is achieved, the smart watch 20.1 may exchange data with the external digital device 20.2 in a session open state. Meanwhile, the smart watch 20.1 may perform pairing with a plurality of external digital devices 20.2, 20.3, and 20.4. In this case, the smart watch 20.1 may achieve communication access through pairing and thus may selectively exchanges data with the plural external digital devices 20.2, 20.3, and 20.4.

The smart watch 20.1 may detect the paired external digital device 20.2 to determine a notification device that will provide a notification of an event occurring in the smart watch 20.1 or the external digital device 20.2. The notification device may be a device that provides a notification of an event occurring in at least one of the smart watch 20.1 and the external digital device 20.2. In this disclosure, the notification device may include at least one of the smart watch 20.1 and the external digital device 20.2.

The event occurring in at least one of the smart watch 20.1 and the external digital device 20.2 may be a state change occurred from at least one of the smart watch 20.1 and the external digital device 20.2. For example, the event may include an incoming telephone call, text message reception, new message reception of a Social Networking Service (SNS), scheduled alarm, weather alert, etc. The notification of the occurred event may include notifying the user of the above-described event. For example, the notification may be occurred in the form of a text message notification, a speech notification, a vibration notification, etc. The notification device may be determined according to whether the user is wearing the smart watch 20.1, whether the smart watch 20.1 is paired with the external digital device 20.2, or the distance between the smart watch 20.1 and the external digital device 20.2.

On the other hand, in determining a notification device including at least one of the smart watch 20.1 and the external digital device 20.2 in this disclosure, the external digital device 20.2 may be set to a main device and the smart watch 20.1 may be set to a sub device. In this case, the external digital device 20.2 has priority over the smart watch 20.1 as the notification device under the same condition so that the external digital device 20.2 may provide the notification to the user. Conversely to the above case, the smart watch 20.1 may be set to the main device and the external digital device 20.2 may be set to the sub device. Notably, in description of this disclosure, the external digital device 20.2 is assumed to be the main device.

In consideration of the above description, the disclosure is directed to a method for determining which device will provide a notification of an event occurring in at least one of the smart watch 20.1 and the external digital device 20.2, in the smart watch 20.1 paired with the external digital device 20.2. The disclosure is directed to a method for the smart watch 20.1 to determine a notification device based on wearing/non-wearing of the smart watch and the distance between the smart watch 20.1 and the external digital device 20.2.

In one exemplification, the smart watch 20.1 may determine the notification device that provides a notification for at least one of the smart watch 20.1 and the external digital device 20.2, based on a smart watch worn mode or unworn mode. For example, in the smart watch worn mode, the smart watch 20.1 may determine the smart watch 20.1 as the notification device. In this case, the smart watch 20.1 may provide a notification of an event occurring in at least one of the smart watch 20.1 and the external digital device 20.2. For instance, in the smart watch unworn mode, the smart watch 20.1 may determine the external digital device 20.2 as the notification device. At this time, the smart watch 20.1 may transmit a notification start signal to the external digital device 20.2 so that the external digital device may provide a notification of an event occurring in at least one of the smart watch 20.1 and the external digital device 20.2.

In another exemplification, the smart watch 20.1 may determine the notification device that provides the notification for at least one of the smart watch 20.1 and the external digital device 20.2, according to whether there is the external digital device 20.2 paired with the smart watch 20.1. For example, the smart watch 20.1 may determine the smart watch 20.1 as the notification device when the external digital device 20.1 is not paired therewith. Further, for example, the smart watch 20.1 may determine at least one of the smart watch 20.1 and the external digital device 20.2 as the notification device, when the external digital device 20.2 is paired therewith.

As still another example, the smart watch 20.1 may determine the notification device that provides a notification as at least one of the smart watch 20.1 and the external digital device 20.2, based on a distance between the smart watch 20.1 and the external digital device 20.2 paired with the smart watch 20.1. For example, if the smart watch 20.1 and the external digital device 20.2 are within a preset distance, the external digital device 20.2 may be determined as the notification device. In addition, if the smart watch 20.1 and the external digital device 20.2 are separated by more than a preset distance, the smart watch 20.1 and the external digital device may be determined as the notification device.

Furthermore, the smart watch 20.1 may determine the notification device based on the mode of the smart watch 20.1 and the distance between the smart watch 20.1 and the external digital device 20.2.

Figure 21:
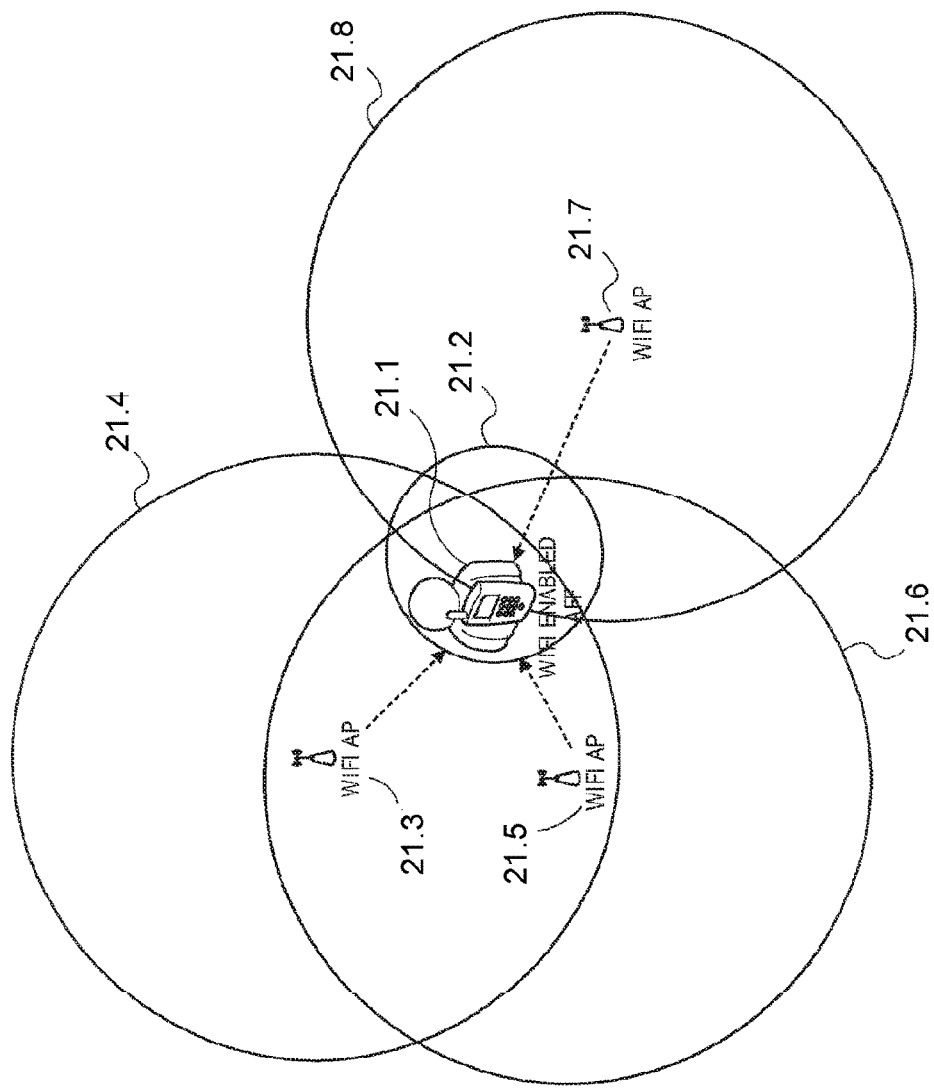
FIGS. 21, 22, and 23 illustrate a transaction sequence to facilitate client-based triangulation using a dynamic geodetic triangulation mechanism according to one exemplification of the present application.
Figure 22:
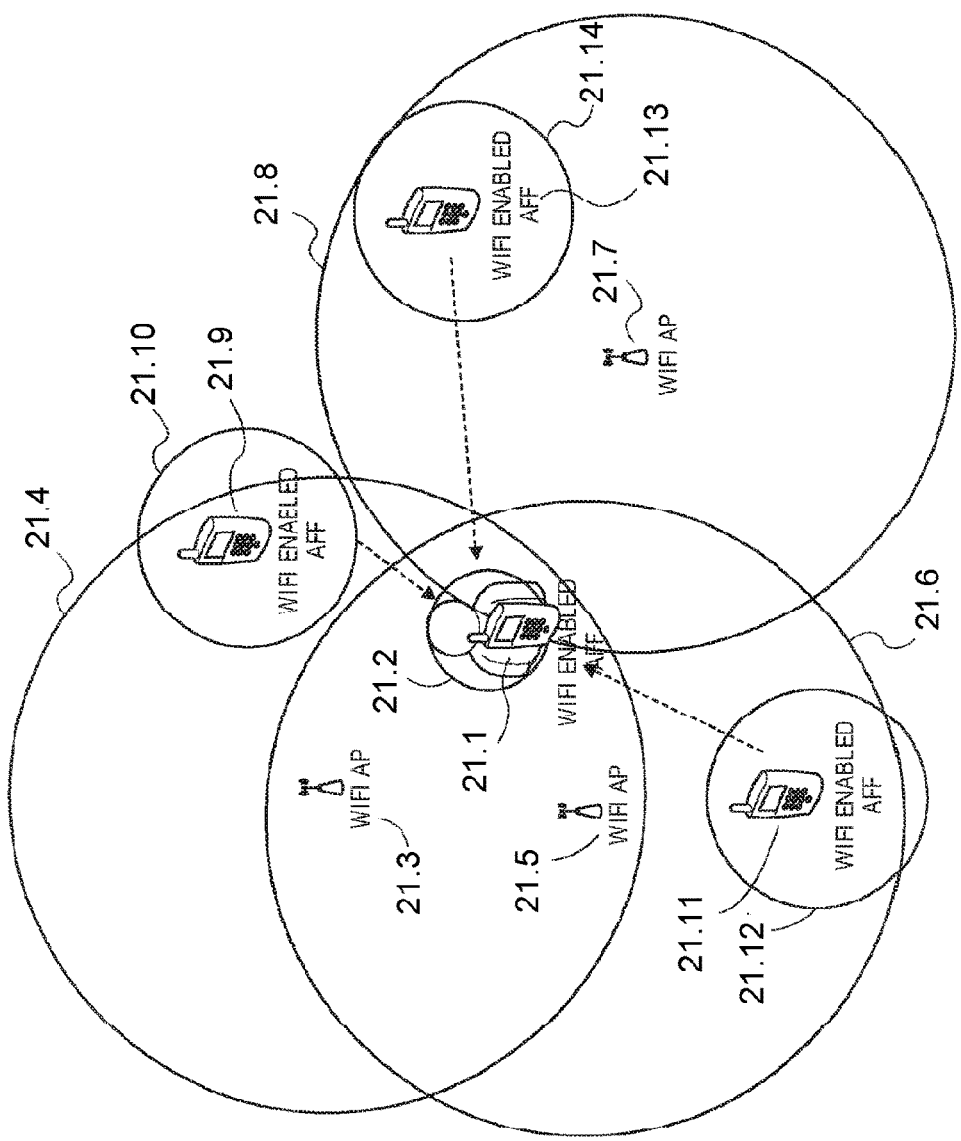
Figure 23:
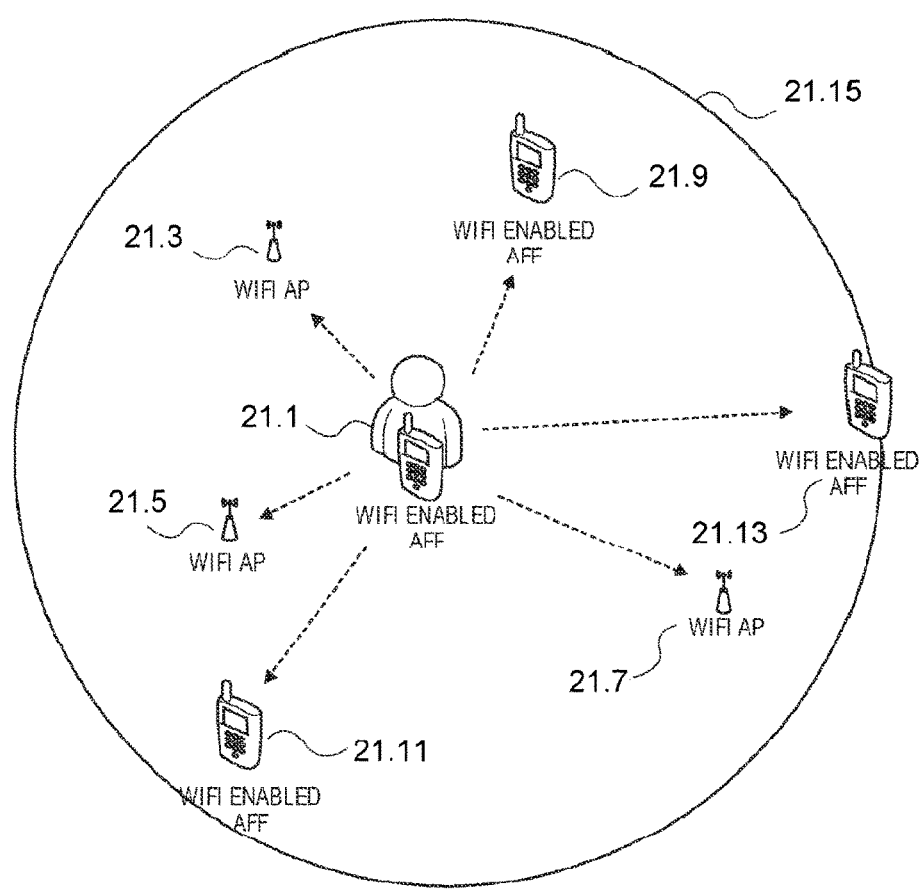

FIGS. 21, 22, and 23 illustrate a transaction sequence to facilitate client-based triangulation using a dynamic geodetic triangulation mechanism according to one exemplification of the present application. Referring to FIG. 21, a Wi-Fi-enabled client computing device 21.1 seeks to locate itself (e.g., a roaming computing device (e.g., a smartphone belonging to a user) to find its own geographic location and/or a destination,) by recognizing and/or connecting with any available locations that are of highest confidences, such as any number of available Wi-Fi access points 21.3, 21.5, 21.7 of highest confidence within a defined area or range of the computing device 21.1. For example and as illustrated, each circle 21.4, 21.6 and 21.8 represents a wireless range of its corresponding Wi-Fi access point 21.3, 21.5 and 21.7, respectively. Similarly, circle 21.2 represents the range or access of the client device 21.1 which is shown as overlapping (or in contact) with other circles 21.4, 21.6, 21.8.

Let us now suppose the client device 21.1 belongs to an individual user seeking to find a specific location. In one exemplification, as soon as the client device 21.1 approaches the location's area, it is first put in contact with one or more of those AP locations 21.3, 21.5, 21.7 (as represented by their corresponding circles 21.4, 21.6, 21.8) that carry the highest weight, such as Wi-Fi APs 21.3, 21.5, 21.7 at places around the specific location. In other words, AP locations 21.3, 21.5, 21.7 having the highest confidence take high priority and thus are used first as the highest weight in this client-side triangulation (over other low confidence locations, such as other roaming client devices, etc., as will be further described with reference to FIG. 22). In one exemplification, one of the high-weight or static AP 21.3, 21.5, 21.7 may include a beacon from a client device similar to the client device 21.1 belong to a user being stationary at the same location for a defined period of time as predefined by the triangulation mechanism and/or any of the participants, such as by the user of the computing device 21.1 who then feeds the time period information into a triangulation mechanism via the computing device 21.1.

Referring now to FIG. 22, once the high-weight APs 21.3, 21.5, 21.7 have been identified and put in touch with the client device 21.1, low-weight locations 21.9, 21.11 and 21.13 (e.g., roaming client computing devices) are then identified and put in contact with the client device 21.1 as represented by their corresponding area or signal or access circles 21.10, 21.12 and 21.14, respectively, that are shown as overlapping with other circles 21.4, 21.6, 21.8. For example and in one exemplification, these low-weight locations 21.9, 21.11, 21.13 include Wi-Fi-enabled roaming client computing devices that belong to other users who are within the predefined area around the computing device 21.1, such as near or at a specific location. For example, the users of these Wi-Fi-enabled computing devices 21.9, 21.11, 21.13 may include other patients in the facility as the user of the client device 21.1, which helps with and results in a better knowledge of the geographic positioning of the client device 21.1. In other words, first, the high-weight, low-confidence locations associated with static APs 21.3, 21.5, 21.7 are put in proximity and connection with the client device 21.1, which is then followed by putting the low(er)-weigh, low(er)-confidence computing devices 21.9, 21.11, 21.13 (that beacon out their locations) in proximity with the client device 21.1 to improve the accuracy and confidence of the client device's 21.1 geographic location.

In one exemplification, these low-weight locations of Wi-Fi enabled roaming computing devices 21.9, 21.11, 21.13 and may be determined based on the low confidence beacons (such as locations or location-related updates (e.g., one or more users of the client devices 21.9, 21.11, 21.13 updating their locations) that are received from these client devices 21.9, 21.11, 21.13. This client-side triangulation technique helps the client device 21.1 (and thus the user of the client device 21.1) determine its exact location in relation to in a specific location without having the user to access the Internet on the client device 21.1, which may not be possible due to bad reception, such as the client device 21.1 being indoors and/or not having a clear view of the sky (and thus, the satellites).

In one exemplification, the location SSID module of the triangulation mechanism communicates the access location information between the client device 21.1 and the APs 21.3, 21.5, 21.7 and other roaming client devices 21.9, 21.11, 21.13 without having the client device 21.1 (and other participating client devices 21.9, 21.11, 21.13) connect with a Wi-Fi infrastructure. It is the static indicator that differentiates between the high-weight static configured locations 21.3, 21.5, 21.7 and the low-weight roaming locations 21.9, 21.11, 21.13. Similarly, the signal strength predictor facilitates the client device 21.1, the static APs 21.3, 21.5, 21.7, and the roaming client devices 21.9, 21.11, 21.13 to predict their signal strength, while the confidence indicator facilitates the client device 21.1, the static APs 21.3, 21.5, 21.7, and the roaming devices 21.9, 21.11, 21.13 to broadcast or advertise their confidence level relating to their own location which is then received by the computing devices 21.1, 21.9, 21.11, 21.13 (and the static configured APs 21.3, 21.5, 21.7) and used to assign (e.g., adjust or re-adjust) weight to each confidence level (e.g., high weight, low weight, medium weight, etc.). These weighted confidence levels are used to add confidence to each AP or client device's current learned location (e.g., the client device's 21.1 current location with respect to its desired destination of a location).

FIG. 23 illustrates the client device 21.1 beacons out its position to others, such as to the high-weight APs 21.3, 21.5, 21.7, low-weight client devices 21.9, 21.11, 21.13, etc., so that each participating AP 21.3, 21.5, 21.7 and client device 21.9, 21.11, 21.13 can calibrate its own location using the information being beaconed out by the client device's 21.1. This beaconing out by the client device 21.1 and the collective confidence in learned positions of the participating APs 21.3, 21.5, 21.7 and client devices 21.9, 21.11, 21.13 is represented by the illustrated circle 21.15. Stated differently, once the client device 21.1 has determined its location (as aforementioned with reference to FIGS. 21 and 22), it then broadcasts its own location to APs 21.3, 21.5, 21.7 and client devices 21.9, 21.11, 21.13 so they may benefit from this information and gain confidence in their own positions, particularly the client devices 21.9, 21.11, 21.13 that are on the move.

Figure 24:
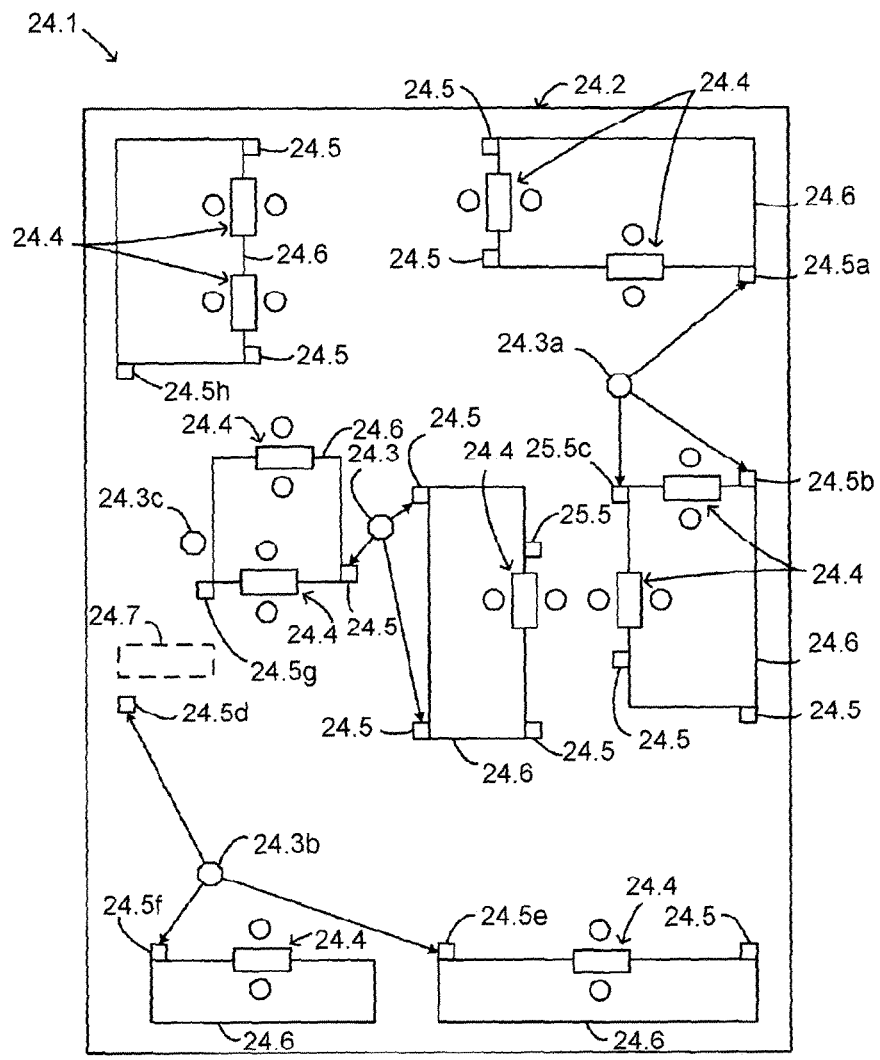
FIG. 24 is a schematic plan view representation of an object tracking system.

FIG. 24 is a schematic plan view representation of an object tracking system 24.1. The object tracking system 24.1 is installed in a factory facility 24.2. The object tracking system 24.1 utilizes tags 24.3 (represented in the drawing by octagonal symbols that also serve to represent objects, not separately shown, to which the tags are affixed to permit tracking of the objects).

The object tracking system 24.1 utilizes two different procedures—proximity detection and triangulation—to track the tags 24.3. Interrogation gates 24.4 are used for proximity detection, and triangulation stations 24.5 allow tag locations to be determined by triangulation. Another significant element of the system 24.1, but not shown in the drawing, is a central computer that is coupled by signal paths (also not shown) to the interrogation gates 24.4 and triangulation stations 24.5.

In accordance with conventional practices, a tag 24.3 that is in proximity to an interrogation gate 24.4 receives an interrogation signal from the interrogation gate and responds to the interrogation signal by transmitting a response 452 signal that includes a tag identification code that uniquely identifies the tag. The interrogation gate then effectively reports to the central computer that the particular tag is at the interrogation gate. The interaction between the tag and the interrogation gate may be in accordance with conventional RFID (radio frequency identification) practices. In other variations, the interrogation gate may read a barcode or the like from the tag.

The tags 24.3 send out signals at brief regular intervals which are received by triangulation station 24.4. By using the triangulation stations 24.4, the central computer utilizes a triangulation procedure to determine the location of tags that are not in proximity to one of the interrogation gates 24.3. The central computer may use a differential time of arrival (DTOA) procedure in which a tag ID signal transmitted by a tag 24.3 is received by three or more of the triangulation stations 24.4. Differences in the timing at which the tag ID signal is received at each triangulation station are used by the central computer to calculate the location of the tag, based on the locations of the stations 108 which received the tag ID signal. For example, in FIG. 24, a tag ID signal transmitted by tag 24.3a is received by line-of-sight at triangulation stations 24.51, 24.5b, 24.5c, thereby allowing the location of tag 24.3a to be determined by triangulation. Similarly, a tag ID signal transmitted by tag 24.3b is received by triangulation stations 24.5d, 24.5e, 24.5f so that the location of tag 24.3b can be determined by triangulation.

The "MOBY R" object locating system available from Siemens A G is an example of a system that employs DTOA to locate objects.

Figure 25:
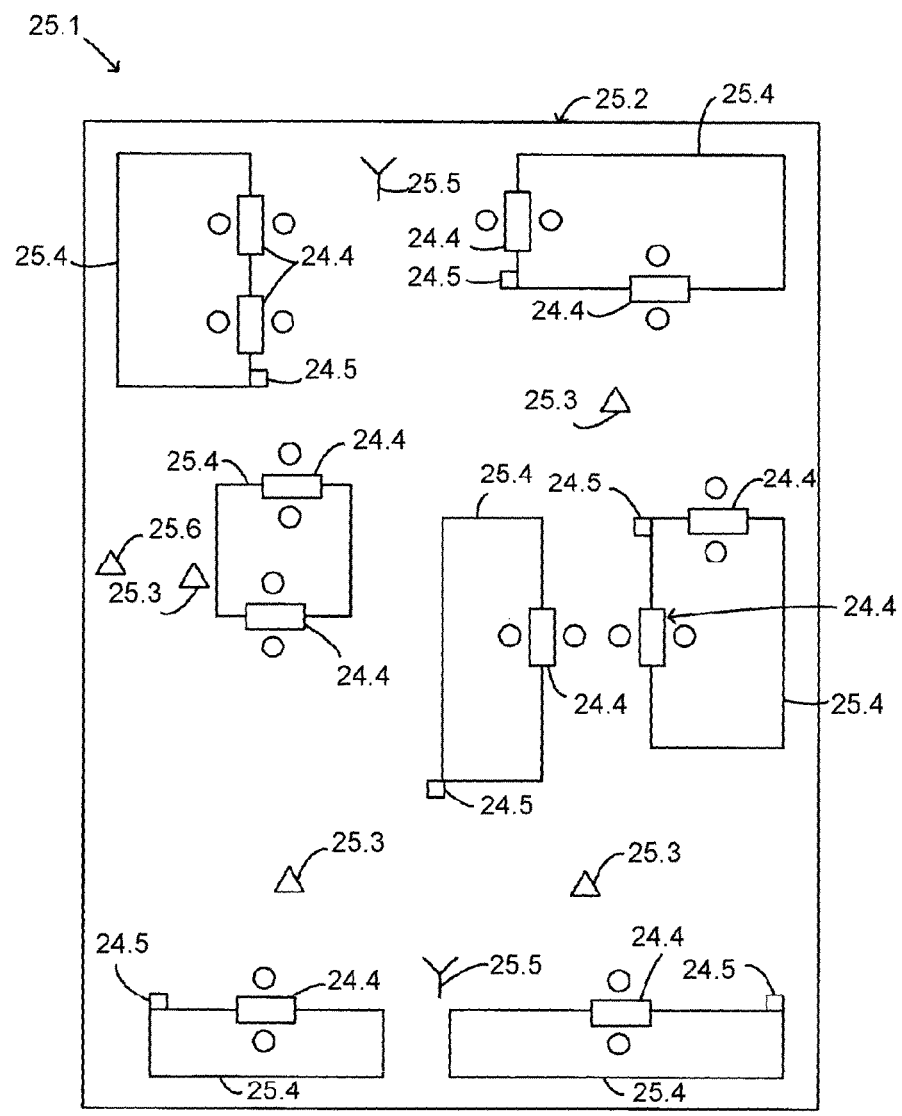
FIG. 25 is a schematic plan view representation of another object tracking system.

FIG. 25 is a schematic plan view representation of an object tracking system 25.1 in accordance with some aspects of the present application.

The object tracking system 25.1 is installed, at least in part, in a factory building 25.2. The system 25.1 includes tags 25.3, represented in the drawing by small triangles. (The triangles may also be considered to represent objects to which the respective tags are affixed to permit tracking of the objects. The objects are not separately shown.) In some exemplifications, the factory building 25.2 is employed for assembly of motor vehicles, and each tag 25.3 is affixed to a respective vehicle that is being assembled or has been assembled at the factory building 25.2. Although only a few tags 25.3 are indicated for purposes of illustration in FIG. 25, in practice the number of tags included in the system 25.1 may be in the thousands. The tags may have features provided in accordance with some aspects of the present applications, and are described in more detail below.

The object tracking system 25.1 also includes interrogation gates 24.4 and triangulation stations 24.5, which may be essentially the same as, or generally similar to, the items of the same names discussed above in connection with FIG. 24. It will be noted that the number of triangulation stations shown in FIG. 25 is substantially less than the number shown in FIG. 24, notwithstanding that the building 25.2 has substantially the same types of obstructions 25.4 as the building of FIG. 24.

Also included in the object tracking system in accordance with some aspects of the invention are antennas 25.5, which are provided to receive from the tags 25.3 tag self-tracking position information, as described in more detail below. Although not separately shown, each antenna may have associated therewith appropriate receive circuitry as well as a capability for buffering data and relaying the data to a central (server) computer, which is discussed below. Thus each antenna symbol 25.5 may be considered to represent a receiver for receiving tag self-tracking position information transmitted by tags 25.3.

Figure 26:
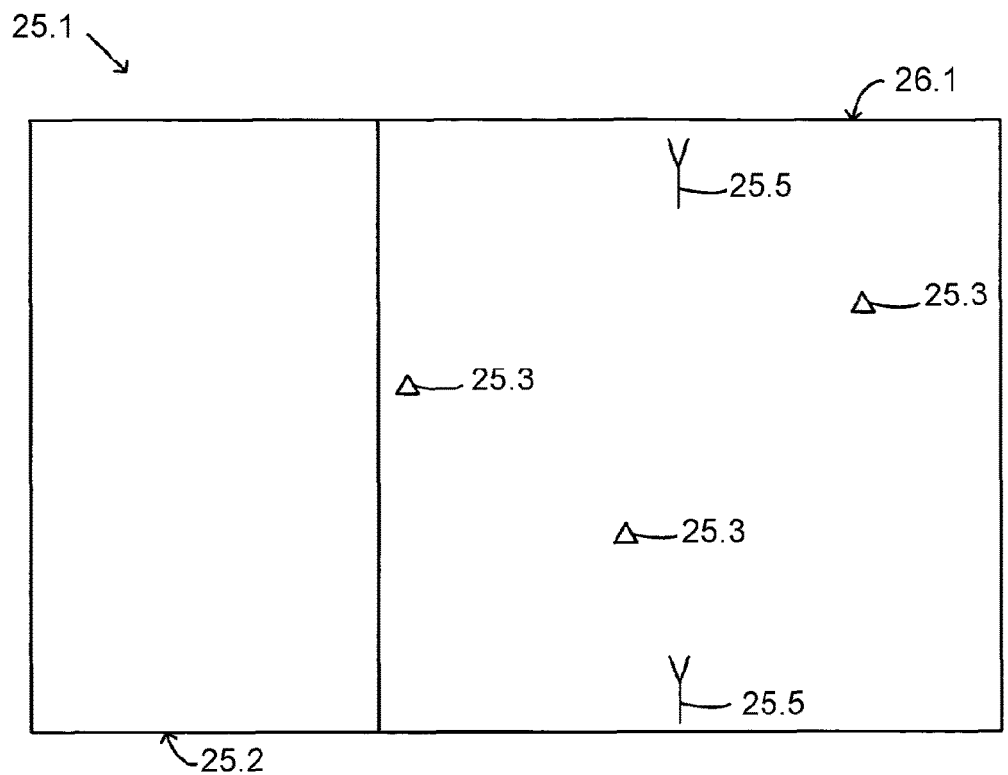
FIG. 26 is a schematic plan view representation of an alternative exemplification of the object tracking system of FIG. 25.

FIG. 26 illustrates, in the form of a schematic plan view, an alternative exemplification of the object tracking system 25.1, including the factory building 25.2 shown in FIG. 25, together with an associated parking, storage and/or testing lot 26.1. It will be observed that the lot 26.1 has tags 25.3 of the object tracking system present therein, and that antennas 25.5 of the object tracking system are installed in the lot 26.1. Although not shown in detail, it may be assumed that the factory building 25.2 is equipped with system components as illustrated in FIG. 25.

According to one possible exemplification, the smartwatch can include a wireless or radio-frequency identification (RFID) tag to permit tracking the position and status of the smartwatch. A wireless tag to be associated with the object to be linked, tracked, or both is disclosed along with an electronic device for communicating with the tag and updating the information to an external device, such as a computer, network, or the cloud. Information such as, but not limited to time, position (including latitude, longitude, and altitude), speed, direction, temperature, and identification can be transmitted for either real-time linking/tracking and analysis, or a historical view. In one exemplification, the electronic device for communicating with the tag is a cellular phone, a tablet computer, a laptop computer, a pair of electronic glasses, or a watch.

According to another exemplification, a wireless tag for determining the position of an attached physical object or status of an environment in which the tag is placed is disclosed. In one exemplification, the wireless tag includes a power source for providing electrical power to the wireless tag, a radio transmitter and receiver system for wirelessly exchanging data and command with an electronic device, and a user interface including at least one input and at least one output, wherein the electronic device determines the location or status of the electronic device and a status of whether the distance between the electronic device and wireless tag exceeds a predetermined distance and wirelessly communicates data including the time, the location of the electronic device (including latitude, longitude, and altitude), speed and the status. In another exemplification, the electronic device communicates data to the network at predetermined period intervals and/or upon the initiation of a predetermined event. In still another exemplification, the wireless tag has a thickness of about 10 mm or less, and in another exemplification about 6 mm or less. In yet another exemplification, the communication between the tag and electronic device is encrypted. In yet still another exemplification the wireless tag includes one or more sensors having an output reading. In another exemplification, a plurality of tags is provided.

According to another exemplification, a system for tracking the position of an object is disclosed. In one exemplification, the system includes a wireless tag including a first radio transmitter and receiver system and a user interface including at least one input and at least one output; an electronic device includes a second radio transmitter and receiver system in communication with the first radio transmitter and receiver system, a user interface including at least one output, a module for determining the position of the electronic device, a module for determining the distance or proximity and/or direction of the tag from the device and also for determining a status of whether the distance between the electronic device and wireless tag exceeds a predetermined distance, and a data transmitter for transmitting commands and data including the position of the electronic device and status of the distance between the electronic device and wireless tag; and an external device receiving the data transmitted by the data transmitter and storing the data in a computer readable storage medium. In another exemplification, the system includes a second wireless tag secured to a second object to be linked or tracked, the second wireless tag including a third radio transmitter and receiver system; and a user interface including at least one input and one output; wherein the second radio transmitter and receiver system is in communication with the third radio transmitter and receiver system, the electronic device includes a module for determining the distance or proximity and/or direction of the tag from the phone and also for determining a second status of whether the distance between the electronic device and second wireless tag exceeds a second predetermined distance, and the data transmitter for transmits data including the second status.

According to another exemplification, a method for monitoring the location of an object is disclosed. In one exemplification, the method includes securing a wireless tag to the object, wherein the wireless tag includes a first radio transmitter and receiver system for transmitting and receiving a radio frequency signal; providing a first identification for the wireless tag; associating the wireless tag with an electronic device, wherein the electronic device includes a second radio transmitter and receiver system for transmitting and receiving a radio frequency signal and the electronic device is capable of determining the position of the electronic device; determining the position of the electronic device; providing a second identification for the electronic device; receiving with the second radio transmitter and receiver system the radio frequency signal from first radio transmitter and receiver system; determining with the electronic device the distance or proximity and/or direction of the tag from the phone and also a status of whether the distance between the wireless tag and the electronic device exceeds a predetermined distance based at least in part on the strength or absence of the radio frequency signal; and transmitting data including the first identification, the second identification, the time, the speed, the position of the electronic device, and the status to an external device. In another exemplification, the radio transmitter and receiver systems are Bluetooth transceivers and the tag has a thickness of about 10 mm or less or about 6 mm or less. In still another exemplification, the wireless tag includes an alarm and the second Bluetooth transceiver sends a signal to the first Bluetooth transceiver to activate the alarm or carry out any other predetermined action or command when the status changes because the predetermined distance was exceeded. Alarming or carrying out other actions or commands, could also be initiated by the user, by demand, from any part of the overall system (tag, phone, cloud).

According to another exemplification, a method of monitoring a patient in a health care facility is disclosed. In one exemplification, the method includes attaching a wireless tag to the patient, the wireless tag including a first radio transceiver for transmitting and receiving a radio frequency signal and a tag alarm; associating the wireless tag with an electronic device, the electronic device including a second radio transceiver for transmitting and receiving a radio frequency signal and a device alarm, wherein the electronic device is capable of determining the position of the electronic device; providing an allowable distance or range; monitoring the radio frequency signal from the first radio transceiver received by the second radio transceiver and activating the device alarm if the radio frequency signal is broken; monitoring the radio frequency signal from the second radio transceiver received by the first radio transceiver and activating the tag alarm if the radio frequency signal is broken; and determining with the electronic device a status of whether the distance between the wireless tag and the electronic device exceeds the allowable distance or range based at least in part on the strength or absence of the radio frequency signal; wherein the electronic device activates at least one of the tag alarm and device alarm, determines the position of the electronic device and wirelessly transmits data including the time, the temperature, and the position of the electronic device to an external device if the distance exceeds the allowable distance or range. In another exemplification, the method includes saving locally (on the device) and wirelessly transmitting data to the external device including the time and position and speed of the electronic device each time the determining step is performed.

According to another exemplification, a method of providing a positioning service to a customer is disclosed. In one exemplification, the method includes providing a plurality of wireless tags to the customer for small or no charge, each tag having a unique identification and including a power source for providing electrical power to the wireless tag, a radio transceiver for wirelessly exchanging encrypted data with an electronic device, and a user interface including at least one input and at least one output wherein the electronic device determines the position of the electronic device and a status of whether the distance between the electronic device and wireless tag exceeds one or more predetermined distances and wirelessly communicates data including the position, with time and speed of the electronic device and the status; providing a computer-readable medium containing an application programming interface and/or software development kit to the customer and/or a developer, the application programming interface and/or software development kit being configured to support a software application on the tag and/or the electronic device and/or the cloud, wherein the electronic device includes a radio transceiver capable of communicating with the wireless tag radio transceiver, a user interface including at least one input and one output, a module for determining the position, the speed and time of the electronic device, a module for determining a status of whether the distance between the electronic device and wireless tag exceeds one or more predetermined distance, and a data transmitter for transmitting data including the position, with time and speed of the electronic device and status of the distance between the electronic device and wireless tag to an external device for storage in a computer readable storage medium and carrying out commands/actions; and associating the plurality of tags with the application programming interface and/or software development kit for a periodic fee or a consumption-based fee, such as based on how many tags being linked, how many times data or commands are communicated or how much data or commands are communicated in a given period. In another exemplification, the method includes developing programs utilizing the application programming interface and/or software development kit and allowing access to the programs for a free or for a fee.

Figure 27:
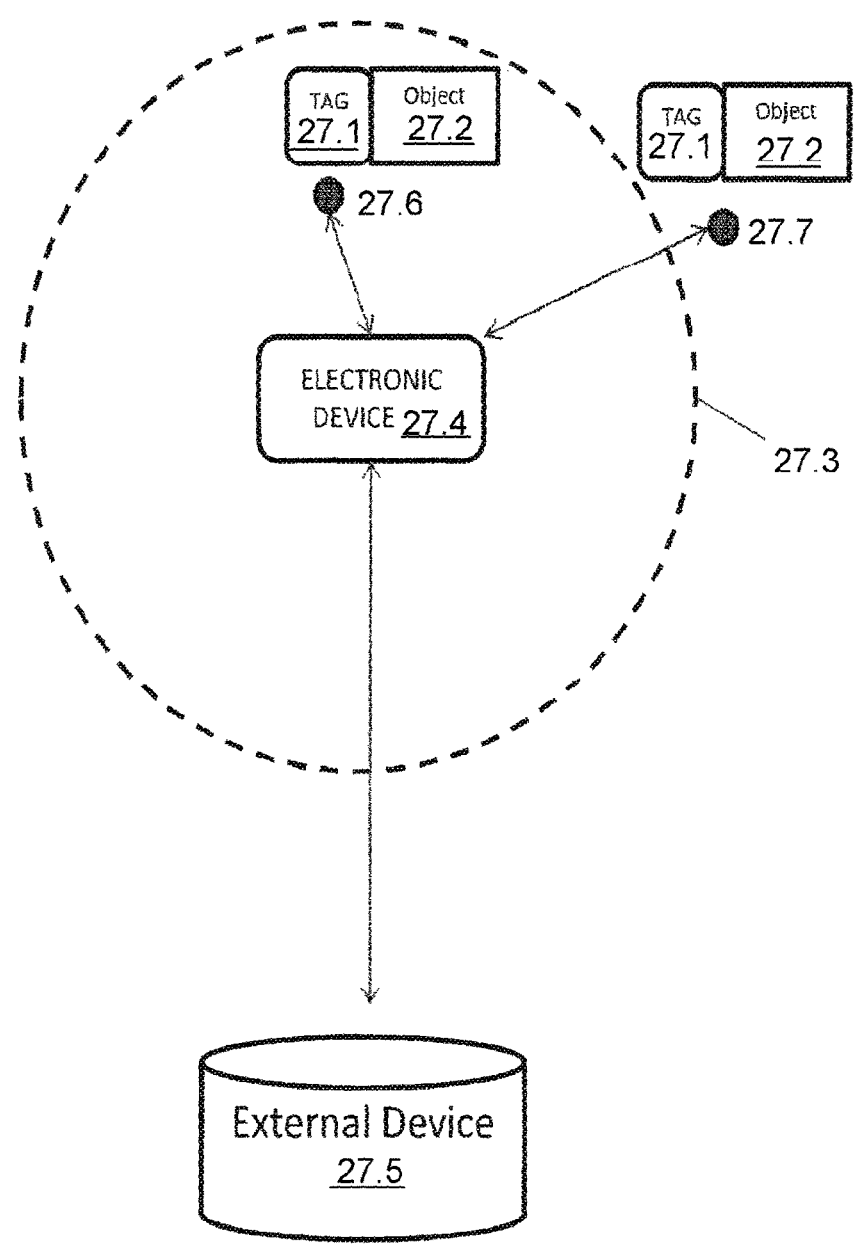
FIG. 27 shows an exemplification of a tracking system.

According to another exemplification shown in FIG. 27, an electronic device 27.4, such as a cellular phone or smartwatch, is provided. Electronic device includes a module determining the current or last known position of electronic device 27.4. In some exemplifications, the current or last position includes one or more of the current or last known altitude, the current or last known latitude and longitude, and the current or last known speed of electronic device 27.4.

Also shown in the exemplary, non-limiting example illustrated in FIG. 27, an object 27.2, such as a wallet is attached to a wireless tag 27.1. Wireless tag 27.1 includes a radio transceiver in communication with a radio transceiver included in electronic device 27.4. Electronic device 27.4 monitors the strength of the radio signal received from wireless tag 27.1 to determine the distance between electronic device 27.4 and wireless tag 27.1. When the object 27.2 and tag 27.1 are within a first distance 182 from electronic device 27.4, such as at point 27.6, electronic device 27.4 determines the status of wireless tag 27.1 to be "in range." When the object 27.2 and tag 27.1 are beyond the distance from electronic device 27.4, such as at point 27.7, electronic device 27.4 determines the status of wireless tag 27.1 to be "out of range." When the status of wireless tag 27.1 change from "in range" to "out of range," either electronic device 27.4, wireless tag 27.1, or both alarm.

As shown in the exemplary non-limiting example illustrated in FIG. 27, electronic device periodically sends information relating to its current or last known location and the status of wireless tag 27.1 to an external device 27.5, such as an external network or cloud data service. When the status of wireless tag 27.1 change from "in range" to "out of range," electronic device 27.4 sends information relating to its current or last known location and the change of status to the external device 27.5. In this way, a user is given both an alarm when the change in status occurs, as well as a last known location for object 27.2 based on the strength of the radio signal from tag 27.1 received by wireless device 27.4.

Figure 30:
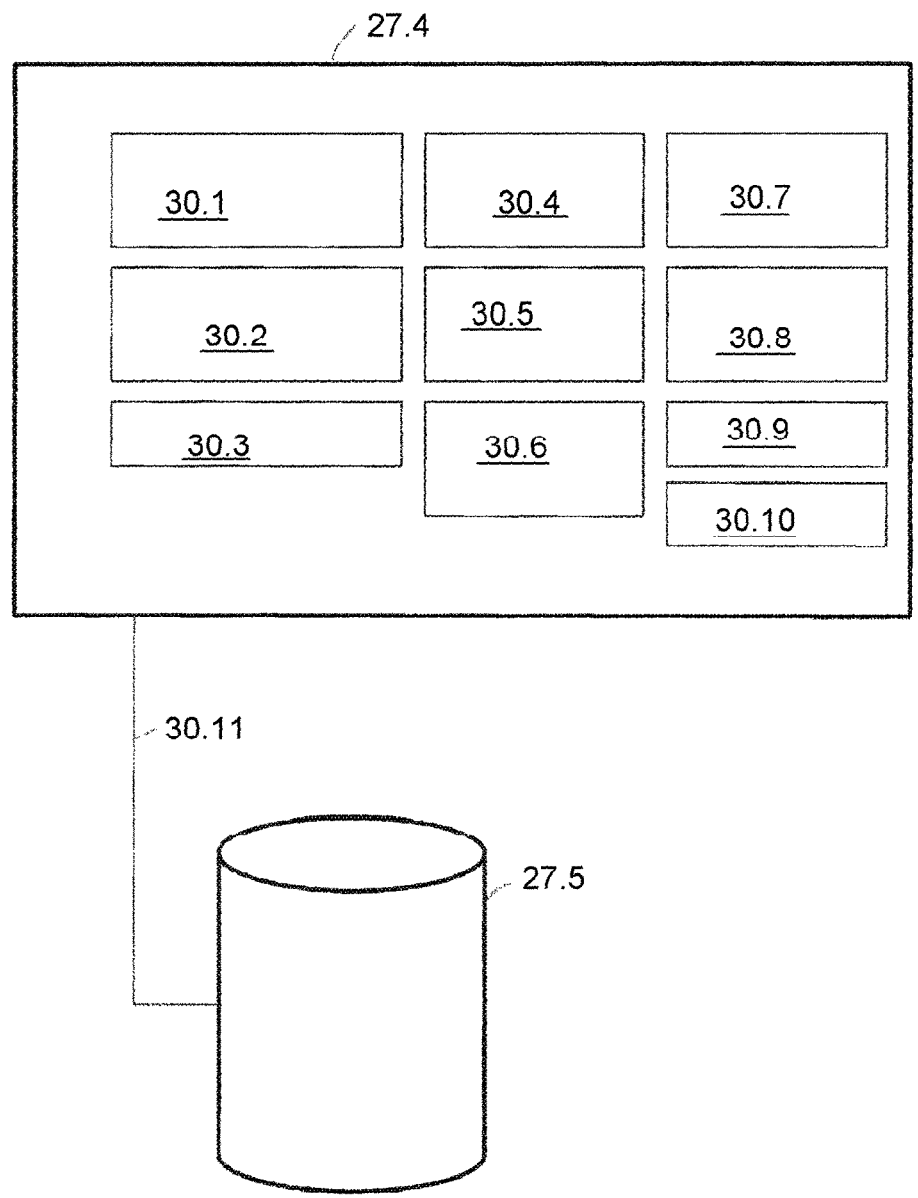
FIG. 30 shows components of a tracking system.

In one exemplification shown in FIG. 30, electronic device 27.4 is a cellular phone. In another exemplification, electronic device 27.4 is a tablet or laptop computer or portable computing device. In still another exemplification, electronic device 27.4 is an electronic watch or wristband. In yet still another exemplification, electronic device 27.4 is a portable music player. Other suitable electronic devices, including but not limited to a pair of electronic glasses or sunglasses, may also be used.

In one exemplification, electronic device 27.4 includes absolute position data receiver 30.1 and absolute position module 30.2. Absolute position data receiver 30.1 receives location-based data from external sources. In one exemplary exemplification, absolute position data receiver 30.1 receives data from a combination of cellular towers, wireless networks including Wi-Fi networks, and global positioning systems (GPS). Absolute position module 30.2 determines the location of electronic device 27.4 from the location based data received by data receiver 30.1. Absolute position module 30.2 determines the speed of electronic device 27.4 from the location based data received by absolute position data receiver 30.1. In one exemplary exemplification, absolute position data receiver 30.1 and absolute position module 30.2 are provided as part of the operating software of electronic device 27.4. In another exemplary exemplification, absolute position data receiver 30.1 and/or absolute position module 30.2 are included on a card, hardware, device or software program in communication with the operating software of electronic device 27.4.

In another exemplary exemplification, absolute position module 30.2 determines the latitude and longitude of electronic device 27.4. In still another exemplary exemplification, absolute position module 30.2 determines the altitude of electronic device 27.4. In yet still another exemplary exemplification, absolute position module 30.2 determines the speed of electronic device 27.4.

In the exemplary exemplification illustrated in FIG. 30, electronic device 27.4 includes radio transceiver 30.7. Radio transceiver 30.7 sends and receives data to and from other radio transceivers, including radio transceiver 28.11 incorporated in wireless tag 27.1. In one exemplification, radio transceiver 30.7 may comprise a single transceiver. In another exemplification, radio transceiver 30.7 comprises a separate transmitter and receiver. The electronic device 27.4 can also include an alarm/speaker 30.3 for sound.

In one exemplification, radio transceiver 30.7 is a Bluetooth® transceiver that operates on Bluetooth protocols. As used herein, Bluetooth includes Bluetooth, ULP Bluetooth (Ultra Low Power Bluetooth), BLE (Bluetooth Low Energy), and other standards sets by Bluetooth SIG, Inc. In another exemplification, radio transceiver operates on RF protocols. In still another exemplification, radio transceiver 30.7 operates on NFC protocols. Other suitable radio transceivers may also be used. In one exemplification, at least some of the data exchanged is encrypted.

Bluetooth connections are relatively power efficient, have relatively little interference issues, are supported by a variety of phone manufacturers and models, and allow bidirectional communication over relatively long ranges. RFID and NFC connections may require less expensive components and may use less power from power supply 28.13 of wireless tag 27.1 (see FIG. 28).

In the exemplary exemplification illustrated in FIG. 30, electronic device 27.4 includes distance monitor 30.8. In one exemplification, distance monitor 30.8 monitors communication between radio transceiver 30.7 and wireless tag 27.1. In this exemplification, distance monitor 30.8 may determine the status of the connection between electronic device 27.4 and wireless tag 27.1 to determine if the connection is dropped, broken, lost, or otherwise not present. In another exemplification, distance monitor 30.8 determines a distance between electronic device 27.4 and wireless tag 27.1 based at least in part on the strength of the signal received from wireless tag 27.1. In still another exemplification, controller 30.9 may compare the distance determined by distance monitor 30.8 with a selected distance to alert the user if the determined distance exceeds the selected or predetermined distance. In yet still another exemplification, controller 30.9 may compare the signal strength with desired signal strength from a user to alert the user if the signal strength is weaker than the desired signal strength. In another exemplification, controller 30.9 may compare the distance determined by distance monitor 30.8 with a predetermined distance or predetermined signal strength, such as but not limited to a received signal strength indicator, corresponding to a user input, such as but not limited to "Close," "Mid," or "Far." In still another exemplification, controller 30.9 may compare the signal strength with desired signal strength from a user and alert the user if the signal strength is stronger than the desired signal strength.

In the exemplary exemplification illustrated in FIG. 30, electronic device 27.4 includes data transmitter 30.4 and data receiver 30.5. Data transmitter 30.4 sends data to external device 27.5, and data receiver 30.5 receives data from external device 27.5. In one exemplary exemplification, radio transceiver 30.7 also functions as data transmitter 30.4 and/or data receiver 30.5. In another exemplary exemplification, data transmitter 30.4 and data receiver 30.5 are separate from radio transceiver 30.7. In one exemplification, data transmitter 30.4 and data receiver 30.5 exchange data with external device 27.5 using Wi-Fi standards, such as the IEEE802.11 family of standards or WiMAX standards, such as IEEE802.16. In another exemplification, data is exchanged using a wide area network standard, including but not limited to, LTE, HPSA, UMTS, GPRS, EDGE, iBurst, EV-DO. In still another exemplification, data is exchanged using a personal area network standard, including, but not limited to Bluetooth, ZigBee, ANT, and Wireless USB. Other suitable mobile data standards may also be used. In another exemplification, wireless tag 27.1 saves data locally and later communicates data to wireless device 27.4 or external network 27.5 over a wired connection. Exemplary wired connections include a USB connection, although other suitable connections may also be used.

In one exemplification, at least one of the following communications channels is encrypted: between radio transceiver 28.11 and controller 28.6, between wireless tag 27.1 and electronic device 27.4, between radio transceiver 30.7 and controller 30.9, between electronic device 27.4 and external device 27.5, within components of external device 27.5, between external device 27.5 and an external user interface.

In one exemplary exemplification, data from data transmitter 30.4 and data receiver 30.5 is exchanged with data on external device 27.5. External device 27.5 may comprise a single device or a plurality of devices in communication with each other. In one exemplification, external device 27.5 is a machine capable of storing data, including, but not limited to a computer, a laptop computer, a tablet computer, a mobile electronic device, or a server. In another exemplification, external device 27.5 is a network capable of storing data, including but not limited to a local area network, a public switched network, a CAN network, and any type of wired or wireless network. External device 27.5 is also a network or cloud data service. As used herein, a cloud service refers to remotely hosted data, remotely hosted servers, or both over the internet, web or a network which is accessible from multiple locations and devices or machines. As used herein, the term includes at least Infrastructure-as-a-Service (IaaS), Platform-as-a-Service (PaaS), Hardware-as-a-Service, and Software-as-a-Service (SaaS) service, and other remote data computation, application, management, or storage resources. As used herein, network, refers to a local area network, a private network, a public switched network such as but not limited to the Internet, a CAN network, and any type of wired or wireless network.

Figure 28:
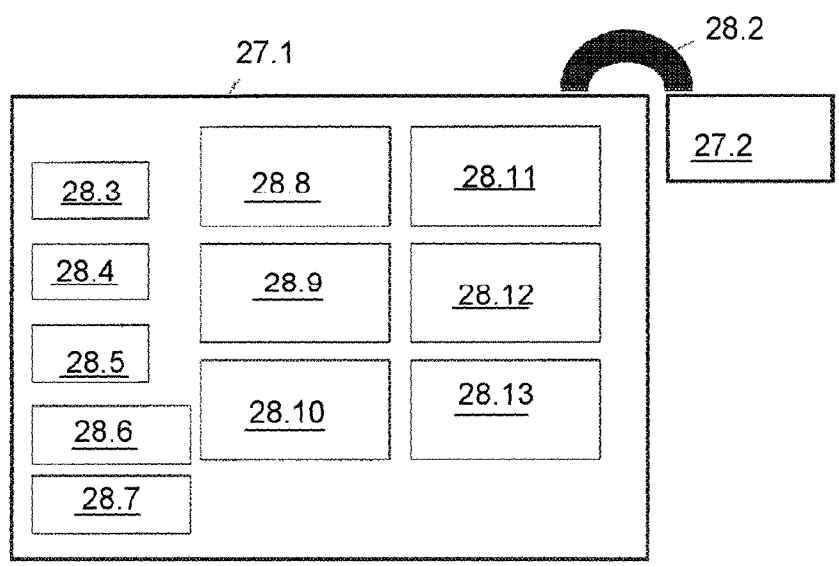
FIG. 28 shows components of a tracking system.

Referring next to FIG. 28, an exemplary wireless tag 27.1 is illustrated. In one exemplification, wireless tag 27.1 includes user interface 28.10 comprising one or more I/O modules which provide an interface between an operator and wireless tag 27.1. An operator may include a human operator or a computer, machine, or software application interfacing with wireless tag 27.1, electronic device 27.4, or external device 27.5. Exemplary I/O modules include input members and output members. Exemplary input members include buttons, such as button 28.4, switches, keys, a touch display, a keyboard, a sensor, a mouse, and other suitable devices for providing information to controller 28.6. Exemplary output devices include lights, a display (such as a touch screen), printer, speaker, visual devices, and audio devices including alarm 28.5, tactile devices, and other suitable devices for presenting information to an operator.

In the exemplary exemplification illustrated in FIG. 28, wireless tag 27.1 includes a plurality of hardware and software, including a controller 28.6. Controller 28.6 includes logic which may control operation of wireless tag 27.1. The logic of controller 28.6 may be implemented in hardware or in hardware executing software. Exemplary software may be stored in a memory 28.7. Memory 28.7 includes instructions executed by controller 28.6, as described for controller 30.9 above. Controller 28.6 may include one or more processors or other structures to implement the logic of controller 28.6.

In the exemplary exemplification illustrated in FIG. 28, wireless tag 27.1 includes radio transceiver 28.11. Radio transceiver 28.11 sends and receives data from other radio transceivers, including radio transceiver 30.7 incorporated in electronic device 27.4. In one exemplification, radio transceiver 28.11 may comprise a single transceiver. In another exemplification, radio transceiver 28.11 comprises a separate transmitter and receiver.

In one exemplification, radio transceiver 28.11 is a Bluetooth transceiver that operates on Bluetooth protocols. In another exemplification, radio transceiver 28.11 operates on RF protocols. In still another exemplification, radio transceiver 28.11 operates on NFC protocols. Other suitable radio transceivers may also be used. In one exemplification, at least some of the data exchanged is encrypted.

In the exemplary exemplification illustrated in FIG. 28 wireless tag 27.1 includes distance monitor 28.12. In one exemplification, distance monitor 28.12 monitors communication between radio transceiver 28.11 and electronic device 27.4. In another exemplification, distance monitor 28.12 may determine the status of the connection between electronic device 27.4 and wireless tag 27.1 to determine if the connection is dropped, broken, lost, or otherwise not present. In still another exemplification, distance monitor 28.12 may determine the distance or range between wireless tag 27.1 and electronic device 27.4.

In the exemplary exemplification illustrated in FIG. 28, wireless tag 27.1 includes data transmitter 28.8 and data receiver 28.9. Data transmitter 28.8 and data receiver 28.9 function similarly to data transmitter 30.4 and data receiver 30.5 of electronic device 27.4. Data transmitter 28.8 sends data to external device 27.5, and data receiver 28.9 receives data from external device 27.5. In one exemplary exemplification, radio transceiver 28.11 also functions as data transmitter 28.8 and/or data receiver 28.9. In another exemplary exemplification, data transmitter 28.8 and data receiver 28.9 are separate from radio transceiver 28.11. In one exemplification, data transmitter 28.8 and data receiver 28.9 exchange data with external device 27.5 as described above. Other suitable mobile data standards may also be used. In one exemplification, at least some of the data exchanged is encrypted. In still another exemplary exemplification, wireless tag 27.1 does not include data transmitter 28.8 and/or data receiver 28.9.

In still another exemplification, wireless tag 27.1 includes one or more sensors 28.3. Exemplary sensors 28.3 include, but are not limited to, temperature sensors, altimeters, barometers, pressure sensors, humidity sensors, chronometers, pedometers, accelerometers, level sensors, impact sensors, and compasses. Other suitable sensors may be used depending on the desired application.

In yet still another exemplification, wireless tag 27.1 may include a GPS or other suitable location detection technologies (not shown). In this exemplification, wireless tag 27.1 may communicate its position over at least one of data transmitter 28.8 and radio transceiver 28.11. Using the communicated position information, a direction to wireless tag 27.1 may be displayed or communicated on user interface 30.6 or a user interface associated with external device 27.5. In one exemplification, the direction may be saved locally in memory 28.7 associated with the electronic device 27.4. In another exemplification, the direction may be communicated to the external device 27.5 and saved in memory 30.10 associated with the electronic device 27.4. In still another exemplification, the position may be saved locally in memory 30.10 associated with the wireless tag data and later communicated to wireless device 27.4 or external network 27.5 over a wired or wireless connection, such as network 30.11.

In yet another exemplary exemplification, wireless tag 27.1 includes securing element 28.2 to secure wireless tag to object 27.2. In one exemplification, object 27.2 is a person or animal. In another exemplification, object 27.2 is an inanimate physical object. In one exemplification, securing element 28.2 includes a mechanical or chemical fastener to secure wireless tag 27.1 to object 27.2. Other securing elements 72 may also be used. In another exemplification, wireless tag 27.1 is not secured to object 27.2, but is positioned near, in, or on object 27.2, or in an environment. Other positions of wireless tag 27.1 in relation to object 27.2 may also be used.

Figure 29:
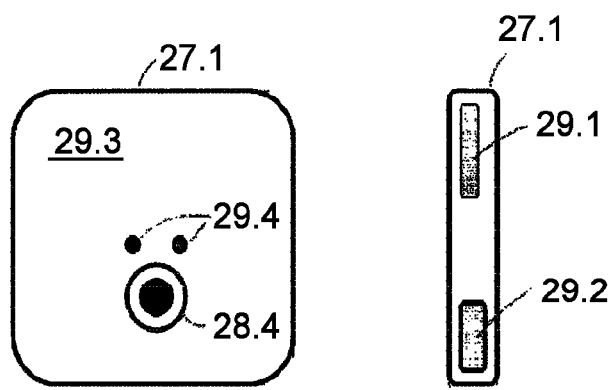
FIG. 29 shows components of a tracking system.

Referring next to FIG. 29, an exemplary wireless tag 27.1 is illustrated. The exemplary wireless tag 27.1 includes a button 28.4, plurality of lights 29.4, and speaker 29.1 for alarm 28.5 as part of user interface 28.10. In other exemplifications, other suitable inputs and outputs may be used. The exemplary wireless tag 27.1 also includes power socket 29.2 for recharging power supply 28.13. The exemplary wireless tag 27.1 also includes an area for displaying identifying information 29.3. In other exemplifications, no information is displayed on wireless tag 27.1.

According to one possible exemplification, the facial recognition system can use multilayered discriminant analysis that includes systems and methods applying an initial linear discriminate analysis to a database of face images in a more-or less conventional manner. Initial fuzzy logic then is applied to the results of the initial linear discriminate analysis to produce a subset of the database of face images. Thereafter, a subsequent linear discriminate analysis is applied to the subset of the database of face images and subsequent fuzzy logic is applied to the results of the subsequent linear discriminate analysis to produce a further subset of the subset of the database of face images. The application of the subsequent linear discriminate analysis and application of the subsequent fuzzy logic may be repeated until the further subset contains only one, or zero, face images.

Face recognition is a branch of pattern recognition, in which human visual perception in terms of face recognition is imitated in a computer. Face recognition has become one of the most important research areas of pattern recognition. In the last few decades, biometrics recognition has been an intensive field of research and consequently, a number of face recognition algorithms have been proposed by computer scientists, neuroscientists, and psychologists. Computer scientists attempt to develop methods for face recognition, whereas psychologists and neuroscientists typically work on the biological process of human face recognition.

Facial recognition is a popular biometric used for investigative, security, and anti-terrorism purposes due to its ease of end-user use and potential ability to identify an individual from distance. Unsupervised statistical methods such as Principal Component Analysis (PCA), Linear Discriminate Analysis (LDA), Direct Linear Discriminate analysis (DLDA), Independent Component Analysis (ICA), Kernel Principal Component Analysis (KPCA), and Support Vector Machines (SVM) are the most popular face recognition algorithms. These algorithms find a set of base images and represent faces as linear combinations of those base images. However, accurate facial recognition involves several challenges. For example, different types of variabilities of facial images in different environments make facial recognition more difficult and existing facial recognition algorithms less accurate. Such variabilities, which make the face recognition more complex, include face illumination, face pose, expression, eyeglasses, makeup, etc. These variabilities have a great influence when dealing with large databases of face images using existing algorithms. As a result, two issues arise in existing face recognition algorithms, feature representation and classification based on features.

Conventional face recognition methods can be classified into two groups, face and constituent. Face-based method (appearance-based technique) uses raw information from face images, i.e., pixels. These methods include PCA-, LDA-, KPCA-, and SVM-based methods, whereas constituent-based approaches use the relationships between face features, i.e., nose, lips, and eyes. Among appearance-based representation, PCA- and LDA-based methods are the two most powerful methods for dimensionality reduction and are successfully applied in many complex classification problems such as speech recognition face recognition, etc. In general, LDA-based methods perform better than PCA-based methods; but on the other hand, LDA-based methods face problems with Small Sample Size (SSS) and separability criteria. The conventional solution to misclassification for SSS problem and large data set with similar faces is the use of PCA into LDA, typically referred to as "Fisherfaces." PCA is used for dimensionality reduction, and then LDA is performed on to the lower dimensional space. However, the use of LDA over PCA results in loss of significant discriminatory information.

The facial recognition systems and methods relate to computer-implemented face recognition using multilayered discriminant analysis, which includes applying an initial linear discriminate analysis to a database of face images. Initial fuzzy logic then is applied to the results of the initial linear discriminate analysis to produce a subset of the database of face images. Thereafter, a subsequent linear discriminate analysis is applied to the subset of the database of face images and subsequent fuzzy logic is applied to the results of the subsequent linear discriminate analysis to produce a further subset of the subset of the database of face images. The application of the subsequent linear discriminate analysis and application of the subsequent fuzzy logic may be repeated until the further subset contains only one, or zero, face images.

The systems and methods described herein relate to bio-inspired face recognition using multilayered linear discriminant analysis. The present systems and methods employ a technique of classification that reduces the dataset of facial images to produce better separability criteria using LDA-based methods in a layered manner. This technique is intensive to both Small Sample Size (SSS) and large face variation, due to light or face expression, by optimizing separability criteria.

In contrast to existing techniques that use feature extraction, linear discriminant analysis (LDA) is applied in a layered manner to extract the most similar pattern from a large dataset of facial images, by finding the best projection onto a feature vector. In accordance with various exemplifications, fuzzy rules such as based on Euclidian distance may be applied to the LDA results to reduce the dataset to a smaller subset. These steps may then be repeated to further reduce the subset, until an individual image is identified, or all images are eliminated. The present systems and methods decrease False Acceptance Rate (FAR) by reducing the face dataset to very small size through Multilayered Linear Discriminant Analysis (ML-LDA).

Although the computational complexity at recognition time is more than conventional PCA and LDA algorithms, due to computation of weights at run time, the present ML-LDA provides significant performance gains, especially with respect to similar face databases and SSS problems. In particular, ML-LDA is computationally complex as compared to previous methods because creating of new adaptive database and re-computation of feature space is performed at classification time. Secondly, LDA is performed at least twice, and oftentimes, three or more times, at the time of classification. This makes ML-LDA more computational complex, but on the other hand, FAR is minimized to a negligible level by performing the present ML-LDA. However, ever-decreasing computing costs and decreasing prices for computer memory, data storage, and or the like, coupled with the importance of accurate security screening techniques, such as may be facilitated by the present systems and methods, justify such added computational complexity.

Particular examples discussed herein use a multilayer approach to the application of LDA-based techniques to facial recognition. However, the present invention is also applicable on other pattern recognition applications and methods, i.e. PCA-based, IDA-based, DLDA-based, etc.

Many of the methods and systems and programs may be executed or implemented in a computing environment capable of implementing the systems and methods described herein, according to one exemplification. A computing device can function as a server, a client, a worker node, or any other computing entity. Computing device can be any of a wide variety of computing devices, such as a desktop computer, a notebook computer, a server computer, a handheld computer, a work station, and/or the like.

The computing device includes one or more processor(s), one or more memory device(s), one or more interface(s), one or more mass storage device(s), one or more Input/Output (I/O) device(s), and a display device all of which are coupled to a bus. Processor(s) include one or more processors or controllers that execute instructions stored in memory device(s) and/or mass storage device(s), such as one or more programs implementing process. Processor(s) may also include various types of computer-readable media such as cache memory.

Memory device(s) include various computer-readable media, such as volatile memory (e.g., random access memory (RAM)) and/or nonvolatile memory (e.g., read-only memory (ROM)). Memory device(s) may also include rewritable ROM, such as Flash memory.

Mass storage device(s) include various computer readable media, such as magnetic tapes, magnetic disks, optical disks, solid-state memory (e.g., Flash memory), and so forth. Program implementing process may be stored in such mass storage. Data, such as one or more databases of facial images, such as discussed above, may also be stored on mass storage device(s). One mass storage device may be a local hard disk drive, which may store program and/or database. Various drives may also be included in mass storage device(s) to enable reading from and/or writing to the various computer readable media. Mass storage device(s) include removable media and/or non-removable media and/or remote drives or databases accessible by system.

I/O device(s) include various devices that allow data and/or other information to be input to or retrieved from computing device. Example I/O device(s) include cursor control devices, keyboards, keypads, microphones, monitors or other display devices, speakers, printers, network interface cards, modems, lenses, CCDs or other image capture devices, and the like. For example, a probe image may be input to system via a CCD-based camera or the like for use by system implementing process, such as via a request entered into a keyboard by a user of system.

Display device optionally is directly coupled to the computing device. If display device is not coupled to device, such a device is operatively coupled to another device that is operatively coupled to device and accessible by a user of the results of the method. Display device includes any type of device capable of displaying information to one or more users of computing device. Examples of display device include a monitor, display terminal, video projection device, etc.

Interface(s) include various interfaces that allow computing device to interact with other systems, devices, or computing environments. Example interface(s) include any number of different network interfaces, such as interfaces to local area networks (LANs); wide area networks (WANs), wireless networks, and the Internet. Other interfaces include user interface and peripheral device interface.

Bus allows processor(s), memory device(s), interface(s), mass storage device(s), and I/O device(s) to communicate with one another, as well as other devices or components coupled to bus. Bus represents one or more of several types of bus structures, such as a system bus, PCI bus, IEEE 1394 bus, USB bus, and so forth.

For purposes of illustration, programs and other executable program components, are discrete blocks, although it is understood that such programs and components may reside at various times in different storage components of computing device, and are executed by processor(s). Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 31:
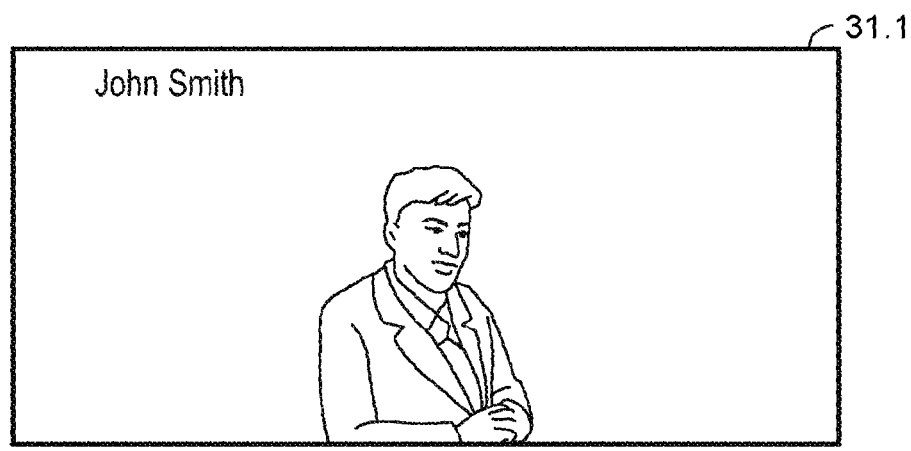
FIG. 31 illustrates an exemplification of an image of a participant displayed together with participant information for the participant.

FIG. 31 illustrates an exemplification in which an image of an individual is displayed on display device 31.1. Information for the participant may be displayed together on display device 31.1 substantially simultaneously with the image of the participant (e.g., the information may appear to be displayed at the same time as the image of the participant). In this exemplification the participant information may include a name of the participant (John Smith). In some exemplifications, a participant (or other entity) may indicate the extent of the participant information to display. For example, a participant may specify that the extent of the participant information displayed should only include their first and/or last name.

Multiple participants (or a single participant) may be displayed on display device 31.1, and patient information for the participant(s) may be displayed together on display device 31.1 simultaneously or substantially simultaneously with the images of the participant(s). In some exemplifications, the participant information for the participants may be displayed proximally to the respective images of the participants to which the participant information corresponds.

Displaying the various portions of participant information proximally to the corresponding participants may visually associate the portions of participant information with the respective participants, thus enabling viewers at the local endpoint to ascertain which portions of participant information corresponds to which participants.

Figure 32:
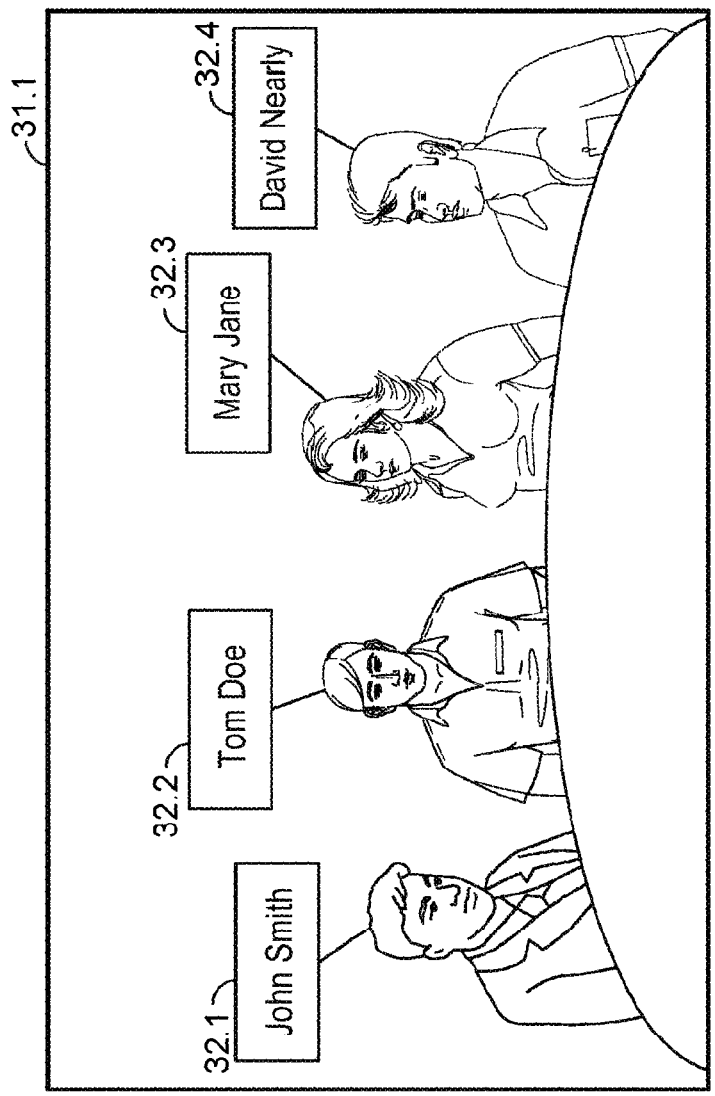
FIG. 32 illustrates a callout box displayed proximally to each participant on a display screen.

The different portions of participant information may be displayed in various ways such that the portions of participant information may be visually associated with their corresponding participants. For example, FIG. 32 illustrates an exemplification in which the device displays a callout box 32.1, 32.2, 32.3, 32.4 proximally to each participant. Each callout box 32.1, 32.2, 32.3, 32.4 may display a name of the respective participant. This may allow the viewers at the endpoint to identify the participants by looking at the callout boxes 32.1, 32.2, 32.3, 32.4 displayed proximally to the respective participants.

Figure 33:
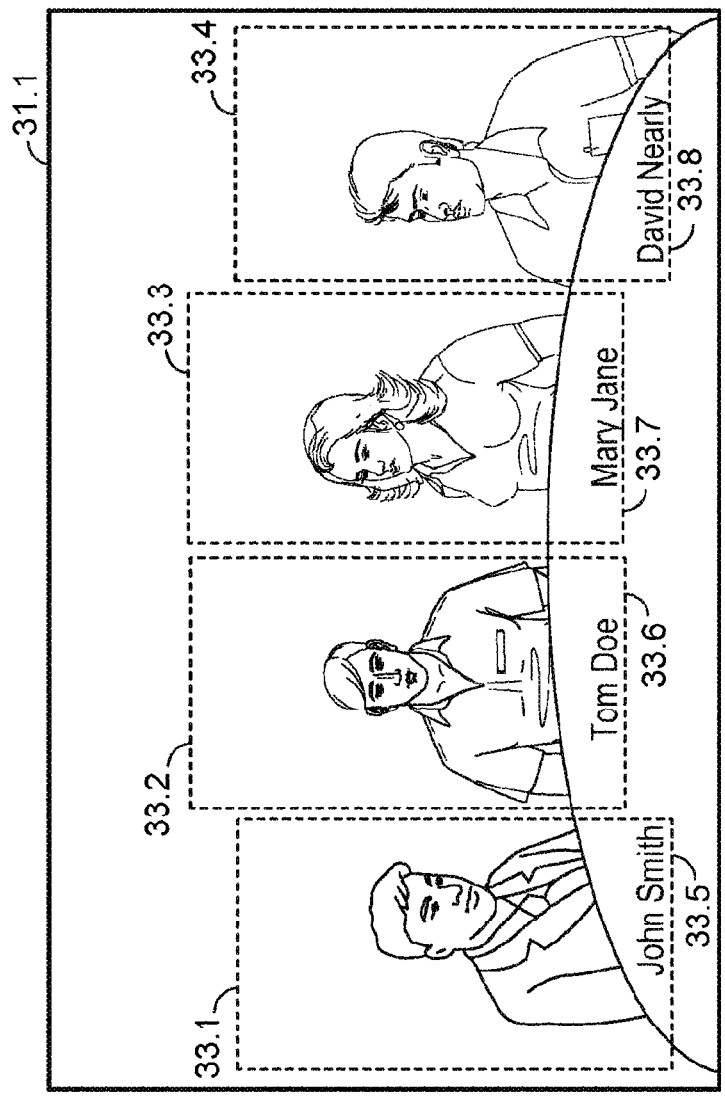
FIG. 33 illustrates multiple portions of participant information displayed simultaneously with images of different participants.

FIG. 33 illustrates an exemplification in which multiple portions of participant information may be displayed simultaneously or substantially simultaneously with images of different participants. In this exemplification, the portions of participant information are visually associated with their corresponding participants by displaying a box 33.1, 33.2, 33.3, 33.4 around each participant and displaying the name 33.5, 33.6, 33.7, 33.8 of each participant within each respective box 33.1, 33.2, 33.3, 33.4.

Figure 34:
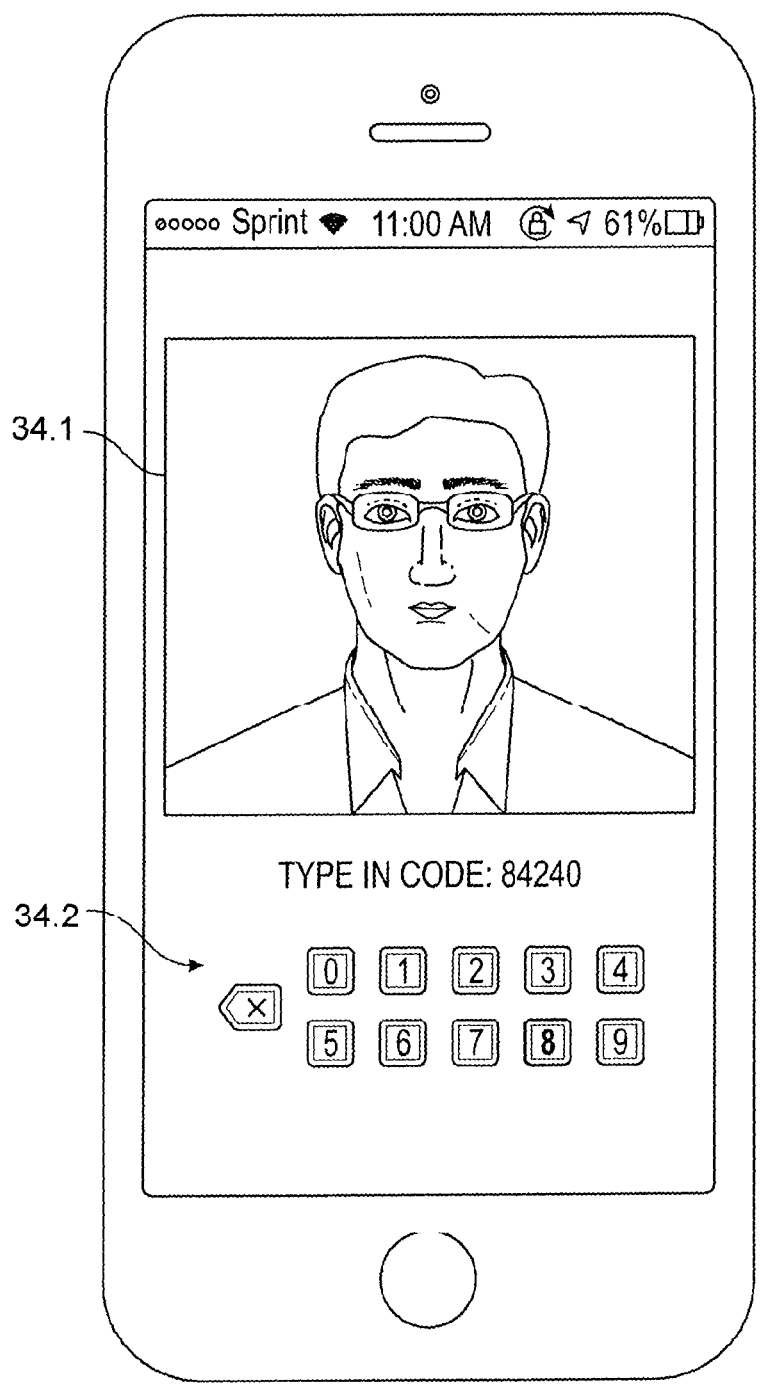
FIG. 34 depicts an illustrative illustration relating to facial recognition.

FIG. 34 illustrates a facial detection screenshot in accordance with the present application. Screen 34.1 illustrates a non-smiling face/pose in accordance with the present application. Secondary verification method 34.2 is also shown as an activation sequence.

Figure 35:
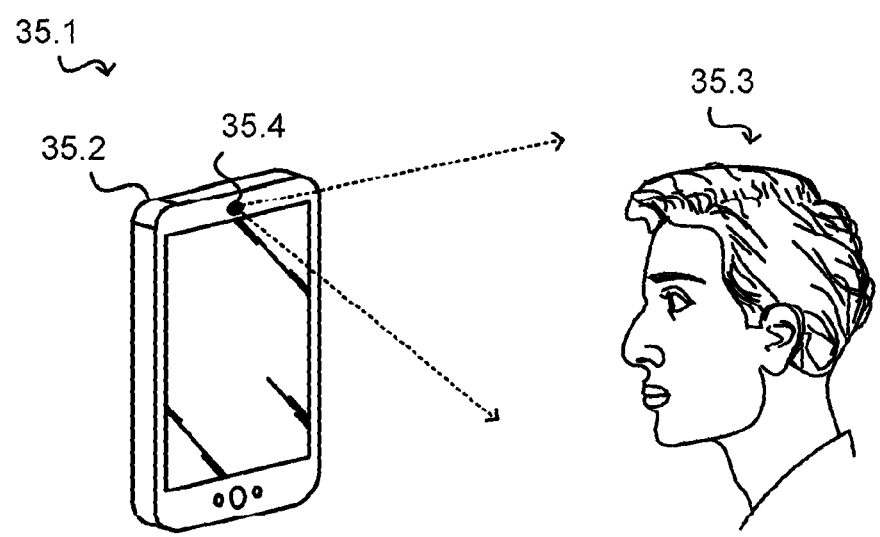
FIGS. 35, 36 and 37 illustrate an example of a computing device detecting an artificial representation of a human face in an image based on changes in facial skin color, in accordance with various exemplifications.
Figure 36:
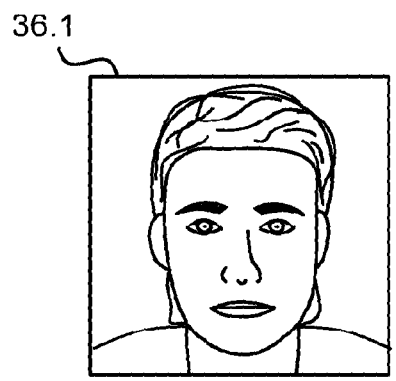
Figure 37:
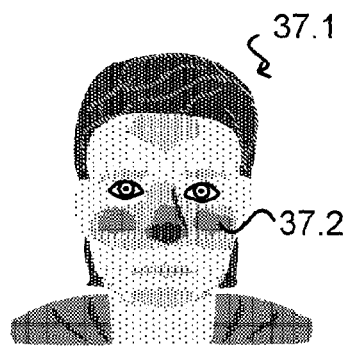

FIGS. 35, 36, and 37 illustrate an example 35.1 of a computing device detecting an artificial representation of a human face in an image based on changes in facial skin color, in accordance with various exemplifications. In FIG. 35, the computing device 35.2 (e.g., mobile phone) having a front-facing camera 35.4 can use facial recognition to identify the user 35.3 of the device and to grant access to one or more functions of the device 35.2, as previously described. In various exemplifications, however, it is also desirable to prevent unauthorized users from using an artificial representation, such as a picture 36.1 to gain access to the device 35.2. In the illustrated exemplification, the computing device can detect one or more changes in facial skin color (e.g., shade, tone etc.) and use the information about the skin color changes to determine when an artificial representation of the human face has been placed in front of the camera 35.4 of the device 35.2. This approach may detect both two dimensional (2D) artificial representations (e.g., pictures, photographs) and three dimensional artificial representations (e.g., face mask).

In accordance with an exemplification, the computing device captures two or more images over a period of time, where each image contains data corresponding to a human face, or a portion thereof. The image data may be a result of a real user's face 35.3 or an artificial representation of a human face 36.1 placed in front of the camera. The computing device 35.2 can detect subtle changes in facial skin color by performing a signal analysis (e.g., Eulerian signal analysis) of the image data in the several images captured by the camera. In one exemplification, the device compares the several images to determine whether any changes in color, tone and shade are present between the two or more images. As illustrated in FIG. 36, multiple sequential images of the same artificial representation of a human face 36.1 will contain no changes in the facial skin color between the images. The image 37.1 of FIG. 37, however, illustrates changes in facial skin color 37.2 that ordinarily occur over time due to breathing, blood circulation, pulse rate and the like. For example, the red values of a human face can vary with the pulse cycles as the amount of blood flow to the face varies. While this variation may be too subtle to be noticed by the human eye, some digital cameras of a computing device 35.2 can be sensitive enough to detect the variations in skin color. These variations then can be used to verify that captured image information reflects an actual person, and not an artificial representation of a person placed in front of the camera.

In the illustrated exemplification, if no changes in facial skin color 37.2 are detected between a predetermined number of images (e.g., 2 or more images), the device 35.2 may deny access to the user based on the assumption that the images contain data for an artificial representation of a human face. If facial skin color changes are detected, however, the computing device 35.2 can enable the user 35.3 to access the device.

Smartwatches, as discussed above, can be used in different areas to perform different functions usually performed by computers or similar electronic devices. Some smartwatches can be used in different industries, such as chiropractic, physical therapy, occupational therapy, physical rehabilitation, sports medicine, and athletic training. Such smartwatches allow users to track complex motions requiring the use of motion sensors such as gyroscopes, accelerometers, compasses, and pressure sensors, fusing the sensor outputs into a single and accurate data stream for use as input commands in consumer electronics devices, and ongoing run-time calibration to ensure an optimal user experience.

One area in which smartwatches can be utilized is the area of physical therapy or therapeutic rehabilitation. In therapeutic rehabilitation, clinicians instruct patients through a therapeutic exercise routine, which routine is created by a licensed clinician to treat a patient's condition. Routines can include a list of therapeutic exercises, manual therapy techniques, modalities, as well as numerous other treatment procedures. During an initial patient visit, the clinician generally instructs the patient through the exercises, displays the exercise techniques, and/or follows the patient through the therapeutic exercise routine. On subsequent visits, the patient will need to recall treatment exercises or ask the clinical staff what the next scheduled treatment procedure is. If there are any changes or issues, the patient must alert the clinician who will then explain, demonstrate, and/or watch the patient perform the new exercise.

However, there are a number of problems, obstacles, or issues with current physical therapy procedures, especially with respect to treatment procedure and workflow in the areas of chiropracty, physical therapy, occupational therapy, physical rehabilitation, sports medicine, and athletic training. These problems decrease efficiency and accuracy of treatment, and increase patient wait time. One problem is that the patients do not know or cannot recall the treatment exercises, therapeutic exercises, and/or other therapeutic treatments, and/or cannot recall the order in which such exercises and/or treatments should be performed. For example, if a patient is assigned three or four therapeutic exercises to be performed sequentially, it is easy for the patient to forget how to perform the individual exercises and/or the order in which they are to be performed. Consequently, the patient can hinder the therapy by incorrectly performing the exercises and/or performing them in the wrong order.

One way to address the problem of incorrect performance of the therapeutic procedures is for the patient to receive additional assistance from a clinician. The clinician may stay with the patient throughout the therapeutic session to instruct the patient on each exercise by telling the patient what the next exercise is and the parameters for performing the exercise, such as the proper form, what weight(s) to use, the number of repetitions and sets, and what the rest periods are. However, such an approach is impractical, especially if the clinician is working with multiple patients. Most clinicians usually provide basic instructions to a patient to complete a therapeutic program, and then assist other patients or perform other tasks in the clinic while the patient completes the therapeutic program. Staying with a patient and monitoring the patient's performance throughout a therapy session is therefore a rather inefficient use of the clinician's time.

As an alternative, many clinicians will instruct a patient regarding the exercise or exercises to be performed, then leave the patient to complete the exercise(s) alone. The clinician will then check in periodically with the patient to check if the patient needs assistance and/or is performing the therapeutic program correctly. While this approach does not take as much time as directly monitoring the entire therapeutic program, it is still quite inefficient. The clinician checks in with the patient as the clinician is able to do so, rather than when the patient completes an exercise or when the patient needs assistance. If a patient is doing an exercise correctly and/or is not finished with the exercise, then the clinician wastes time checking in on the patient. In addition, if the patient is performing an exercise incorrectly, the clinician may not be present at the right time to detect the error, thereby hindering the patient's recovery and lessen the therapeutic benefit. Further, if a patient needs assistance, the patient must wait until the clinician arrives before proceeding further, which wastes the patient's time and could possibly hinder the effectiveness of the therapeutic program. In situations where the clinician knows that the patient requires further instruction, sometimes the clinician will instruct a patient to complete an exercise, then wait for further instruction from the clinician. In this scenario, often the clinician has to estimate when a patient will complete an exercise to determine when the clinician should return to provide further instruction. If the clinician returns before the patient has completed the exercise, then the clinician's time is wasted. On the other hand, if the clinician returns some time after the patient has completed the exercise, then the patient's time is wasted. In addition, it may be possible with some therapeutic programs to promptly move to the next exercise, so an extended interruption of the program while waiting for the clinician may be undesirable and should be avoided. Furthermore, time wasted on individual patients and/or by individual clinicians can have a cumulative effect on the overall efficiency of a clinic, thereby generating a higher per patient operating cost.

Aside from the implementation of therapeutic programs and the waste of time related thereto, there are also issues that arise in the proper execution of the therapeutic programs. In some instances, a selected exercise or exercises may either be too difficult or too easy for the patient to perform. Exercises that are too difficult could possibly injure a patient or discourage proper and consistent effort in therapy, whereas exercises that are too easy may not produce the desired therapeutic effect. Unfortunately, such information can only be obtained by interaction between the clinician and the patient, usually during the actual exercise, at which time the clinician is usually not present, as discussed above. The clinician is therefore usually not aware whether the patient is having difficulty with exercises, or is finding them to be too easy. Optimal therapeutic treatment is hindered until an adjustment of the exercise is performed, which may require the clinician to inefficiently check in on patients more frequently, or require the patient to interrupt the treatment until assistance is provided.

While the clinician usually performs adjustments of a therapeutic exercise, in some instances the patient may adjust the weight of the therapeutic exercise, depending upon how easy or difficult the exercise is. Since such an adjustment occurs during the exercise, the adjustment may possibly not be recorded in the patient's records. The clinician may forget the adjustment that was performed, or may not be aware of the adjustment if it is performed by the patient. The therapist may want the patient to progress but becomes too easy to instruct them on the progression. As a result, the wrong weight may be instituted in the future, which again could reduce the effectiveness of the therapy and waste valuable time in repeating the adjustment.

Aside from adjustments that occur during the procedure, adjustments can also be made based on the progress of the patient in the overall therapeutic process. For example, if a patient is not experiencing an improvement in health in accordance with the overall treatment plan, it may be necessary to adjust the parameters of the plan to achieve the desired result. As another example, if a patient is experiencing an improvement in health that is faster than expected, the clinician may wish to accelerate the time line of the overall plan. However, such adjustments are usually based on interaction between the patient and the clinician, which can result in inaccurate information being recorded, and/or the accidental omission of information from the patient's record. In such situation, a patient may inadvertently continue in a treatment or exercise program that is inefficient and/or does not produce the desired result.

Another component of many therapeutic exercises is the incorporation of a rest period in between exercises. However, some patients either forget to rest or simply ignore the instruction to rest between exercises, which could hinder the therapeutic effectiveness of the exercise, and possibly cause injury. Again, since the clinician is not always present during the performance of the exercises, the clinician cannot instruct the patient to rest, and routine checks of the patient for this reason would be inefficient.

Other inefficient processes in the clinic environment can also waste time and money. One inefficiency is that the clinician has to go to a computer or mobile device to manually enter a patient's treatment results. Another inefficiency is that all treatments have to be manually logged into the electronic medical record, or EMR. These inefficient processes can be especially problematic in a large clinic, simply because the distance from one area to another can be substantial. One other inefficiency can be in billing, because clinicians often tend to estimate the total time for therapy exercises. Inaccurate estimates could possibly lead to loss of billable time, which could translate into a substantial amount of lost revenue over an extended period of time or inadvertent fraudulent billing.

A smartwatch system and method according to the present application can be used to address some of the inefficiencies and/or deficiencies in current approaches for therapeutic treatment of patients in a clinic. The present application proposes to address these inefficiencies using an individual information device, such as a smartwatch (also referred to as a "watch") or similar device, as part of an electronic monitoring and communication system. As discussed above, one of the inefficiencies is that the patients do not know or cannot recall the types and proper execution of the treatment exercises, therapeutic exercises, and/or other therapeutic treatments, and/or cannot recall the order in which such exercises and/or treatments should be performed. The clinician can personally instruct the patient regarding the parameters of the treatment or exercise protocol, but this is also an inefficient use of the clinician's time, so it is preferable to leave the patient to perform the treatments or exercises. However, this means that the clinician is not always present to personally verify that all parameters of the treatment or exercise protocol are being properly performed or achieved, and thus is not able to always be aware of any problems with the performance of the protocol. To address these problems, according to one exemplification, an individual information device, such as a smartwatch or similar device, can be assigned to each patient in a clinic. The information device can contain information specific to the patient's treatment or exercise procedure or protocol. The information device can be used to assist or guide the patient through the treatment or exercise protocol, such as, but not limited to, the name of each treatment or exercise, written, photo or video representation and how to properly perform each treatment or exercise, the number of repetitions for each treatment or exercise, the sets of repetitions, the order of the treatments or exercises, changes to one or more treatments or exercises, additions to or deletions from the overall program, and durations and occurrences of prescribed rest periods. In addition to the information device, a movement tracking device, such as a gyroscope and/or accelerometer, can be worn on one of the extremities of a patient, such as wrists or ankles depending on the nature of the treatment or exercise procedure, in order to track performance of the treatment or exercise. The tracking device can communicate wirelessly with the information device. The tracking device can detect actual performance of the repetitions and/or sets of the exercise procedure, and then communicate such information to the information device in order to inform the patient of success or failure in completing the prescribed treatment or exercise. In this manner, the patient is instructed as to the proper performance of the treatment or exercise protocol without the need for the clinician to be present or to periodically check in on the patient to personally monitor and verify the performance.

Some other inefficiencies are that the clinician might not realize when the patient is ready for instruction, or that further instruction is needed, or that the patient has completed a protocol or program. The information device assigned to the patient can be linked to an overall electronic monitoring and record-keeping system to provide information on the patient's progress. If a patient needs assistance in order to proceed further, the patient can request such assistance via a digital and/or electronic and/or electromechanical interface of the information device, or the information device can send out a message that the patient is ready for instruction as part of the exercise protocol. The information device can also provide information that all or a portion of the exercise protocol has been completed. A notification can then be sent to a personal electronic device, such as a smart phone or smartwatch or similar device, of the clinician to provide such information. In addition, if the patient does not rest for the prescribed rest period, the information device will count down the prescribed rest periods and alerts when the next set and/or exercise is to begin. This gives the patient the needed time to recuperate during exercise regimens. The patient can be instructed regarding the rest periods, and the clinician can be alerted in the patient is not resting appropriately. In this manner, the clinician can be quickly and efficiently made aware of the needs of a patient without having to periodically check on the patient.

Also as discussed above, the overall treatment or exercise programs, or portions thereof, often must be adjusted or changed, before, during, or after the patient visit, in order to achieve the most efficient and effective treatment of the patient. By using the information device, the patient can request immediate assistance from the clinician if an exercise is not having the desired effect, such as, for example, being too easy or too hard. In addition, any changes in the exercise program can be entered into the information device and thereby immediately recorded and stored in the electronic database, rather than relying on the clinician to record such information. Also, by automatically recording the patient's actual performance of the treatment or exercises, the clinician can review the records between and during visits to verify if the exercises are being performed appropriately. The clinician can then make adjustments or changes to the treatment or exercise plan as desired, which will then be stored for the next time that the patient comes in for a visit. By electronically storing these adjustments or changes, they can be automatically retrieved and implemented when the patient arrives for the next visit. Finally, the clinician can more efficiently consult with the patient because instead of the clinician having to go to a computer or mobile device to manually retrieve patient record, the clinician can access the patient's information device and quickly and instantly retrieve the patient's records for the session from the electronic system.

In addition, as discussed above, clinicians often estimate the total time for therapy exercises, which can affect the billing process. Since the information device walks the patient through the exercise treatment, and counts down each exercise rep, set and rest time between, an extremely accurate record of the time that expired during the therapeutic session can be automatically obtained and recorded in the EMR. Such an approach eliminates any estimation errors, and thus results in much more accurate billing.

According to at least one possible exemplification of a treatment method, a patient first arrives in a clinic for a treatment session. The patient then signs in or registers at the reception area. If the patient is not already registered in the clinic's EMR system, the office staff enters the patient's data into the EMR system using EMR software. Once the patient is registered or signs in, the office staff marks the patient as arrived in the EMR. The office staff then assigns the patient to a clinician or a clinical work group, using the app, if the patient is not already assigned to one. The clinician or clinical work group (C/WG) is the clinical staff assigned to patient's care. The office staff will then verify that a treatment protocol is assigned to the patient. If no treatment protocol is assigned, the office staff will send an alert to the clinician, who will then make or select a treatment protocol by creating a flowsheet, which is a list of physical therapy treatments or exercises in the numeric order that they are to occur during the visit. Once a protocol is assigned, or if already set, the office staff will scan a matrix barcode, such as a QR Code™, or similar identification label or structure of an information device, such as a smartwatch or similar device, and/or a tracking device, such as a gyroscope or accelerometer, to upload the patient's template on the device and assign the patient to the given clinician or clinical workgroup. The smartwatch and/or gyroscope/accelerometer is then given to the patient to wear. Activation is sent to the server and the smartwatch is paired with the system. The server then sends an alert to the clinician or clinical workgroup that the patient is in the waiting room.

As an alternative, several smartwatches can always be paired to the server. Each smartwatch is given an identification name and/or number. When a patient is ready for therapy, a smartwatch is assigned to the patient, and the identification name and/or number is matched to the patient. When the therapy session is complete, the smartwatch is removed from the patient's electronic record, but remains paired to the server or system.

Next, one or more of the clinical staff greets the patient and instructs the patient regarding the first treatment procedure. The smartwatch will display the first treatment procedure. Once ready, the patient chooses an appropriate instruction, such as "start" or "help," on the smartwatch. If the patient chooses "start," the smartwatch displays the first treatment procedure and exercise to begin. The patient then goes to the first station for the first treatment procedure or exercise.

At the first station, the patient scans a matrix barcode or similar identification tag located at the station with the smartwatch. The pre-loaded exercise or treatment protocol is then displayed on the smartwatch, or possibly on a video display at the station in another possible exemplification. The displayed protocol includes the name of the exercise and the prescribed number of repetitions (reps) and sets. The patient then selects "start/help" on the display. Upon choosing "start," the patient begins the exercise while the smartwatch counts the prescribed number of reps. Once a set is complete, the smartwatch will alert the patient by a series of vibrations. The smartwatch will then display a rest time count down. If all sets are not complete for a given exercise, the smartwatch will start over and begin counting the prescribed number of reps until the exercise is complete. Once the exercise is completed, the smartwatch will initiate another exercise—if additional exercises are part of the scheduled program—by displaying the name of the exercise, the reps, and the sets from the protocol. The smartwatch will also vibrate and alert the patient it is time to start the next set. If no other treatment or exercise is available or part of the program, then therapy exercises would be complete.

During this process, the server pushes all exercises and rest times as per pre-created/selected protocols to the smartwatch upon initial pairing. If a new exercise is added by the clinician during the patient's appointment or a session, an alert will be sent to the patient that a new exercise has been added, and that the clinician will be with the patient shortly to provide instruction and/or assistance. A corresponding push notification will be sent out from the central server or system to the clinician's mobile device to remind or instruct the clinician to go and consult with the patient regarding the new exercise.

In one exemplification, a motion tracking device, such as a gyroscope and/or accelerometer, can be worn on an ankle of the patient if treatment of a lower extremity is required. This device will wirelessly communicate with the smartwatch. Once a therapeutic exercise is complete, the gyroscope/accelerometer device will transmit such information to the smartwatch, and then the smartwatch will display the next set/exercise. The gyroscope/accelerometer device could be built into the smartwatch, which will be worn on the wrist, if treatment of an upper extremity is required. Alternatively, the gyroscope/accelerometer device could be used in both lower and upper extremity treatments.

After performing the preceding steps to upload the exercise, the patient is ready to begin the exercise. For an upper extremity exercise, i.e., an arm or shoulder exercise, the patient wears the smartwatch on the arm, such as on the wrist or forearm, or possibly the upper arm. The smartwatch can be designed to include gyroscope/accelerometer device, and thus the smartwatch can be used to count the number of reps for the exercise. Meanwhile, a control display is shown on the smartwatch, which will be discussed further herein. After the set of reps is completed, the smartwatch vibrates to alert the patient to stop. The smartwatch then displays and counts down a rest period. After the rest period, the smartwatch starts another set of the exercise as needed according to the program. Once the all sets of the exercise are completed, the smartwatch either initiates the next exercise, or indicates that all exercises are complete. The preceding steps can also be used for a lower extremity exercise, except that the gyroscope/accelerometer device worn on the lower extremity counts the number of reps for the exercise and then wirelessly sends or pushes the information to the smartwatch.

If the patient is performing a series or set of exercises, the server can monitor the patient's progress and notify the clinician after the next to last exercise that the patient is finishing up. Before commencement of a treatment or exercise, the smartwatch displays two options: "start" or "help." Choosing "start" will begin the exercise, whereas choosing "help" will alert the clinical staff that the patient needs assistance. It should be noted that the terms or phrasing of the choices, the number of choices, and/or the types of choices available to the patient at any time before, during, or after a therapeutic procedure, could be different in different exemplifications, and could be customized to meet the particular needs of a clinical environment, and thus are not limited to any of the specific, exemplary descriptions provided herein.

At any time a patient can press the "help" button or select the "help" option, and the clinical staff will be immediately alerted that the patient needs assistance. During execution or performance of a treatment or exercise, the smartwatch will display three options: "too easy," "too hard," and "help." If a patient selects the "too easy" option, the smartwatch sends a signal to the server that the given exercise is too easy. The server will then send a message back to the smartwatch, such as "increase to next level," to instruct the patient. In addition, a push notification could also be sent to the clinician that a change in the exercise has been requested or initiated by the patient. From there the patient can start performing the exercise at the increased resistance or higher level of difficulty, or press "help" to request assistance from the clinician. If a patient selects the "too hard" option, the smartwatch sends a signal to the server that the given exercise is too hard. The server will send a message back to the smartwatch, such as "decrease to lower level," to instruct the patient. In addition, a push notification could also be sent to the clinician that a change in the exercise has been requested or initiated by the patient. From there the patient can start performing the exercise at the decreased resistance or lower level of difficulty, or press "help" to request assistance from the clinician.

In addition, if "help" is selected during execution of the exercise, the smartwatch will send a signal to the server. The server will then send a high priority alert to the assigned clinician or clinical workgroup's mobile device notifying them that a named patient requires help on a named exercise along with the patient's location. The server also will send a message to the smartwatch, such as "please wait, your clinical workgroup will be right with you," to instruct the patient to wait for the clinician or staff member to arrive. The clinician will have the capability to track and record patient heart-rate, oxygen saturation and blood pressure levels. Minimum and maximum levels will be set either by automatic calculations or predetermined numbers set by the clinician. If a patient falls below or exceeds a predetermined target rate zone, the clinician/workgroup will be notified. The clinician can then directly interact with the patient to determine what assistance is required. If the treatment or exercise routine needs to be re-evaluated and/or changed or adjusted, the clinician will be able to scan the matrix barcode tag on either the smartwatch or the gyroscope/accelerometer device to pull up the patient's flowsheet. The clinician can then make changes to the patient's program by choosing from a number of options, such as "skip/delete/edit," on the clinician's mobile device. The clinician could choose to skip a particular exercise, delete a particular exercise from the overall program, or adjust one or more exercises as desired by changing parameters of the exercise, such as increasing or decreasing weight, resistance, reps, and/or duration. The changes made and/or approved by the clinician are then saved to the server and sent to the smartwatch to provide the patient with an updated or adjusted exercise program.

The smartwatch devices disclosed herein can be used in conjunction with an app in a clinical setting. The electronic patient processing device and a method of using the electronic patient processing device is used to service the physical therapy industry, but has crossover application in chiropracty, occupational therapy, physical rehabilitation, sports medicine, and athletic training. It should be noted that the devices and methods disclosed herein will be discussed primarily as they relate to the field of physical therapy, and the use of the devices and/or performance of the methods by physical therapists. However, it should be understood that the devices and methods disclosed herein may be used in many different professional fields or technological areas, and thus the devices and methods are not limited to only physical therapy, and any discussion herein relating to physical therapy should be understood as encompassing other different professional fields and technological areas. Also, the persons using the devices and/or practicing the methods may include other personnel in the field of medicine besides physical therapists, such as doctors, nurses, clinicians, licensed practitioners, medical assistants, physician assistants, or other physical therapy clinic or medical staff. Further, the persons using the devices and/or practicing the methods may include other personnel in different professional fields and technological areas besides physical therapy, as mentioned above. Therefore, any discussion herein relating to physical therapists should be understood as encompassing other different personnel in the field of medicine, or personnel in different professional fields and technological areas besides physical therapy or medicine.

Most physical therapy clinics take the form of a gymnasium or gym, a large hall, or similar building. The clinic contains physical therapy tables and other equipment located in either individual rooms or in a common area. For example, each room could contain a physical therapy table for some type of a static treatment, which treatment could include application of ice or cooling packs, application of hot or heating packs, and/or electro-stimulation. Such treatments are generally timed, so each table and/or room is generally equipped with a countdown timer. In these or other rooms or areas, a patient may perform exercises, which are set to a number of repetitions (reps) or to a specific time. It is the responsibility of the physical therapist to monitor each individual therapy session. Physical therapy clinics can range in size from a small gym with a few or several rooms or areas, such as approximately three to ten, to a large gym with many rooms or areas, such as approximately 30 to 50, or possibly even more. As a result, a physical therapist on a busy day may have several to many rooms with patients that he must monitor at one time or in overlapping therapy sessions.

This application relates primarily to a computer program for computers, internet or web-based computing, and mobile computing on mobile devices, such as smartphones, smartwatches, and other mobile devices. The program or software or computing application will be referred to herein as an "app." The present application therefore relates to an app, a server which hosts the information accessed by the app, and a server portal from which that information can be accessed. The phrase "mobile devices," as used herein, refers to any and all mobile devices including, but not limited to, such devices as smart phones, cellular phones, mobile phones, pagers, portable or mobile computers, laptops, personal data assistants (PDA), handheld computers, mobile internet devices, tablet computers, wearable computers, calculator watches, smartwatches, and head-mounted displays.

The app is designed to address different problems that often occur within physical therapy clinics and related areas. A first problem relates to notifying the physical therapist in a timely and effective manner that a patient awaiting instruction and/or treatment. In many clinics, when a patient enters the clinic and waits in the waiting room, the clinic staff will communicate the patient's arrival to the physical therapist by taking the patient's medical chart and placing it in a slot outside the waiting room. The inherent deficiency of this method is that it depends on the physical therapist noticing the presence of the chart. Often the physical therapist is extremely busy moving from room to room and from patient to patient. It is not uncommon for the physical therapist to be on the opposite side of the clinic, which again can be very large, and thus he cannot easily see the chart. In other instances, the view of the chart could be blocked by gym equipment or other structures in the clinic. No matter the reason, if the physical therapist does not or cannot see or notice the chart, the patient can experience unnecessarily extended wait times. To compound this issue, many clinics have an exterior waiting room separated from the treatment and exercise areas, which makes it nearly impossible for physical therapists to easily check whether or not one of his patients is in the waiting room.

To address this first problem of undesirable delays, the device and method according to the present application first assigns each patient to a physical therapist. When a patient enters the waiting room, the clinic staff will access the server portal and use the drag n' drop feature or similar interface to place the patient in the server's virtual "waiting room." The server will then send a notification to the mobile device of the assigned physical therapist to thereby notify the physical therapist of the patient's presence in the waiting room. The physical therapist is therefore quickly made aware that the patient is waiting in the waiting room, and thus a potential unnecessary wait, such as 10, 15, or 20 minutes or more, can be substantially reduced to a much shorter time, such as five, three, or one minute or less. In addition to the specific notification regarding a specific patient for a specific physical therapist, the app may also provide a list of all patients in the waiting room. The physical therapist or other clinic staff can thereby view all patients in the waiting room at any time, to even further ensure that all patients are being attended to in a timely manner. The device and method disclosed herein thereby minimizes problems caused by the physical layout of the clinic, the placement and design of the waiting room, or the physical location of the charts on a wall of the clinic.

A second problem is that many clinics require a physical therapist to keep track of multiple patients simultaneously, or at least in overlapping therapy sessions. Such multi-patient monitoring can be difficult, especially since the therapies being performed vary in type and time. To further explain, in most therapy sessions or visits, once the patient is admitted or signed in, he is taken to a therapy room or area by the physical therapist. The physical therapist then commences the therapy session, which could involve a static treatment or the performance of therapy exercises. A countdown timer is often used to set the length of the therapy session to a desired time. Many of these countdown timers are equipped with rather loud alarms to ensure that the physical therapist can hear or notice the alarm, regardless of his location in the clinic. When the countdown timer expires and/or sounds an alarm, the physical therapist or the clinic staff will then visit the patient to either initiate additional therapy or discharge the patient. Since the physical therapist may be responsible for multiple patients, each with his own countdown timer set at a different time, it can become extremely difficult for the physical therapist to keep track of the multiple timers and therapy sessions. A physical therapist will often personally go to different rooms to check the timers in order to plan his next steps and coordinate his assistants. The more patients the physical therapist is treating, the more hectic the work becomes, and the more difficult it becomes to maintain efficiency. Randomly checking timers is an inefficient way to monitor patients, and wastes valuable time that the physical therapist and the clinic staff could devote to other work.

In addition, the unexpected and obnoxious sounding of the alarms makes it difficult for the therapist to effectively treat patients. As many medical professionals know, it can be possible in the treatment process to develop a good relationship with the patient to obtain the most accurate and honest feedback about how the patient is feeling and progressing. However, it can be difficult to develop these relationships if productive conversations are interrupted by shrieking alarms that the physical therapist must rush off to address. In addition, the mere sound of these alarms can be very bothersome to patients trying to relax as part of their treatments. The effectiveness of such treatments may be diminished if the patient is unexpectedly shocked or surprised by a sudden and piercing sound. For example, a patient who is experiencing muscle tightness, spasms, etc., may be prescribed a heat treatment to relax the muscles to relieve pain and improve the effectiveness of therapeutic exercises. However, if such a patient is suddenly frightened by a loud alarm, the patient could instinctively tighten up his muscles in response to the stress of the shocking and unexpected noise. In other situations, a patient may just want to focus on his exercises or enjoy a calm and quiet therapy session, and the loud alarms can be both distracting and irritating.

To address this second problem of inefficient and loud alarms, the device and method according to the present application utilizes a main page that contains a list of all tables, rooms, and therapy areas in the clinic. Each room or area can be assigned a patient and a timer. In this way, the physical therapist can easily reference all of the timers for which he is responsible whenever he wishes. In addition, the app can be programmed to alert the physical therapist some time in advance of the expiration of a timer so that the physical therapist can plan to address the needs of the patient when the timer expires, i.e., when the therapy session is concluded. The alert is sent from the server to the mobile device of the physical therapist. The alert may be in the form of a visual, audible, or tactile signal, such as an alert message, sound, or vibration. In this way, a physical therapist is notified before the alarm goes off, so that he can transition easily between tasks without sudden interruptions of what he is currently doing. Since the alarms can be strictly visual or tactile in the form of messages or vibrations, it is not necessary to use loud countdown timers at any of the room locations or treatment areas. The result is a much quieter and peaceful clinic, which is to the benefit of both the patients and the workers.

A third problem is inefficient communication between physical therapists and clinic staff, especially in large or larger clinics. For example, it is not uncommon for a clinic staff member to conduct a room to room search to try to find a particular staff member or patient in the clinic, such as for the purpose of conducting a conversation, delivering paper work, passing on messages, etc. This approach is inefficient and wastes time. While such a situation could be addressed by staff members utilizing their personal mobile devices to message one another, most workers value their privacy and prefer not to share personal information with their co-workers, or risk being bothered with work-related matters when not at work. Additional to this, messaging about patients on an unsecure app violates HIPAA standards (law).

To address this third problem of inefficient communication, the device and method according to the present application utilizes an app that includes a third party messaging section that allows clinic staff to message one another within the clinic without revealing personal information. The app can be installed on a personal mobile device. The app includes a switch or option to allow a user to disconnect the app from the server, thereby preventing the app from disturbing the user when the user is not in the clinic.

A fourth problem is a general inability for a physical therapist to both perform his work with his patients, while at the same time monitoring and coordinating the work of one or more assistants. In the same way a hectic environment makes it difficult for a physical therapist to organize his own work, a busy work environment also interferes with a physical therapist's ability to coordinate work with his assistants. Keeping track of the patients of one worker alone is difficult. In many states, a physical therapist can have as many as three assistants, and must track the work of all three.

To address this fourth problem of insufficient monitoring and coordination of assistants and clinic staff, the device and method according to the present application utilizes an app that not only allows users of the app to assign a timer to the room of a patient, but also allows a user to assign a timer to himself or another user. When a worker at the clinic takes a patient to a room and assigns that room to the patient and sets a timer for the room in his app, he will also have the option of assigning that timer to another user or himself. When another user is assigned, that user will receive a notification for the timer. Once a user is assigned to a timer, that information appears in the app under that particular room. In this way, a physical therapist can not only assign patients and timers to his assistants or himself efficiently (he doesn't need to track them down), he can also monitor what patients his assistants are working with at any given time to ensure equal distribution of labor.

A fifth problem is that physical therapists often need to set reminders for themselves regarding some aspect of a patient's therapy for the next time the patient comes in for physical therapy. Often the physical therapists have to resort to making mental notes, placing Post-It notes in the patient's file or in their office, or asking clinic staff and/or patient to remind them about the specific issue at the patient's next visit. These methods are all subject to various human errors—forgetting the mental note, losing the post-it note, or being on the opposite end of the clinic from the clinic staff—that are common occurrences that prevent a physical therapist from properly doing his job.

To address this fifth problem of inaccurate or lost reminders, the device and method according to the present application includes a reminder system or component. For example, under each patient's information could be a reminder section or option labeled "'remind me next time" or "reminder" or a similar indicator. To utilize this feature, the physical therapist can type a reminder note regarding the issue relating to the patient's physical therapy that needs to be addressed in the future. The note is then transmitted via the app or similar interface into the server and stored with the patient's records. When the patient visits the clinic the next time, the clinic staff members use the server portal to place the patient in the virtual waiting room and assign the patient to the physical therapist. The server will then access the reminder message and, if appropriate for that patient visit, send the reminder message to the physical therapist. In this way, a physical therapist needs to remember the note as long as it takes to type it into the system, and thus human error is minimized.

A sixth problem is that whenever a patient undergoes surgery and has follow-up physical therapy, the doctor in charge of the operation often has a set of "protocols" for the patient to go through at marked intervals of recovery. Each doctor has a different protocol for each operation, and each protocol has a different waiting period before the protocol may be implemented. Because of this, it can often be very difficult for a physical therapist to know and/or remember which patient has which protocol, and when each patient must progress through said protocol.

To address this sixth problem of tracking post-surgerical protocols, the device and method according to the present application includes a protocol section for each patient. In the portal of the server, users can upload a picture or scan of each doctor's protocols, along with the waiting period for each protocol. Whenever a patient has a surgery, he can inform a member of the clinic and they will input the information with the surgery date. When the protocol's wait-time has expired, the server will send a notification to the physical therapist assigned to the patient at the beginning of the patient's next visit, along with a note, as a description, and/or an image of the protocol itself displayed on the mobile device.

A seventh problem is that physical therapists and clinic staff in a clinic setting are constantly moving around to address patients, often multiple patients at one time. As such, keeping track of tasks can be very difficult as the workload increases.

To address this seventh problem of tracking post-surgerical protocols, the device and method according to the present application includes a "task list" in the app. Each user has his own task list that the user can modify at his own discretion. Users can manually add messages or notifications to the task list. The latter two options allow a physical therapist or clinic staff to keep important information for the clinic within easy reach without cluttering up the notifications on a mobile device.

The app will have similar functionality across different platforms and operating systems. The server will manage data transfer between users, store data relevant to the app usage, analyze user input, and contain a portal to the effect of these functions. Limited messaging will be a part of the functionality as well.

When accessing the app, the user will be able to do a number of functions, which include but are not limited to the tasks discussed in this paragraph. Users can set timers to each room/table in the clinic. Users can access separate lists, such as patients, gym, waiting room, employees, and assign them to the rooms and users. Patients can be added to the gym/waiting room lists or assigned to a room via either app or server. Clinicians can be assigned to patients via app or server. Patient and employee lists can be managed via the server portal. Users can send and receive messages to and from other users logged into the portal. Users can manage a personal task list to keep track of priorities at the work place. Users can manage and display post-surgical protocols, and send notifications to alert clinical staff when progression is prescribed. The app can notify users of new information via the vibration function, with one setting for low priority, such as messages, and one setting for high priority, such as a timer going off or a new patient in the waiting room.

The main page of the app will primarily contain a list of rooms and tables in the clinic. From this page, the user can manage rooms and tables, including assigning patients and timers to the rooms and tables. From this page, the user can also access and manage lists of patients who are in the gym and in the waiting room. View options for the main page can be changed in the settings. For example, the main page can show only active/assigned rooms/tables as a default setting, but can be changed to show all tables or only rooms/tables in the user's work group.

A user can select a room/table to view its information, including the patient assigned to the room, the timer running, the clinician assigned to the room, and treatment details. The chat or messaging function allows users to message one another. The work space page is accessible from the menu. Viewing of all the employees can be organized by alphabetic order, employee title, work group, and work status, such as on duty or off duty. The work status and group status of the employees can be managed via the server portal. The patient list is also accessible from the menu. For example, when the menu page is first accessed, a patient search symbol could be visible, which symbol could be replaced with search results as the user begins typing in a name to search. When a patient's info is accessed, the clinician/work group to whom the patient is assigned could be displayed first, along with any timer assigned, and any notes and/or treatment information the user has entered. Both the patient and employee list information can be stored on the server.

When a message is received, or a timer/room is assigned to the user, or a patient is added to the waiting room by the secretary, a push notification or similar notification or message could be sent to the work group to whom the patient is assigned. The settings panel is accessible from the menu. From this panel the user will be able to access and/or change different information and settings, such as entering their login info into the app, changing user information, changing certain view options, viewing app information, and other settings functions. The menu allows the user to access different menus or lists on the app, such as patients, messaging, workplace, and settings. From the portal, the user has the ability to manage patient and employee lists and the addition of patients from the patient list to the waiting room list, and send and receive messages from users. The server also can be designed to permit analysis of app usage and information relating thereto, such as regarding the length of time patients remain in the waiting room, and the response time of users to assigned timers. The server portal could possibly be designed to automatically manage rooms, timers, etc., although in one exemplification only the app can perform such management functions, whereas the server portal cannot.

The following is a description of how the app may be utilized in a physical therapy setting, although it should be understood that the functions and use of the app are not limited to this specific example. It should also be understood that the terms and menus used to describe parts or sections of the server portal and/or the app are for exemplary purposes only and are not meant to limit the exemplifications disclosed herein. Essentially any equivalent wording to the exemplary terms and phrases disclosed herein may be used in the app. For example, the following description may describe a user accessing a pop-up menu on the application. However, it should be further understood that a drop-down menu or any other similar interface could be utilized in place of a pop-up menu. In other words, well known alternatives could be utilized in place of the parts or components of the system described herein for purposes of example.

In a visit to a physical therapy clinic, a patient first enters the waiting room of the clinic and notifies the clinic staff of his presence. A staff member then checks the system via the server portal or the app to determine if the patient is registered in the clinic's patient database. If the patient is not registered, the staff member selects the "patient" tab or column on the main screen, and then selects "add patient" from a drop down menu. The staff member then enters the patient's information, such as name, date of birth, address, etc., into a pop-up dialogue box. As a possible alternative, the app could be designed to permit the patients themselves to access the app remotely, such as at home, so that the patients can enter their registration information into the app. In this manner, the patient can register as a new patient before arriving at the clinic.

It should be noted that the "menu" button provides access to essentially an overview of the clinic via the main informational sections of the app. For example, when a physical therapist presses the "menu" button on the app, several choices are listed, including, but not limited to, "rooms," "patients," "waiting room," "gym," "messaging," "task list," "settings," and "logout." The "rooms" button, when pressed, returns to the main page while a request is sent to the server for an update on room data. The server sends the information to the mobile device, and the main page now displays the current or updated data for the rooms and tables. The "patients" button switches to the patients page, and again a request is sent to the server for an update on patient data. The current or updated data is then shown on the patients page. Essentially any menu or page that requires the latest or current data can be automatically updated from the server when the menu or page is accessed. The "waiting room" and "gym" buttons switch to pages showing what patients are in the waiting room and the gym, respectively. The "messaging" and "task list" buttons access those features of the app. The "settings" button switches to the settings page. Finally the "logout" button logs the user out of the app so that the user no longer receives notifications or other information, such as when the user is no longer working for the day. More specific information regarding these buttons will be discussed herein below.

In addition to the patient information, the staff member also assigns the patient to a single physical therapist or a therapist group. It should be noted at this time that the therapist group could comprise any number of physical therapists and clinicians who work at the clinic. Assigning a patient to a therapist group may be advantageous since more than one person would be available to address the needs of the patient. For example, a first physical therapist in the group may handle setting up a first patient's therapy session. That first physical therapist may also be scheduled to handle the conclusion of the first patient's therapy session. However, some instances may arise in which the first physical therapist is busy attending to a second patient when the first patient's therapy session is about to conclude. In this scenario, a second physical therapist in the therapist group could promptly attend to the conclusion of the first patient's therapy session, while the first physical therapist continues to attend to the second patient. As a result, all patients receive prompt and uninterrupted care, which improves efficiency and customer service, i.e., quality service and patient care.

Once all of the information for the new patient is entered by the staff member, the data is saved into the clinic's patient database. At this point the process is the same for both new and current patients. First, the staff member has the option of adding a "note" to the patient's information. The note may include many different kinds of specific information, including, but not limited to, information particular to the visit or therapy session, information relating to an ongoing therapy program, changes in a therapy program or in the patient's physical or health status, a reminder relating to scheduled changes and/or updates to the therapy program or session, special information regarding a patient's needs or requests, and other such information. In the case of a reminder or other such previously entered information, the note may already be in the system and thus may be present when the patient is logged in or registered. The notes could be listed in a section entitled "remind me" or "reminders" so that the physical therapist or members of the physical therapy group take care to read the note.

Regardless of whether a note is entered or not, or if a note is already present in the system, the patient is then added to a patient queue to await further processing. This can be done either automatically or by a staff member. When ready, the staff member can use the server portal to move the patient's name, such as by drag and drop, from the queue and into the "waiting room" section of the app. As an alternative, the queue section could be omitted and the staff member could add the patient directly to the waiting room, or the server could execute such a function automatically.

Once the patient has been added to the waiting room, an update is sent out in the form of a push notification from the server to the device(s) of the person(s) responsible for that patient, such as an individual physical therapist or physical therapy group. The patient's name is now listed in the waiting room and visible via the app by all staff in the clinic using the app. In addition, if there is a note present for the patient, the note is also included in the push notification. Otherwise, the push notification simply indicates that a patient has arrived in the clinic and is currently in the actual waiting room of the clinic.

After completion of the preceding steps and placement of the patient in the virtual waiting room, the patient will be sent to the appropriate treatment area in the clinic. The assignment of the patient is based on the type of therapy session. One assignment is to send the patient to the gym to perform exercises, and another assignment is to send the patient to an individual treatment room for static treatment or other physical therapy. The assignment can be performed via the app or the server portal, either by a member of the clinic staff, a member of the physical therapy group, or possibly automatically by the server based on the scheduled therapy.

If the patient is scheduled to perform certain therapeutic exercises, then he is sent to the gym. In most instances, the physical therapist or a member of the physical therapy group assigned to the patient will access the app on his mobile device, select the patient from the waiting room, and then long press on the patient's name to bring up options for the patient. From those options, the physical therapist can select "Gym" to assign the patient to the gym. The mobile device then sends an update to the server to record the movement of the patient to the gym, and the name of the patient then appears on the gym list. Alternatively, a drag and drop system could be used in which the name of the patient is dragged from the waiting room list and into the gym list. The patient is then escorted, either by the physical therapist, a member of the physical therapy group, or a staff member, from the waiting room to the gym to perform the therapeutic exercises. In one exemplification, the app will simply list the patient as being in the gym. In another exemplification, the gym list could include sub-lists or sub-headings indicating specific areas in the gym to which the patient is specifically assigned, which may be advantageous for very large clinics with very large gyms and many therapy machines and areas.

Once the exercises are completed, the physical therapist or physical therapy group member will be notified, such as by a message, alert, or push notification. The physical therapist will then perform any necessary consultation, and then commence the next step in the therapy session. The physical therapist selects the patient's name in the gym list, such as by long pressing on the name in the gym list. A pop-up or similar menu will then appear with a list of choices. One of the choices is "remove patient" or "discharge patient." If the patient has successfully completed the exercises and no further therapy is needed, the physical therapist pushes on the "discharge patient" button. In one exemplification, a pop-up menu or dialogue box will appear with a message requesting confirmation of the discharge, such as by asking "Remove patient from gym?" or "Confirm discharge of patient?" or similar. If the patient is not to be discharged, the physical therapist selects "No" and the message disappears. If the patient is to be discharged, the physical therapist selects "Yes." An update is then sent from the mobile device to the server to record that the patient has been discharged. In another exemplification, the confirmation message can be omitted and the pressing of the "discharge patient" button immediately sends an update to the server that the patient has been discharged by the physical therapist. The clinic staff can then receive a message, alert, or similar notice, or simply note on the server portal that the patient is now listed as discharged or has been removed from the gym list. The clinic staff can then discharge or log out the patient.

If the patient is not to be discharged, one of the other possible choices in the pop-up menu could be an option for additional treatment, such as a "more treatment" button. When this button is pressed, a new menu or list appears with the list of available rooms. The patient can then be assigned to a room for additional treatment. The room assignment process is the same whether the patient is first sent to the gym, or immediately sent to the room from the waiting room. It should be noted that some physical therapy clinics have individual or private rooms, individual tables in a common area, or a combination of both. Thus, any discussion of rooms or treatment rooms herein should be understood as referring to both individual rooms and tables in a common area.

As discussed above, one option when a patient has been registered and placed in the waiting room is to send or assign the patient to the gym for therapeutic exercises. Another option is to send or assign the patient to an individual treatment room or therapy room or therapy table. During a therapy session or visit, a patient may be assigned only gym exercises, only therapy in a therapy room, or both. As discussed above, a patient may first perform exercises in the gym and then receive further treatment in a room. Alternatively, the patient can receive treatment in the room and then proceed to the gym for exercise. Whether the patient is assigned to a treatment room immediately after registration, or after exercising in the gym, the process is the same.

From the main menu, a staff member can drag and drop the patient's name from the waiting room to an empty room in a list of treatment rooms on the server portal. Alternatively, the physical therapist or physical therapy group member can use the app to move the patient from the waiting room to a treatment room. To do so, the physical therapist selects the patient name, such as by long pressing on the patient name in the waiting room list. A pop-up menu or dialogue box appears with a list of empty or unclaimed rooms. The physical therapist then selects one of rooms from the list, and the patient is added to the selected room. Whether initiated by the clinic staff via the server portal or by the physical therapist via the app, the server updates the information and now lists the patient as being assigned to the selected room. The clinic staff or the physical therapist or physical therapy group member then escorts the patient to the assigned room for treatment.

Either before, during, or after the patient is taken to the room, the physical therapist or a physical therapy group member accesses the room functions in the app, such as by long pressing on the room in the list. A drop-down menu or pop-up dialogue box appears with a list of room options. Some possible options include, but are not limited to, "set timer," "clear timer," "reassign room," "reassign therapist," "move to gym," "discharge patient," and "timer answered." Each of these menu choices can be selected and can initiate further pop-up menus or dialogue boxes depending on the function selected. For each of these menu selections, an optional yes/no dialogue box can be included that pops up to confirm whether or not the physical therapist wishes to continue with the particular selection. If "no" is selected, the dialogue box closes, whereas if "yes" is selected, additional dialogue boxes appear for the selected function. Alternatively, the app could be set such that the physical therapist can press either the "back" button on his mobile device, or anywhere on the screen outside of the dialogue box, to thereby exit the selected function.

The "set timer" function allows the physical therapist to set the time for a particular treatment or exercise. For example, the physical therapist may press "set timer," then enter the timer length. As an option, a yes/no confirmation screen can be included that pops up to confirm that the entered timer length is correct. As another option, once the timer is entered, another pop-up menu can be included that inquires if the timer has been assigned to an individual physical therapist or a physical therapy group. As discussed above, the patient should ideally be assigned to a physical therapist or physical therapy group when first registered in the clinic. If an individual physical therapist or physical therapy group has been assigned, then no further action needs to be taken, and the timer information is updated on the server for the selected room. However, if the patient has not been assigned to a physical therapist or physical therapy group, the physical therapist can assign the patient and the room to either himself, another physical therapist, or a physical therapy group. In the case of an individual assignment, the physical therapist can access a list of physical therapists, and then can either select his own name or the name of one of the other physical therapists and assign that name to the room. In the case of a group assignment, the physical therapist can access a list of physical therapy groups and select the desired group. The "set timer" button can also be accessed once a timer has been set to allow the physical therapist to cancel the current timer and set a new timer, or to edit the current timer to add or subtract time. As an alternative, a separate "reassign timer" or "change timer" button could be used strictly for editing the original timer or setting a new timer. A "clear timer" option can be included to allow the physical therapist or physical therapy group member to cancel or clear out a timer, such as in the case of an incorrect timer length or a timer that is no longer needed. After any of the above changes and/or selections, the assignment and timer data is then uploaded to the server.

During or before the therapy session in a particular room, the physical therapist or physical therapy group member or clinic staff can choose to change the room and/or the assigned physical therapist or physical therapy group by selecting the "reassign room" button and/or the "reassign therapist" button from the room function menu. Each of these buttons can access the room list and/or the patient list and/or the therapist list so that the patient can be assigned to a different room and/or to a different therapist. Before, during, or after the therapy session in a selected room, the physical therapist or physical therapy group member or clinic staff can choose to send the patient to the gym for exercise by selecting the "move to gym" button from the room function menu. The gym options are discussed herein above.

Similar to the gym options, another room option would be a "discharge patient" or "clear patient" button or selection. If the patient has completed therapy in the room and no further therapy is required, then the patient can be discharged by the physical therapist by selecting the "discharge patient" option.

The setting and assignment of timers is the most common and important of the room functions. The timer dictates the length of the therapy, which is important to effective therapy, and notifies the clinic staff when the therapy is complete, which is important to patient care and customer service. For example, if no one on the clinic staff is assigned to the timer, a patient may then be left to wait for an undesirable amount of time until a staff member notices that the therapy is complete. As discussed above, once a timer is set, it is either automatically assigned to the physical therapist or physical therapy group previously assigned to the patient, or it can be manually assigned to a physical therapist or physical therapy group. If the physical therapist entering the timer data assigns the patient or room to himself, the information is uploaded to the server. The physical therapist then waits for an alarm or alert to be sent to his mobile device, such as by push notification, some time in advance of the termination of the timer. For example, such an alarm or alert could be sent 30 seconds, one minute, 90 seconds, two minutes, or essentially any amount of time, prior to the termination of the timer. The time is selected based on how much time the physical therapist believes would be sufficient to allow him to go and attend to the patient at approximately the expiration of the timer so that the patient receives prompt attention.

The alert itself can be done by vibration of the mobile device so that the alert is not noisy and disruptive to patient care.

As discussed above, the physical therapist entering the timer data, i.e., the first physical therapist, can assign the timer to another physical therapist, i.e., the second physical therapist, who can be either an individual physical therapist or a member of a physical therapy group. When the first physical therapist assigns the timer to the second physical therapist, a push notification or alert is sent to the mobile device of the second physical therapist. A pop-up menu then inquires whether or not the second physical therapist wishes to accept the timer assignment. If he answers "yes," then the timer is successfully assigned to the second physical therapist and uploaded to the server. The process then proceeds for the second physical therapist in the manner discussed above for the first physical therapist. If the second physical therapist answers "no" to not accept the timer assignment, either the assignment remains with the first physical therapist or is assigned to a physical therapy group, if such is available.

It is not required that a timer be assigned to a specific individual physical therapist, but rather the timer can be assigned to a physical therapy group as a whole. Whether this group assignment is done automatically or manually, the subsequent process is the same. In a similar manner as for an individual physical therapist, when the assigned timer is approaching zero, an alert is sent out, such as two minutes before the timer will reach zero. If an individual physical therapist is assigned to the timer, the alert or alarm only goes to the individual physical therapist. However, if the timer is assigned to a physical therapy group, all members of the physical therapy group receive the alert. At this point it is up to one of the members of the physical therapy group to accept responsibility for the timer and the patient.

When the alert is received, either by an individual physical therapist or the physical therapy group, a response to the alert must be entered into the app. The person(s) receiving the alert will have the option to respond in the affirmative or negative, such as by choosing "I got it" or "I can't", or equivalent phrasing indicating whether or not the person can tend to the patient. Once a physical therapist or other clinic staff accepts the timer, the results are uploaded to the server. Again, the physical therapist accepting the timer may be the physical therapist originally assigned to the timer, or may be a new physical therapist who has agreed to accept the timer assignment, or may be a member of the clinic staff, such as physician's assistants, nurses, etc. In addition, the original physical therapist has the option to reassign a timer that was originally assigned to him in the event that he is unable to attend to the patient when the timer reaches zero.

Once a physical therapist or staff member accepts the timer assignment, the patient and the timer are now the responsibility of that person. Any additional alerts, such as an additional alert at a time closer to the expiration of the timer, or an alert when the timer has expired or reached zero, will only be sent to the person who accepts the timer. Therefore, even if the timer was originally assigned to a physical therapy group, no more alerts will go to the other members of the group who did not accept the timer assignment.

If the physical therapist or a member of the physical therapy group cannot accept the timer assignment for some reason, then that person answers in the negative on the app. If the timer has been previously assigned to an individual physical therapist or physical therapy group member, then it is the responsibility of that person to reassign the timer to another person. In such a situation, the physical therapist or physical therapy group member accesses the options listed for that room on his app and selects "reassign therapist." The process then proceeds in the same manner as the original assignment of a physical therapist to the timer until someone in the clinic accepts responsibility for the timer. If the timer has been assigned to a physical therapy group, the alert to accept the timer will stay active until some member of the physical therapy group accepts the timer. If no person in the group accepts the timer, then another alert will be sent out at or near the expiration of the timer. Such an alert could be designed as a "high priority" alert to let the members of the physical therapy group know that someone must answer the alert immediately and accept responsibility for the timer and the patient. This approach may be advantageous in situations where the primary physical therapist of the physical therapy group, for example, is busy with a patient or some other clinic task. Another person can be quickly and virtually automatically assigned to handle the physical therapist's responsibility to check on the patient. As a result, the patient does not have to wait a prolonged time to be attended to, and the physical therapist does not have to interrupt his current task. Such an approach draws on all of the resources of the clinic, as persons who may not be very busy or are generally available can be scheduled or requested to step in to assist those with a heavier work schedule, thereby maintaining a balanced division of labor and promoting optimum use of employee time.

Even if a physical therapist or physical therapy group member has accepted a timer assignment or reassignment, he can still further reassign the timer to another person. For example, if a physical therapist in a physical therapy group member receives the notification that a timer will be expiring in two minutes, he may respond in the affirmative. However, an unexpected event may occur in those remaining two minutes that requires the attention of the physical therapist. Again, it is his responsibility at that time to reassign the timer to another physical therapy group member, even if the timer is near expiration. However, if the timer has expired and the physical therapist then concludes that he cannot attend to the patient in a reasonable amount of time due to an unexpected event, he will be unable to reassign the timer because the timer has expired, i.e., the timer effectively no longer exists. In this situation, the physical therapist must then personally message another physical therapy group member to attend to the patient, such as via the messaging portion of the app.

When the timer reaches zero or expires, an alarm or alert is sent to the assigned physical therapist or physical therapy group member, or to all physical therapy group members if no one has accepted the timer. The assigned person then visits the patient in the selected room. The assigned person can then access the room menu and select "timer answered" to indicate that he has attended to the patient. Once the "timer answered" button is pressed or after the timer expires, the server is updated to reflect that the timer has expired.

In one exemplification, a color-coding system can be used to further indicate the status of a timer, such as how much time is approximately left in the timer. For example, the timer could be listed initially in green when it first starts to let the app users know that the timer is far from expiration. Then, part way through the time, the timer could be listed in yellow or orange to indicate a substantial portion, such as half, of the time has expired. The timer could then be listed in red to indicate that the timer is near expiration, such as within the last two minutes to 30 seconds. Finally, the timer could be listed in gray to indicate that the timer has expired, and also to notify other physical therapists and physical therapy group members that the treatment was completed. In this manner, a physical therapist or physical therapy group member could quickly ascertain the general status of the timer at a glance. The preceding are possible examples, and essentially any color scheme at any desired time interval could be utilized in at least one possible exemplification.

Such an approach solves the problem of inefficient patient care by promoting timely response to the conclusion of therapy via the use of all clinic staff. For example, in one scenario, after the patient finishes his workout, he notifies the physical therapist, who then may take the patient to the assigned room and ask the patient to do a specific exercise for ten minutes. While tending to the patient, the physical therapist's mobile device starts vibrating, indicating that he has received a new alert or push notification. In this scenario, the new push notification is from the clinic staff, indicating that a new patient is in the waiting room and needs evaluation. The physical therapist accesses the app and sets a ten-minute timer for the room for the patient he is currently attending. Since the physical therapist knows that it is likely that the new patient will require more than ten minutes of his time, and since the current patient will likely not require further consultation, the physical therapist assigns the timer to a member of the clinic staff or an assistant. The assistant then receives a notification on his mobile device that the timer is now assigned to him, and he responds by accepting the timer.

After acknowledging the appropriate alerts, the assistant attends to the patient around the end of the ten-minute timer. After confirming completion of the exercises, the assistant prepares to discharge the patient. However, in talking with the patient, the assistant discovers that the patient is experiencing a new pain. Since the physical therapist is still busy with the new patient, the assistant records, via the app on his mobile device, a short message to the physical therapist detailing the patient's situation. The assistant can also record a second message to the clinic staff detailing the patient's situation, which message is then added to the patient's file for further or future evaluation. The patient is finished for the day, and the assistant discharges the patient by selecting the discharge option in the app. The server receives the discharge notice and updates the room and patient lists so that the patient's name is now cleared from the room, and the room is now listed as being available.

As can be understood from the preceding hypothetical scenario, the app system may allow a physical therapist to effectively manage multiple patients essentially without sacrificing efficiency or quality patient care. Instead of the physical therapist running from room to room and patient to patient in an inefficient and disorganized manner, the physical therapist can be aware of the status of all patients in the clinic, and can manage the time and efforts of himself and the entire clinic staff for maximum productivity.

As discussed above, the app has a main menu that permits access to various components of the app and the information therein. For example, a user, such as a physical therapist, a physical therapy group member, or a member of the clinic staff, may wish to check the waiting room list or gym list. In one exemplification, the user goes to the main page, on which is located an image of a chair, which represents the waiting room, and an image of a dumbbell, which represents the gym. Upon selecting one or the other, the server updates the chosen list to the current status for viewing by the user on his mobile device.

Also on the main page, or possibly in the main menu, can be located a "change view" button. The "change view" button is used if the user wants to change the room view options. After pressing the "change view" button, three choices are displayed: the name of the clinic, the name of the user's work group, and the user's user name. If the user chooses the clinic name, which could possibly be a single clinic or a list of clinics, the main page displays all of the rooms in the clinic. If the user chooses his work group, or possibly another work group, i.e., a physical therapy group, the main page displays all of the rooms assigned to the selected work group. Finally, if the user chooses his user name, or possibly the name of another clinic member or worker, the main page displays all of the rooms assigned to the selected person.

Another feature of the app is a messaging feature. If the user wants to send a message from his mobile device to another person in the clinic, the first question to be answered is whether the user wants to send a message regarding a specific room, or simply a general message. If a general message, the user clicks a message icon on the top corner of his mobile device. The mobile device then switches into messaging mode via the app to send a general message much like any messaging system. A pop-up dialogue box or other messaging interface lists online users who are logged into the app, and could possibly also list all users, including users who are not logged into the app but are part of the clinic staff. The user selects a person to send a message to, enters the message, and then sends same when finished. The message is stored in the server, and then, if the recipient is logged into the portal, the message is forwarded to the recipient via the recipient's mobile device or the server portal. Alternatively, messages could possibly be stored in the server until the recipient logs into the portal.

If the user wishes to send a message regarding a specific room, the user navigates to the room page if he is not already there. The user can navigate to the room page by accessing the main page, then swiping on or pressing the specific room from the list of rooms. When on the room page, the user clicks a message icon or "message" or "messaging" button on the room page, such as in the bottom right corner. A confirmation message pops up asking if the user wishes to send a message. If the user responds no, the messaging dialogue box closes. If the user responds yes, then a pop-up dialogue box appears with the list of clinic staff actively logged into the portal. Since the messaging process was initiated from a room page, when the user selects a person to send a message to, the app not only opens the messaging screen, but automatically fills in the re line with the room name/number and the patient name. The user then fills out and sends the message as described above.

One possible feature of the app is that the messages can be stored in the server as part of the overall records for future reference and accurate record keeping. Alternatively, the name of a patient can be tagged in the message, and then the message can be automatically stored in the electronic records pertaining to that patient. In this manner, information pertinent to the patient is saved in the records. As another option, the app can include a messaging alert feature for high priority messages that require immediate attention. Such messages will be received by a recipient in conjunction with an alert sound or vibration.

If a user wishes to view patient information, the user accesses the "patients" button on the menu. Again, the server first updates the patients list on the user's mobile device so all data is current. The mobile device then displays the patients page, which could be limited to a list of persons currently in the clinic. Alternatively the patients page could simply list all patients, such as alphabetically or chronologically by therapy visit dates. As another alternative, no patient names would be listed in the patient page. Regardless of the initial state of the patients page, the user can type a patient's name in a search bar, and the server starts to generate a list of patients from the database that match that search criteria. From the list of patients, the user can select a patient by clicking on his name. The mobile sends the request to the server, and the server sends the specific patient information to the mobile device. The patient page now lists the specific patient information, which can include, but is not limited to, the patient name and biographic data, total treatment time, timer information, assigned therapist or therapy group, and billing data, such as billing timers and billing units.

If an app user wants to edit patient information, it is possible to do so from his mobile device. If the user is not already on the patient information page, he can navigate to a particular patient as discussed above. On the patient information page, the user presses on the "edit" button and then is free to edit the patient details. When finished, the user presses the "back" button on his mobile device, at which time a dialogue box appears requesting to save changes or not. If the user selects "yes," the changes are saved and the mobile device sends the updated information to the server. If the user selects "no," the changes are discarded.

If an app user wants to assign a patient to a room, it is possible to do so from his mobile device. The user can assign a patient to a room from the waiting room page or the gym page in the manner discussed herein above. If the user is on the patient information page, as discussed above, the user can press the "assign to room" button. The process at that point is the same for assigning rooms, timers, etc., as discussed above.

If an app user wants to view room information, it is possible to do so from his mobile device. If the user is not on the main page, he selects the menu button and then "rooms." The mobile device then requests and receives updated information regarding rooms and/or tables from the server, as discussed above. Once the room information is updated, or if it is already updated, the user presses on the room he wishes to view. The room information page then opens up. Updated room information for that specific room is then requested and received from the server, and then displayed on the mobile device.

If an app user wants to add a task to the task list, it is possible to do so from his mobile device. There are three ways a task can be added to the task list: by notification, by manual addition, or by message. For notifications, the user receives a notification that he wishes to add to his task list. The user then presses the "add to task list" button on the notification before selecting to acknowledge the notification. The notification then appears as a task in the task list. For manual addition, the user first navigates to the task list by selecting "task list" from the menu, and then selects "add task." The user then enters the task information, and selects "save" to cause the task to appear in the task list. For messaging, the user has or receives a message he wishes to add to the task list. The user navigates to the message, and then long presses on the message. A pop-up menu appears and the user selects "add to task list" from the menu to cause the message to appear in the task list. If the user wants to delete a task from the task list, he can check a box next to the task to indicate that it is completed. A pop-up window requests confirmation that the task is completed, and, upon approval, the task is removed from the task list.

As discussed herein above, another important feature of the app is the ability to manage special patient protocols. For example, if a patient has a surgery of some kind, there may be special protocols for physical therapy related to the surgery, such as, but not limited to, restrictions on certain exercises and/or treatments, a schedule of physical therapy goals, or a specific time line for when certain therapies are to be performed. When a patient registers in the clinic for a therapy session, the patient either notifies the clinic staff of the surgery, or the information regarding the surgery is sent to the clinic from the patient's surgical physician. If the surgery does not require a protocol, then the information is noted in the records but no further action is taken. If the surgery does require a protocol that has not yet been entered into the system, the clinic staff enter the protocol into the system through the server portal.

To do so, the user navigates to the physical therapist page on the terminal or portal and selects "add protocol." A pop-up window requests the name of the protocol and waiting period for the procedure. As an alternative, a drop-down menu or similar dialogue box could possibly be used which lists many common protocols for common surgeries, such as orthopedic surgeries. After the protocol is entered, the system asks or a protocol image. If an image is available, the clinic staff scans or selects the image and uploads it into the server. The image is generally a picture or scan of the specific protocols issued by the patient's doctor, along with the waiting period for each protocol. For example, a protocol may require that the patient not lift any weights for two weeks after a shoulder surgery. There can be multiple protocols that cover different time frames, which would be and currently are rather difficult for the physical therapist and his staff to track and manage. In the system according to the present application, all of the different protocols are entered into the system and the time line for each protocol is tracked. Therefore, when a protocol's wait-time has expired, for example, the server will send a notification to the physical therapist assigned to the patient at the beginning of the patient's next visit, along with a note as a description and/or an image of the protocol itself displayed on the mobile device. The physical therapist is then easily made aware that the wait-time has expired and the patient can begin the next protocol. Once the protocol is in the system, the clinic staff select "assign protocol" from the patient page. A pop-up window requests the date of the surgery, which is entered by the clinic staff, in order to calculate the time line for the protocols. The system is then set to notify the physical therapist, such as by push notification, regarding each protocol for each patient at the appropriate time, which notification can contain the protocol notes and any images containing protocol information. The system can be set to notify the physical therapist regarding several protocols for each patient. Since these protocols could span weeks or months, it is easy for the physical therapist and/or the patient to lose track of what protocols are to be executed and at what time. By tracking all of these protocols in the system, such confusion can be avoided or minimized.

Smartwatches can also be used in specific physical therapy testing. In some therapies, it is necessary for the physical therapist to perform a range of motion test or diagnostic on a patient. A range of motion test is performed when testing how far a patient can move an extremity. For example, a patient might normally have a range of motion for his shoulder that permits him to lift his arm straight up above the level of his head. However, if a patient has a shoulder injury, he may not be able to lift his arm above the level of his shoulders or his head. In other words, his current range of motion for his shoulder is less than the original range of motion for his shoulder. However, with therapy and healing of the injury, the patient should gradually regain his original range of motion, or at least make advances toward his original range of motion, even if the original range of motion cannot be achieved. A range of motion test is therefore performed to find the current range of motion after an injury, and is performed routinely thereafter as a gauge of the efficacy of therapy and to track the healing process.

In order to measure range of motion and joint angles, a goniometer is used. This measurement instrument is a helpful, clinical tool that allows for objective measurements in order to accurately track progress in a rehabilitation program. In most instances, the goniometer comprises two plastic or metal arms that are generally about twelve inches long. The arms are attached to one another at a pivot point, much like a pair of scissors. The goniometers are marked with one degree increments and other measurements.

When using a goniometer, the physical therapist must hold the goniometer in place next to the limb or part of the body to be measured. The physical therapist must find by palpation or touch reference points or areas on the body to locate the goniometer. The physical therapist then instructs the patient to move the limb or other part of the body while the physical therapist holds the goniometer. Once the range of motion test is completed, the physical therapist must put down the goniometer and record the result. After recording the result, the physical therapist must place the goniometer in the desired location with respect to the patient's body and perform another range of motion test.

A problem with this current use of goniometers is that the range of motion measurements need to be manually entered into a computer or mobile device, or even simply written down. Such recording of data takes time and requires the physical therapist to put down the goniometer. The physical therapist then has to start the range of motion test all over again. Stopping and starting the range of motion test over and over is quite inefficient in terms of time, and can be inaccurate in terms of measurements. For example, it can be difficult to find the same reference point to obtain the most accurate measurement data. In addition to these obstacles, many times a physical therapist needs to assist a patient in stabilizing a limb in order to allow the patient to even move the limb, such as if a patient has had surgery or a substantial injury. Since the goniometer requires the use of both hands, it is virtually impossible to manually stabilize a limb of a patient and simultaneously perform the range of motion test and measurements with the goniometer. One other problem with goniometers is the correctness of the reading is not always accurate. Issues with the intra-measure (between measures) and inter-tester (between clinicians) reliability seem to increase as the experience of the examiner decreases. Some studies suggest that these errors can be anywhere between five and ten degrees when completing repeated measures.

In one possible exemplification, the goniometer is equipped with a wireless connection device that allows the goniometer to connect to a server for the transmission of measurement data. The goniometer can also be equipped with an interface for the physical therapist to allow the physical therapist to access patient and measurement information, and input measurement data. In another possible exemplification, the goniometer is additionally equipped with appropriate electronics and/or measuring devices, such as an accelerometer and/or gyroscope, to detect the range of motion automatically, rather than the physical therapist taking and inputting the measurement. Regardless of how the measurement data is obtained and entered, the information can be automatically uploaded from the goniometer to the server and stored in the EMR without the need of data entry by the physical therapist or other clinic staff.

The following scenario describes a possible exemplification of a goniometer equipped with an interface and electronic measuring devices, and its use in an overall therapy method. First, a patient arrives in the clinic for an evaluation, reevaluation or when the clinician needs to assess where a patient is in their progress. Upon checking in, the front office staff verifies if a protocol is assigned to the patient in the server. If no protocol has been assigned, the server sends the clinician a notice that no protocol is assigned. At that time, the clinician makes or selects a therapy treatment protocol through the server or his mobile device using the app. The QR code tags are scanned on the goniometer device to upload the patient testing templates. Activation is then sent to the server and the goniometer device is paired with the system wirelessly. When it is time to perform the range of motion test(s), the clinician uses the interface on the goniometer, which can be a small touchscreen, to select a template and load the preselected body parts to be measured. The clinician then confirms on the screen the body part and side to be measured. The first range of motion test is then loaded for the involved side, i.e., the side with limited range of motion. The clinician then performs a first measurement, and the results are displayed on the goniometer interface. The clinician can then choose either "accept," "test again," or "skip" on the interface. If the first measurement is accurately performed to the satisfaction of the clinician, he chooses "accept." The first measurement is then stored and the next measurement protocol is loaded. If the first measurement is not accurately performed to the satisfaction of the clinician, he chooses "test again" and then repeats the test. If the first measurement shows that the patient is within normal limits for his range of motion, i.e., his range of motion is not restricted, then the clinician chooses "skip" and proceeds on to the next measurement protocol as needed. Once the designated numbers of measurements have been tested, the clinician will move on to measure the non-involved side, i.e., non-restricted or uninjured side, for a baseline comparison. For example, if a patient's right shoulder is injured or has reduced range of motion, the right side is the involved side, and the left side is the non-involved side since the left shoulder has full range of motion. The non-involved side allows the clinician to establish a baseline for what may constitute a "normal" range of motion for the limb or body part in question, which can be used to compare with the restricted range of motion on the involved side. The same steps or options are performed for the baseline comparison. Once all measurements are completed, the data will be uploaded to the EMR and saved to the patient's file.

However, even with electronics built into the goniometer itself for the recording and transfer of data, the physical therapist still must hold the goniometer in place during the testing. In another possible exemplification, the functions of the goniometer can be performed using a smartwatch that includes accelerometers and/or gyroscopes. Instead of the measuring devices and electronics being built into the goniometer, the smartwatch contains such technology. The smartwatch is worn by the patient during a range of motion test, thereby freeing the physical therapist to do other things, such as guide the patient in the testing motion and/or manually stabilize the patient's body or body part. There is no tool to pick up or put down as the measurement device—the smartwatch—is supported on the patient.

According to one possible exemplification, to perform a range of motion test using such a smartwatch, the physical therapist first selects the patient within the mobile app. A display will appear asking if the physical therapist wishes to obtain a range of motion and/or perform a range of motion test. The physical therapist answers "yes" and then is prompted to select an active range of motion (body part moved without assistance from physical therapist) or a passive range of motion (body part moved by physical therapist). After choosing between active or passive range of motion, a body part recorded in the patient's record, such as "right shoulder," will appear on the mobile app. A menu will then pop up that gives the option to select from different options, such as "all within normal limits," "capture on watch," or "enter manually." To further explain, in most range of motion testing, the physical therapist will first perform a screening by instructing the patient to move the body part in different ways. If no restriction in movement or other difficulties are readily apparent, and the patient makes no complaint during any of the movements, the physical therapist can reasonably conclude that there is no injury. In such a scenario, the physical therapist would select "all within normal limits" to cancel any range of motion testing for that body part and move on to the next test as needed. If restrictions or difficulties are observed, then the physical therapist will proceed with the range of motion testing. At that point the physical therapist will select "capture on watch" to automatically detect and record testing data. A signal is sent to the server, and the server identifies that the watch is assigned to a specific patient for the day. The server will then send back to the watch information for displaying the selected range of motion test, such as, for example, passive range of motion flexion. The therapist can then choose either "skip" or "start." "Skip" is chosen if the particular range of motion test is unnecessary due to the patient performing full, unrestricted motion for that particular test. However, if the test is needed, the physical therapist selects "start." The physical therapist then taps anywhere on the display to set the initial measurement value to zero. The clinician will then execute the range of motion test by moving the body part of the patient in the desired manner as far as possible. When the movement or motion has reached its limit, the physical therapist presses anywhere on the screen to capture the range of motion measurement. At this point a message is displayed with the captured data and/or a message requesting confirmation of the test. If the physical therapist is satisfied with the test, he will press yes to approve the test, and the system will then queue the next measurement. Alternatively, the system could be designed such that whenever data is captured, the system will confirm the capture and then automatically queue the next measurement. The process will continue until all schedule range of motion tests are completed. All measurements will be uploaded to the system and stored in the EMR for the patient.

Manual muscle testing is a procedure for the evaluation of the function and strength of individual muscles and muscle groups based on the effective performance of a movement in relation to the forces of gravity and manual resistance. Dynamometry is a method of strength testing using sophisticated strength measuring devices, e.g., hand-grip, handheld, fixed, and isokinetic dynamometry.

When performing strength testing, a particular muscle or muscle group is first isolated, then an external force is applied. Resistance applied at the end of the tested range is termed a "break test." The handheld devices used in dynamometry can help quantify the "breaking force" necessary to depress a limb held in a specific position by the patient. Resistance should be applied and released gradually to give the patient sufficient time to offer resistance. Following the manual muscle test, the muscle tested is said to be "weak" or "strong" based upon the muscle's ability to resist the externally applied force over time. Currently a grading system is used for manual muscle testing. There are three notable manual muscle testing scales: the Medical Research Council (MRC); Daniels and Worthingham (DW); and Kendall and McCreary (KM). MRC uses a numeric scale of 0-5, DW uses words like poor and normal, and KM uses a percentage scale. The highest scores indicate that the patient holds the test position against moderate to maximum resistance, whereas the lowest scores indicate very little to no muscle contraction or movement.

While these scales all measure muscle strength and functionality, they are all different to some degree. In the MRC scale, the grades of 0, 1, and 2 are tested in the gravity-minimized position (contraction is perpendicular to the gravitational force). All other grades are tested in the anti-gravity position. The DW grading system is considered the more functional of the three grading systems because it tests a motion that utilizes all of the agonists and synergists involved in the motion. The KM approach is designed to test a specific muscle rather than the motion, and requires both selective recruitment of a muscle by the patient and a sound knowledge of anatomy and kinesiology on the part of the clinician to determine the correct alignment of the muscle fibers. Choosing a particular grading system is based on skill level of the clinician while ensuring consistency for each patient, so that coworkers who may be re-examining the patient are using the same testing methods. However, it must be remembered that the grades obtained with manual muscle testing are largely subjective and depend on a number of factors including the effect of gravity, the manual force used by the clinician, the patient's age, the extent of the injury, and cognitive and emotional factors of both patient and clinician.

The test should be completed on the uninvolved side first to ascertain normal strength before being repeated on the involved side. The patient is instructed to complete the test movement again and then hold the body part in the desired position. The clinician alerts the patient that resistance will be applied and then applies resistance in the appropriate direction and in a smooth and gradual fashion.

There are a number of issues within the current treatment procedure. One problem is that manual muscle testing is a measurement assigned by the clinician and is not objective data so it can differ from clinician to clinician. According to one exemplification, a standardized device (dynamometry) can be used that can eliminate the discrepancy from clinician to clinician. Clinicians would no longer need to use an arbitrary scale, but rather could use an accurate gauge based on a template in the system. Another problem is that data needs to be manually entered into a computer or mobile device, which takes time. According to one exemplification, once a patient completes their assigned protocol and baseline comparison, all data is uploaded to the server and stored in the EMR.

The following scenario describes a possible exemplification of a manual muscle testing method. First, a patient arrives in the clinic for an evaluation, reevaluation or when the clinician needs to assess where a patient is in their progress. Upon checking in, the front office staff verifies if a protocol is assigned to the patient in the server. If no protocol has been assigned, the server sends the clinician a notice that no protocol is assigned. At that time, the clinician makes or selects a therapy treatment protocol through the server or his mobile device using the app. Once a protocol is assigned in the server, the QR code tags are scanned on the watch and on the manual muscle testing device to upload patient templates. Activation is then sent to the server and the manual muscle testing device is paired with the system via Bluetooth or Wi-Fi. The clinician will select a template on the involved side and load the preselected body part(s) to be tested. The clinician then confirms on the screen the body part and side. Test muscle/muscle group #1 is loaded on the involved side. The clinician tests the peak muscle strength which is displayed on the watch device. Options will be given to "accept," "test again," or "skip." If "accept" is chosen, the test for the muscle/muscle group #2 is loaded and then the clinician proceeds. If "test again" is chosen, the clinician repeats the process again. Choosing "skip" indicates that the patient is within normal limits. Once the designated number of muscles/muscle groups have been tested, the clinician will move on to test the non-involved side for a baseline comparison. The same steps/options are preformed for the baseline comparison. Once all testing is complete, the data will be uploaded to the EMR (Electric Medical Record) and saved to the patient's file.

According to one exemplification, a manual muscle testing device that can be used by itself or in conjunction with an EMR system, such as is described herein, is a glove device that can be worn by either the patient or the physical therapist, depending on the therapeutic procedure. The glove device has a body portion that fits around the hand of a user. The body portion is a partial glove that covers only the palm area of the user's hand with the fingers exposed, or is a complete glove that covers the entire hand of the users including fingers. The body portion can be made of cloth, fibrous material, plastic, mesh, nylon, polyester, or elastic material, with or without one or more securing straps. The securing straps could include a securing structure comprising hook and loop material or other temporary securing or holding or locking structures.

Attached to the body portion is a sensor portion that includes one or more pressure sensors located in the palm of a user's hand when the glove is worn. The pressure sensors could be flexible force sensors or other types of malleable sensors. The sensor portion is connected by wiring to a control device, such as a microcomputer, which is connected wirelessly to the EMR server. The information received from the sensor portion is then transmitted to the clinic server. As an alternative, the glove could be located at a particular treatment station and wired into a source of power and a data communication platform to transmit testing data to the clinic server. The sensor portion could also be divided into two portions, each wired to the control device.

In most manual muscle testing procedures, the physical therapist grips or presses against the body part of the patient to be tested. The physical therapist often estimates by feel the relative strength or weakness of the body part. Not only can this be inaccurate, but the data can be very subjective depending on the physical therapist conducting the test. In other cases, the physical therapist uses a handheld pressure sensor device, which is pressed against the body part being tested. The pressure measurement is more consistent and accurate than measuring by feel, but often the devices can be cumbersome and awkward to use. They can also be painful for the patient when they are pressed against the body part of the patient as the structure of the devices is often firm, rigid, or hard. The glove device, according to one exemplification, addresses these deficiencies. Since the glove device includes one or more pressure sensors, consistent, accurate, and objective data can be obtained that does not vary from physical therapist to physical therapist. The pressure sensors themselves can be made of soft and/or flexible material, and can be housed in soft and/or flexible material. Thus, when the pressure sensors are pressed against the patient's body part, pain and/or discomfort is minimized or eliminated. By placing the pressure sensors in a glove worn by the physical therapist, the pressure sensors take advantage of the natural gripping position or action of the human hand. Instead of possibly awkwardly holding a pressure device and trying to maneuver the device into the desired testing position to obtain the desired data, the pressure sensors can be easily positioned and manipulated as essentially an extension of the hand of the physical therapist. For example, should a physical therapist wish to test arm strength of a patient, the physical therapist can simply grasp the patient's arm and have the patient resist the pushing or pulling force of the physical therapist, or vice versa. Such a method would not only be comfortable for the patient, but also comfortable for the physical therapist, thereby promoting fast and accurate manual muscle testing. In addition, if the physical therapist wishes to test two or more motions, such as pushing and pulling by the arm of a patient, the physical therapist either judges by feel or uses a handheld device. The handheld device must be re-positioned for each different motion and direction of movement, which can be awkward and inefficient. In contrast, the glove can be designed so that the physical therapist just needs to grasp, in this scenario, the arm of the patient one time, and then push or pull the patient's arm in different motions, or have the patient execute different motions against the resistance of the physical therapist. To achieve this versatility, the glove can include multiple pressure sensors in the sensor portion to pick up pressure data from different motions. The sensor portion can even be divided into two separate sections with separate pressure sensors. This design can possibly increase comfort for the patient and control for the physical therapist as thicker cushioning material could be used, and the patient's body part can better settle into the groove or gap between the two sections for improved gripping. Different sensors in the separate sections could also be designated as measuring different motions or movements.

The manual muscle testing procedures are guided by a patient template that is uploaded to either the mobile device of the physical therapist, or possibly to the manual muscle testing device, such as the glove device. For that purpose, the glove device could include a display built into the control device, or possibly located elsewhere on the glove, such as on the back of the glove. Regardless of where the patient template is displayed, the display will show the first manual muscle test to be performed. If the patient initially demonstrates full strength and freedom of movement for that particular test, the physical therapist can choose to skip the test and move on to the next one. If the patient does not, then physical therapist conducts the test as instructed on the display. When the test is completed, the test results or data are shown on the display. In the case of the display being on the mobile device of the physical therapist, the test results are first sent from the control device on the glove to the server, and then relayed from the server to the mobile device. In the case of the display being on the glove itself, the test results are immediately shown on the display on the glove. At that point the physical therapist can either accept the test results if he believes the test was done properly or accurately, or reject the test results if he believes the test was not done properly or accurately. If he accepts the test results, the data is uploaded to the server and matched to the patient's record, and the display then shows the next test to be performed, if any. If he rejects the test, results, the display shows the test again and the physical therapist performs the test again, as many times as necessary until the test results are accepted. This process is repeated until all tests are performed and the results accepted and stored.

Figure 39:
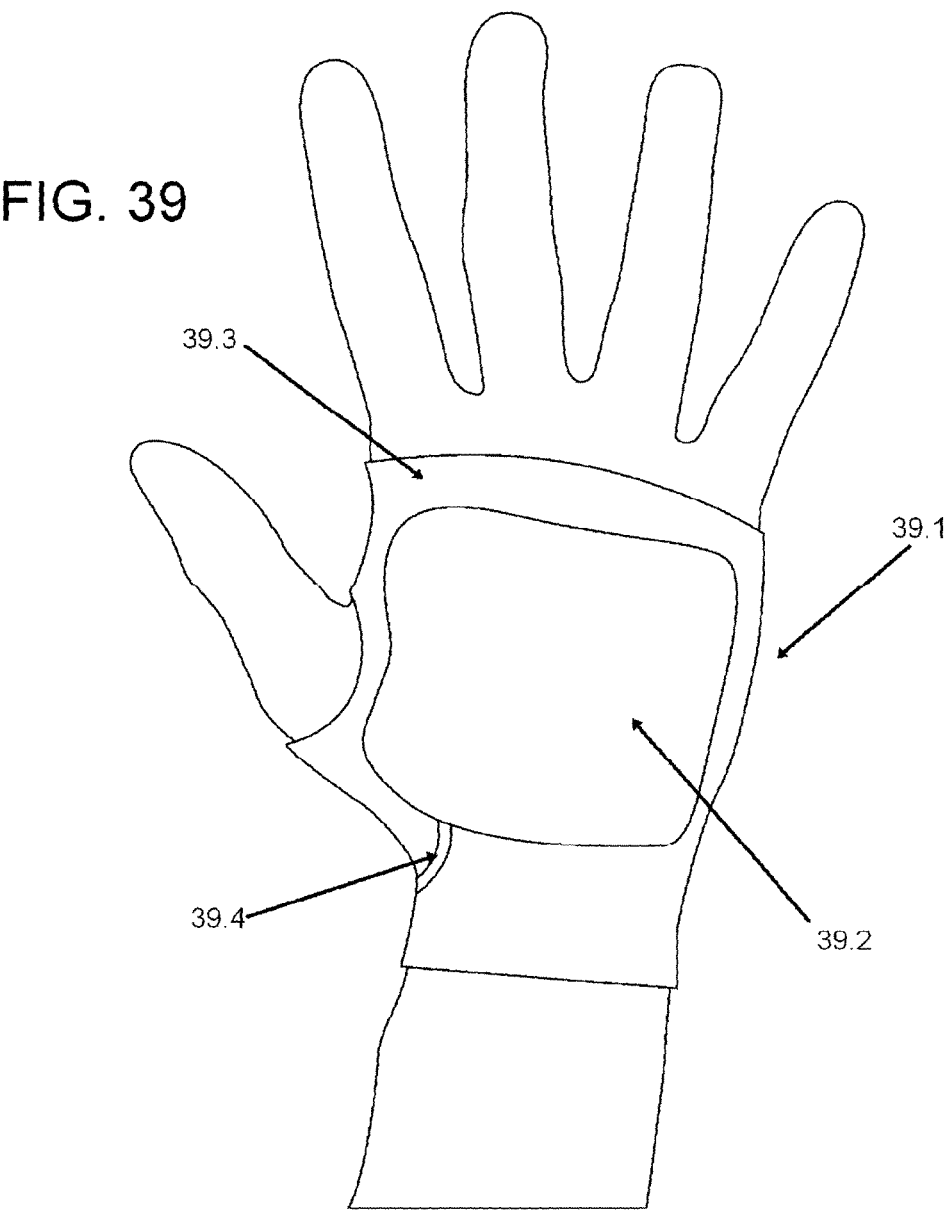
FIGS. 39, 40, and 41 show an exemplification of a glove device.
Figure 40:
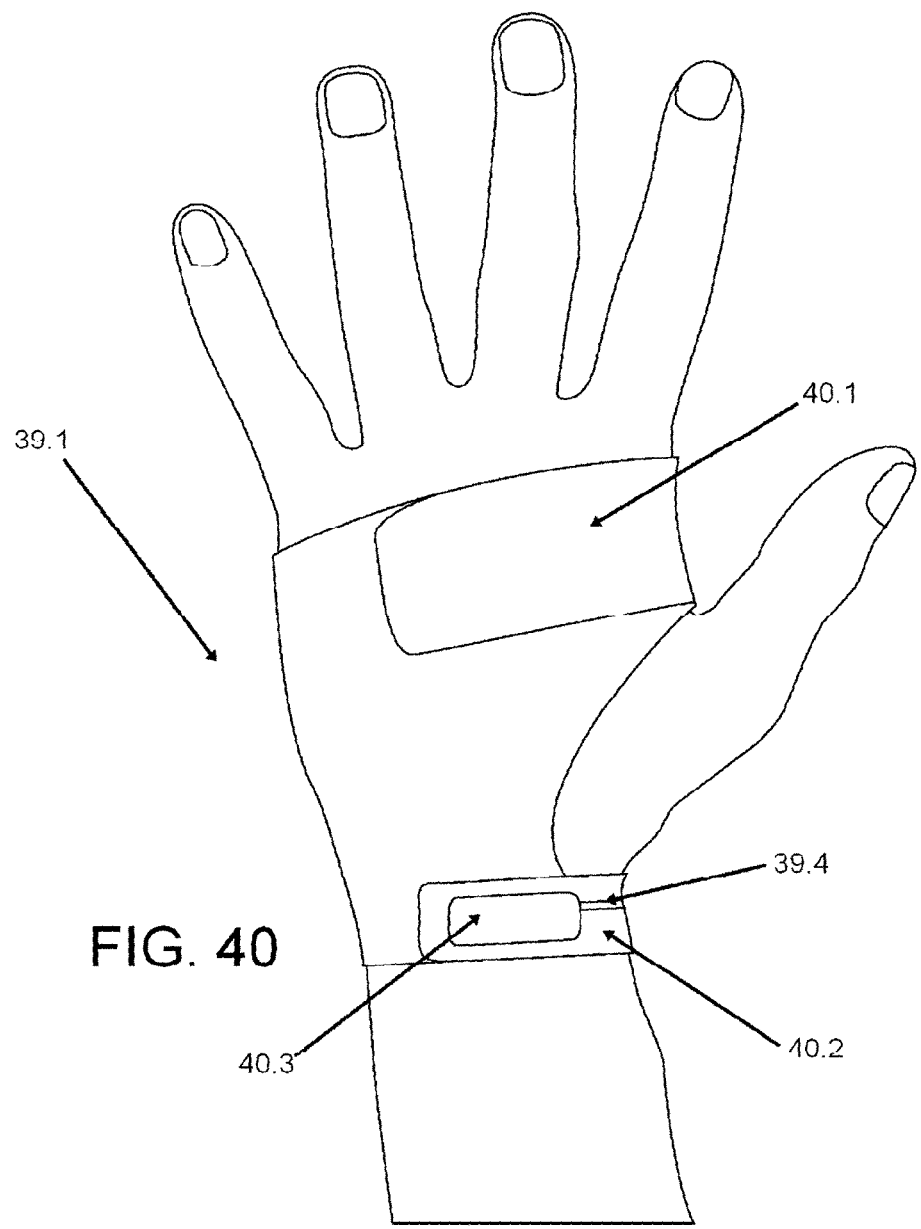
Figure 41:
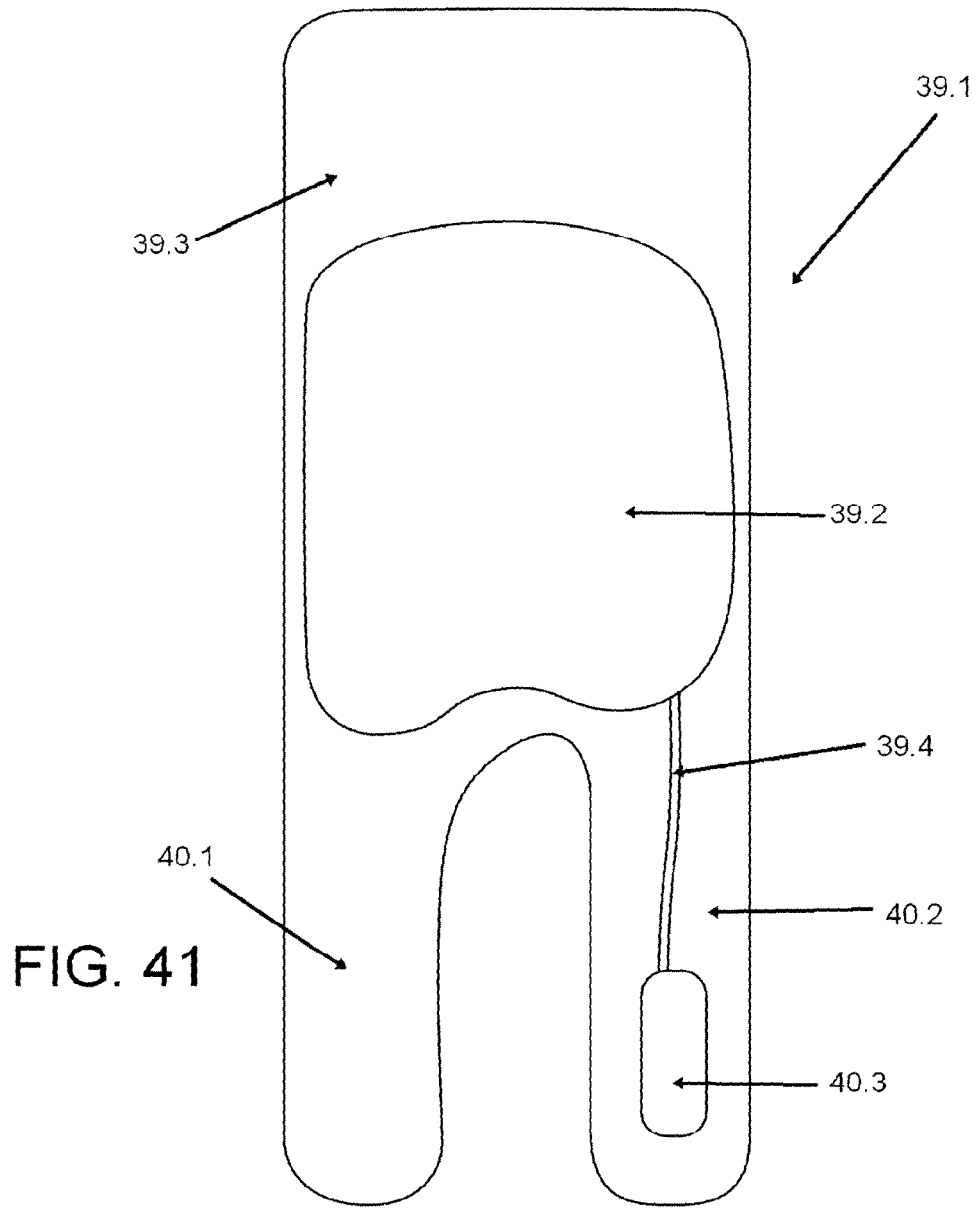

FIG. 39 shows an exemplification of a glove 39.1 for manual muscle testing on a hand of a user. The sensor portion 39.2 is attached to the body portion 39.3 of the glove 39.1. Wiring 39.4 is connected to the sensor portion 39.2 and attached to the body portion 39.3. FIG. 40 shows the back of the glove 39.1. A palm strap 40.1 and a wrist strap 40.2 are visible. The straps 40.1, 40.2 can be hook and loop straps or the like. The control device 40.3 is connected to the wrist strap 40.2. FIG. 41 shows the palm or sensor side of the glove 39.1, but flattened out as it would appear when not wrapped around the hand of a user.

Figure 42:
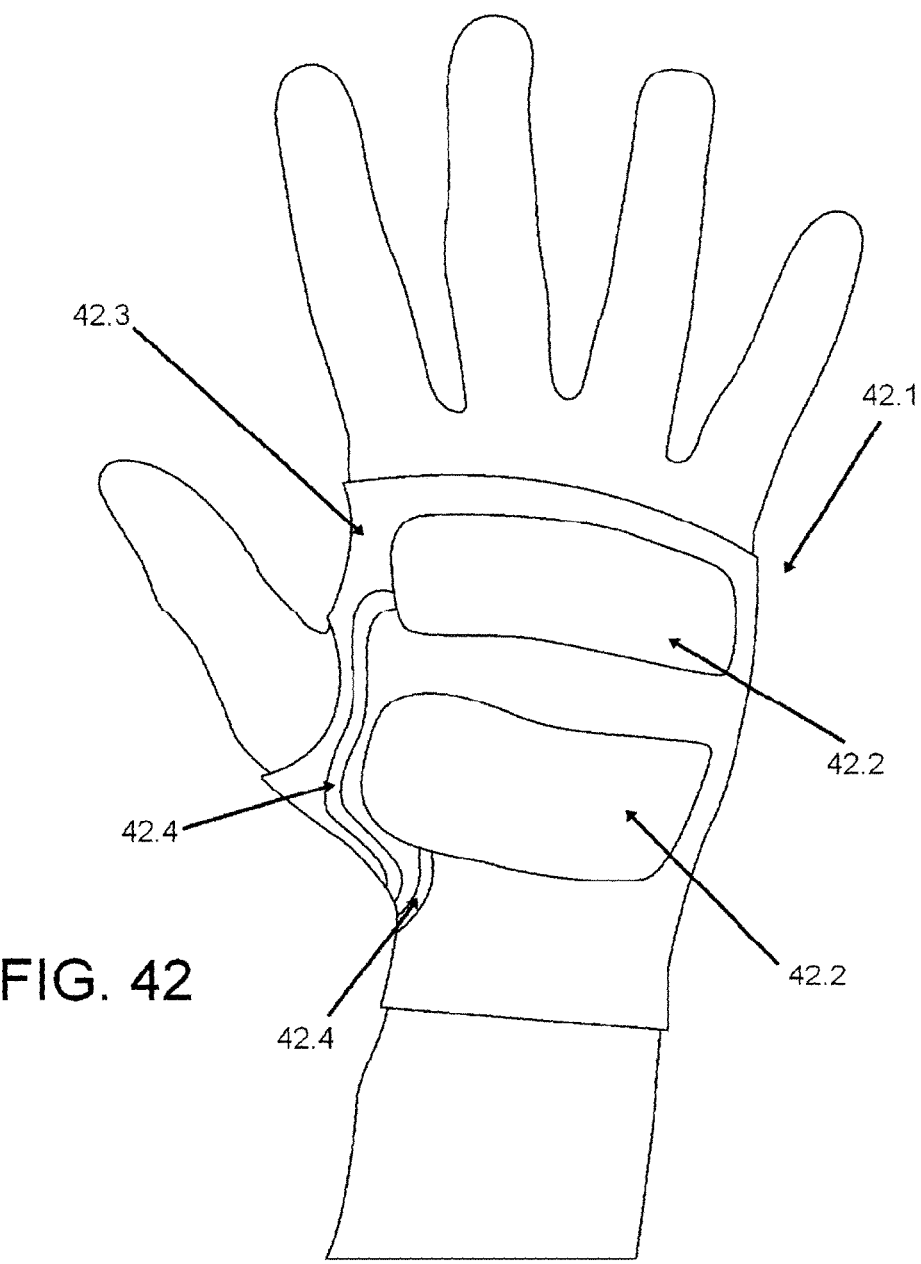
Figure 43:
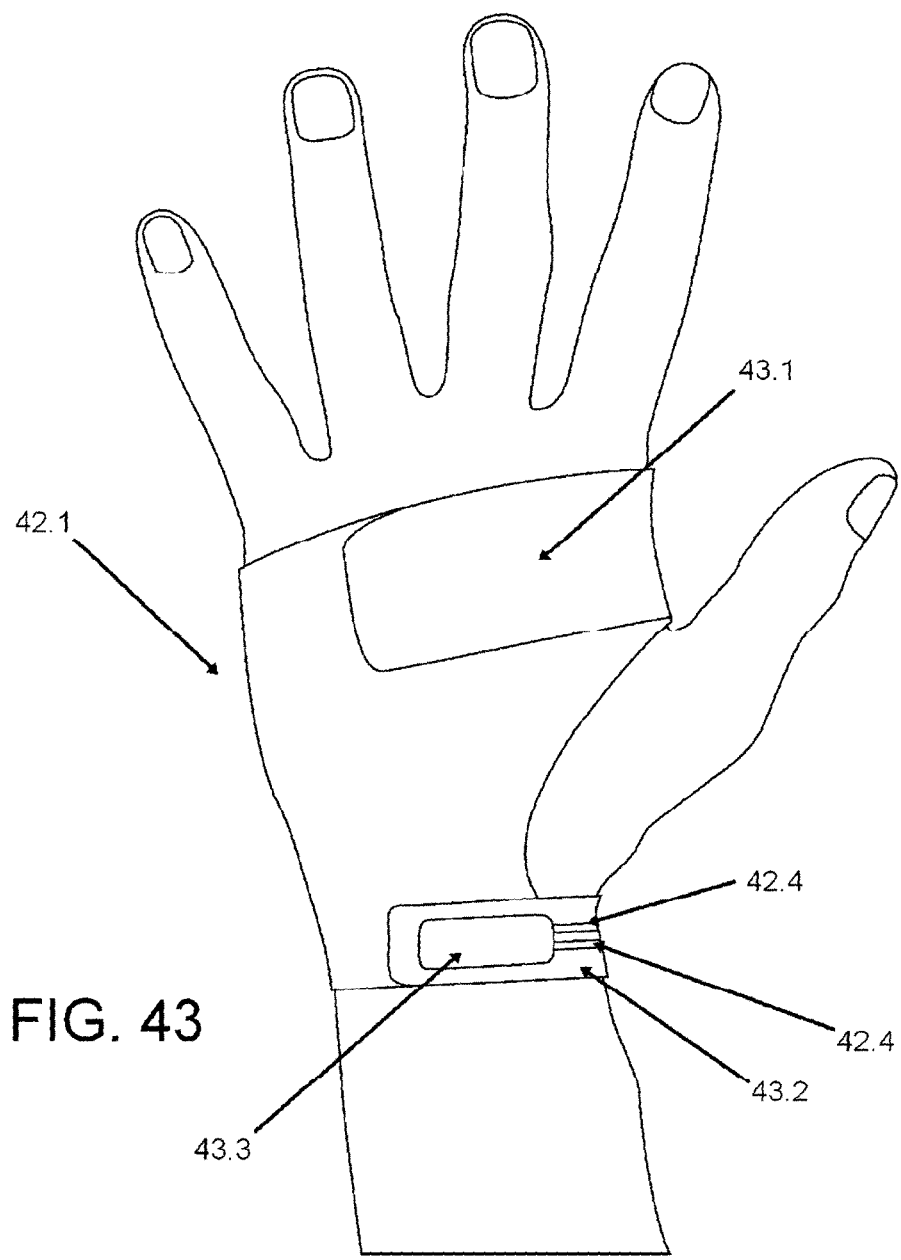

FIG. 42 shows a different exemplification of a glove 42.1 for manual muscle testing on a hand of a user. Instead of a single sensor portion, there are two sensor portions 42.2 attached to the body portion 42.3 of the glove 42.1. Two sections of wiring 42.4 are connected to the sensor portions 42.2 and are attached to the body portion 42.3. FIG. 43 shows the back of the glove 42.1. A palm strap 43.1 and a wrist strap 43.2 are visible. The straps 43.1, 43.2 can be hook and loop straps or the like. The control device 43.3 is connected to the wrist strap 43.2. FIG. 44 shows the palm or sensor side of the glove 42.1, but flattened out as it would appear when not wrapped around the hand of a user.

Figure 38:
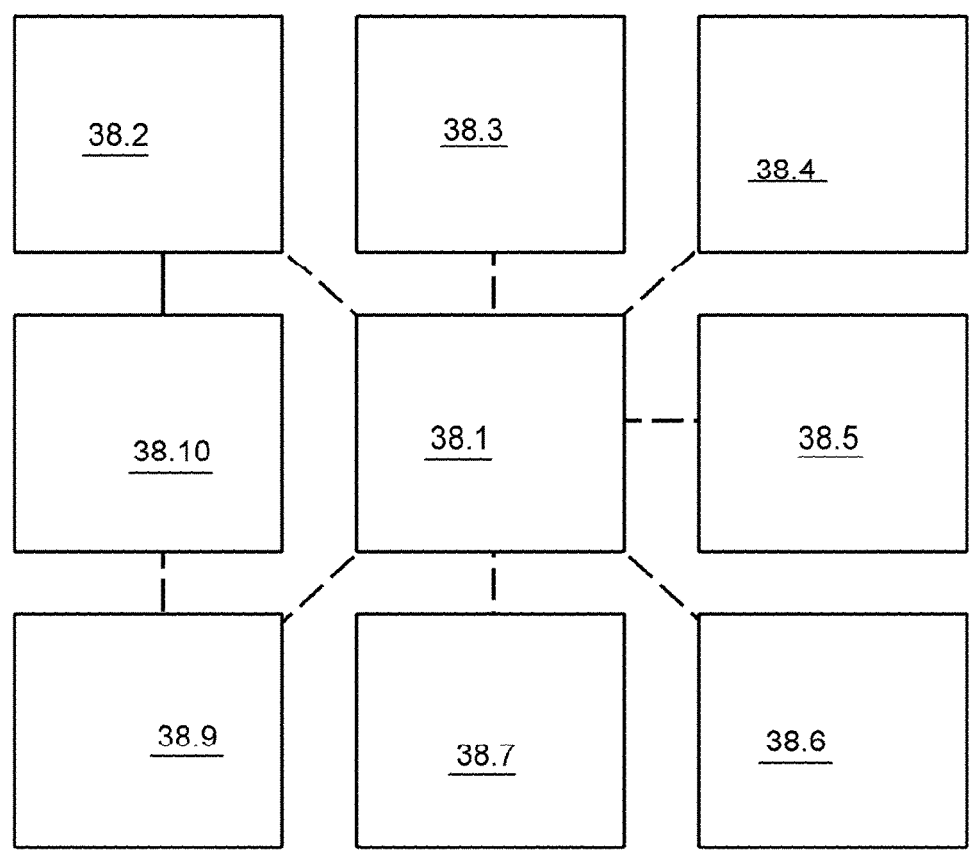
FIG. 38 shows a block diagram of an exemplification of a smartwatch system and related components.

According to one exemplification, the overall systems and devices are all connected together into a single system, as shown in FIG. 38. At the center is a server or computer server 38.1, which controls and joins all of the other systems and devices. The smartwatches 38.2 are wirelessly connected or paired to the server 38.1. Mobile devices 38.3, such as smartphones and tablets, are also wirelessly connected to the server 38.1 via the app interface. A device such as a goniometer or a smartwatch functioning as a goniometer is wirelessly connected or paired to the server. One or more server portals, such as work stations or desktop computers or displays, are connected to the server either wirelessly or by a wired connection. The EMR may be stored locally on the server itself, or it may be stored elsewhere on another device, such as a computer or server, that the server can access. Any facial recognition components are connected to the server for the transmission of facial recognition information. A tracking system, such as a triangulation or RFID system, may be connected to the server either wirelessly or by a wired connection. Tracking devices are not directly connected to the server if they are in the form of wearable tags or beacons that only are detected by the tracking system. However, if the tracking device is part of a smartwatch, then the tracking device is connected via the smartwatch to the server for the transmission of tracking data, such as movement and positional data. Essentially all of the systems and devices are in some type of communication with one another via the server for the sharing and exchanging of information and data.

According to one exemplification, a tracking device, such as a beacon or RFID or triangulation device, can be used in conjunction with the app and smartwatch in a physical therapy clinic. The tracking device can provide accurate location indoors, to thereby provide the app with physical location information inside of a clinical setting. The tracking device will be secured to the watch device that the patient will be wearing. Data will be collected and utilized in various ways regarding the movement of patients and clinical staff. The tracking device will allow turn-by-turn guidance of the floor plan set. When a device is near or leaves a point of interest, it triggers a given action. This occurs to follow the real-time movement of people and their activities inside a specific building by setting up a wireless triangulation system or RFID grid. By capturing traffic throughout a site to analyze visitor movement and flow, including queue times, dwell times, wait times and first time/repeat visitors, it allows more accurate records for the patient/clinician. This device will allow tracking from wearable devices and smart watches, smart phones, and tablets.

Smart watches, fitness trackers, and beacons allow users to track complex motions requiring the use of motion sensors such as gyroscopes, accelerometers, compasses, and pressure sensors, fusing the sensor outputs into a single and accurate data stream for use as input commands in consumer electronics devices, and ongoing run-time calibration to ensure an optimal user experience.

In therapeutic rehabilitation, clinicians instruct patients through a therapeutic exercise routine. This is set up by a licensed clinician to treat a patient's condition. The clinician creates a treatment plan/protocol. The clinician instructs the patient through the exercises, demonstrates or displays the exercise techniques, and follows the patients through their therapeutic exercise routine. Commonly a flow sheet is used, which is a list of the treatment procedures and the order in which the patient is to receive them.

When a patient comes to the clinic, he is registered and assigned to clinician or workgroup if not already. A protocol/flow sheet for the prescribed therapy is assigned to the patient. The patient is then given a device, such as a smartwatch, with tracking capability. A member of the clinic staff will scan the QR code of the watch or other device to upload the patient's template on the device and assign the patient to the given clinical workgroup. The smartwatch could also be paired to the patient's account electronically via a wireless connection. Activation is sent to the server and the watch is paired with the computer system/mobile device. The server then sends an alert to the clinical workgroup that the patient is in the waiting room. The patient is then traceable through the tracking device. Once the patient reaches ambulation or gait activities, i.e. walking, jogging, running, from their flow sheets, the system pings to triangulate their location. The system pings all clinicians watches to see if any are with patients. When ready, the clinician or patient chooses "start" on the watch/mobile device. When choosing "start," the device displays the treatment procedure and exercise to begin. The preloaded exercise protocol is displayed. A wireless system (Wi-Fi®, Bluetooth®) pings the patient and any clinician in proximity in time intervals, such as every second, to determine location/triangulation until an exercise complete button, such as "walk completed," is pressed on the watch/mobile device. The watch will then display a message asking if another ambulation/walk is listed on the flow chart. If yes, the next task is performed. If no, the speed, distance, and time is saved to the patient's chart.

The system, computer or mobile device, sends an alert to the clinician's mobile device and confirms whether or not the clinician performed the exercise with the patient and the level of assistance. The next item from the flow chart is listed on the patient's smart watch/mobile device.

The system sends a push notification to the clinician's mobile deice that was present though the patient's entire walk. The screen displays a data message, such as "Did you assist <<patient's name>> with ambulation?" The clinician can select yes or no. If yes, the screen will show different levels of assistance, such as contact guard assistance, minimum assistance, moderate assistance, and maximum assistance. Once selected, this information will be saved to the patient's chart in the notes section with the clinician's name and assistance level.

According to one possible exemplification, the app can be used in conjunction with facial recognition technology. The purpose of facial recognition is to further expedite the paperwork process of the EMR. The facial recognition system allows a patient to be automatically logged into the system as he arrives for a scheduled appointment, without the need of the therapist to enter the patient or notify the therapist. Within the clinic, this system utilizes two cameras near the entrance/exit of the clinic: one at the entrance (within the clinic) pointed at the entrance, and one at the exit, facing from the door towards the inside of the clinic. While each clinic can have unique camera placements, the placements are such that the entrance camera captures the picture of patients entering the clinic, and the exit camera captures patients as they leave the clinic.

The facial recognition system can help address some deficiencies in current clinic operations. One problem is that when a patient enters a clinic, it can often take between five and twenty minutes before the clinician is notified of the patient's presence in the wait room. In current clinics, the patient's presence is denoted by the patient's chart being placed in a holder in view of most of the clinic. However, with the busyness of a clinic, the clinician may not immediately notice. In the past twenty years of technological advances, no practical method has been devised to quickly and efficiently notify clinicians of patient arrival in physical therapy clinics, chiropractic practices, and related healthcare practices.

The facial recognition system can interact with the app to identify patients as they enter the clinic and notify the clinician within moments of the patient entering the clinic. This is achieved using a camera and facial recognition software. When a patient approaches the door, the camera takes a snapshot of the patient and sends it to the server. The server runs facial recognition on the picture, and compares the photo to the patient profiles stored in the system. If there is a match, the system sends a message to the server to send a push notification to the clinician with whom the patient has an appointment. This works in conjunction with the ability of the clinic staff to notify the clinician through the app to promote shorter wait times for the patient of only a few minutes or less, and minimize the chances of the patient being subjected to substantial wait times of more than a few minutes.

In addition, to reducing wait times for patients, the facial recognition system can also be used to help reduce, minimize, or eliminate fraud. In that regard, insurance companies are always looking for ways to eliminate fraud from the medical system. Unfortunately, auditing can only give the insurance companies so much information, and the insurance companies must rely on the word of medical professionals as to the accuracy of the statements. One source of fraud includes fake claims for nonexistent patients being billed to insurance companies, especially Medicare and Medicaid.

When the facial recognition system uses a photo to recognize an incoming patient and notify the clinician, the system will also attach that photo to the electronic chart containing the notes from that visit. The clinic will also have a camera inside the front door that catches the faces of patients as they exit the clinic. This photo is added to the chart, along with time stamps to indicate patient entrance and exit. This documented information gives certifiable or verifiable proof that a patient in question has in fact been at the clinic and received treatment. Such information will also make fraudulent cases stand out. Patients with multiple visits and no picture whatsoever will be highlighted by insurance companies for investigation. This allows insurance companies to focus their efforts to eliminate fraud, and allows clinics to ensure that their clinics are above reproach.

The following patent publications are incorporated by reference as if set forth in their entirety herein: U.S. Patent Application Publication No. 2015/0172893; U.S. Pat. No. 9,274,507; U.S. Pat. No. 9,454,898; U.S. Pat. No. 8,854,925; U.S. Pat. No. 9,282,284; U.S. Pat. No. 9,405,967; U.S. Pat. No. 9,230,158; U.S. Pat. No. 9,389,300; U.S. Pat. No. 9,204,251; U.S. Pat. No. 7,119,687; U.S. Design Pat. No. D750,621; U.S. Design Pat. No. D678,873; U.S. Pat. No. 9,274,507; U.S. Design Pat. No. D766,114; U.S. Pat. No. 9,086,687; U.S. Design Pat. No. D765,655; U.S. Pat. No. 9,459,698; and U.S. Pat. No. 9,282,127.

One feature or aspect of an exemplification is believed at the time of the filing of this patent application to possibly reside broadly in a smartwatch system comprising: a first smartwatch, said first smartwatch comprising: a watch housing; a watch band configured to be wrapped around a portion of a limb of a user to secure said watch housing to the limb of the user; said watch band comprising a first band portion and a second band portion, each being attached to said watch housing; a buckle or similar connecting structure to detachably connect said first band portion and said second band portion; a battery disposed in said watch housing to supply power to said first smartwatch; an audio device disposed in said watch housing and configured to emit sound and/or receive sound; a tracking arrangement disposed in said watch housing and configured to permit detection of the location of said first smartwatch in an area; said tracking arrangement comprising a global positioning device and/or a triangulation device disposed in said watch housing; a motion detection arrangement disposed in said watch housing and configured to permit detection of the movement of said first smartwatch in at least one plane of movement; said motion detection arrangement comprising at least one of: motion sensors, gyroscopes, and accelerometers disposed in said watch housing; a processor disposed in said watch housing and configured to control operation of said first smartwatch; a memory disposed in said watch housing and configured to store data, including information data specific to the physiological status and activity of a user; a wireless communication device disposed in said watch housing and configured to wirelessly connect said first smartwatch to an external communication device; a display disposed on the front of said watch housing and configured to display digital information and/or visual information comprising data and/ or messages and/or images to the user; and said display comprising a touch screen interface to permit tactile input of commands and/or data by the user to execute different functions of said first smartwatch; a second smartwatch, said second smartwatch comprising: a watch housing; a watch band configured to be wrapped around a portion of a limb of a user to secure said watch housing to the limb of the user; said watch band comprising a first band portion and a second band portion, each being attached to said watch housing; a buckle or similar connecting structure to detachably connect said first band portion and said second band portion; a battery disposed in said watch housing to supply power to said second smartwatch; an audio device disposed in said watch housing and configured to emit sound and/or receive sound; a tracking arrangement disposed in said watch housing and configured to permit detection of the location of said second smartwatch in an area; said tracking arrangement comprising a global positioning device and/or a triangulation device disposed in said watch housing; a motion detection arrangement disposed in said watch housing and configured to permit detection of the movement of said second smartwatch in at least one plane of movement; said motion detection arrangement comprising at least one of: motion sensors, gyroscopes, and accelerometers disposed in said watch housing; a processor disposed in said watch housing and configured to control operation of said second smartwatch; a memory disposed in said watch housing and configured to store data, including information data specific to the physiological status and activity of a user; a wireless communication device disposed in said watch housing and configured to wirelessly connect said second smartwatch to an external communication device; a display disposed on the front of said watch housing and configured to display digital information and/or visual information comprising data and/or messages and/or images to the user; and said display comprising a touch screen interface to permit tactile input of commands and/or data by the user to execute different functions of said second smartwatch; and said first smartwatch being configured to display images and/or information relating to a first physiological activity specific to a first user of said first smartwatch, and said second smartwatch being configured to display images and/or information relating to a second physiological activity specific to a second user of said second smartwatch; and said touch screen interfaces of each of said first and second smartwatches being configured to permit tactile input of commands and/or data by a user relating to a physiological activity.

Another feature or aspect of an exemplification is believed at the time of the filing of this patent application to possibly reside broadly in the smartwatch system, wherein: said first smartwatch is configured to display a description of a first physiological activity, specific to a first user of said first smartwatch, to be performed by a first user of said first smartwatch; and said second smartwatch is configured to display a description of a second physiological activity, specific to a second user of said second smartwatch, to be performed by a second user of said second smartwatch.

Yet another feature or aspect of an exemplification is believed at the time of the filing of this patent application to possibly reside broadly in the smartwatch system, wherein: said first smartwatch is configured to display a duration of a first physiological activity, specific to a first user of said first smartwatch, to be performed by a first user of said first smartwatch; and said second smartwatch is configured to display a duration of a second physiological activity, specific to a second user of said second smartwatch, to be performed by a second user of said second smartwatch.

Still another feature or aspect of an exemplification is believed at the time of the filing of this patent application to possibly reside broadly in the smartwatch system, wherein: said first smartwatch is configured to permit tactile input to alter at least one parameter of how a first physiological activity, specific to a first user of said first smartwatch, is to be performed by a first user of said first smartwatch; and said second smartwatch is configured to permit tactile input to alter at least one parameter of how a second physiological activity, specific to a second user of said second smartwatch, is to be performed by a second user of said second smartwatch.

A further feature or aspect of an exemplification is believed at the time of the filing of this patent application to possibly reside broadly in the smartwatch system, wherein: said first smartwatch is configured to permit tactile input to alter duration of how long a first physiological activity, specific to a first user of said first smartwatch, is to be performed by a first user of said first smartwatch; and said second smartwatch is configured to permit tactile input to alter duration of how long a second physiological activity, specific to a second user of said second smartwatch, is to be performed by a second user of said second smartwatch.

Another feature or aspect of an exemplification is believed at the time of the filing of this patent application to possibly reside broadly in the smartwatch system, wherein: said first smartwatch is configured to display a first location where a first physiological activity, specific to a first user of said first smartwatch, is to be performed by a first user of said first smartwatch; and said second smartwatch is configured to display a second location where a second physiological activity, specific to a second user of said second smartwatch, is to be performed by a second user of said second smartwatch.

Yet another feature or aspect of an exemplification is believed at the time of the filing of this patent application to possibly reside broadly in the smartwatch system, wherein: said first smartwatch is configured to wirelessly transmit to an external communication device a location of where a first physiological activity, specific to a first user of said first smartwatch, is being performed by a first user of said first smartwatch; and said second smartwatch is configured to wirelessly transmit to an external communication device a location of where a second physiological activity, specific to a second user of said second smartwatch, is being performed by a second user of said second smartwatch.

Still another feature or aspect of an exemplification is believed at the time of the filing of this patent application to possibly reside broadly in the smartwatch system, wherein: said first smartwatch is configured to permit tactile input to permit a first user of said first smartwatch to record commencement of a first physiological activity, specific to a first user of said first smartwatch; said second smartwatch is configured to permit tactile input to permit a second user of said second smartwatch to record commencement of a second physiological activity, specific to a second user of said second smartwatch; and said wireless communication devices of said first and second smartwatches are configured to wirelessly transmit the time of the commencement of a physiological activity to an external communication device.

A further feature or aspect of an exemplification is believed at the time of the filing of this patent application to possibly reside broadly in the smartwatch system, wherein: said first smartwatch is configured to permit tactile input to permit a first user of said first smartwatch to record completion of a first physiological activity, specific to a first user of said first smartwatch, or is configured to automatically record completion of the first physiological activity after a predetermined period of time; said second smartwatch is configured to permit tactile input to permit a second user of said second smartwatch to record completion of a second physiological activity, specific to a second user of said second smartwatch, or is configured to automatically record completion of the first physiological activity after a predetermined period of time; and said wireless communication devices of said first and second smartwatches are configured to wirelessly transmit the time of completion of a physiological activity to an external communication device.

Another feature or aspect of an exemplification is believed at the time of the filing of this patent application to possibly reside broadly in the smartwatch system, wherein: said first smartwatch is configured to display a description of a third physiological activity, different from the first physiological activity, to be performed by a first user of said first smartwatch upon completion of the first physiological activity; and said second smartwatch is configured to display a description of a fourth physiological activity, different from the second physiological activity, to be performed by a second user of said second smartwatch upon completion of the second physiological activity.

Yet another feature or aspect of an exemplification is believed at the time of the filing of this patent application to possibly reside broadly in the smartwatch system, wherein: said first smartwatch is configured to display a third location where the third physiological activity is to be performed by a first user of said first smartwatch, which third location may be the same as or different from the first location; and said second smartwatch is configured to display a fourth location where the fourth physiological activity is to be performed by a second user of said second smartwatch, which fourth location may be the same as or different from the second location.

Still another feature or aspect of an exemplification is believed at the time of the filing of this patent application to possibly reside broadly in the smartwatch system, wherein: said first smartwatch is configured to permit tactile input to alter at least one parameter of how a first physiological activity, specific to a first user of said first smartwatch, during performance of the first physiological activity by a first user of said first smartwatch; and said second smartwatch is configured to permit tactile input to alter at least one parameter of how a second physiological activity, specific to a second user of said second smartwatch, during performance of the second physiological activity by a second user of said second smartwatch.

A further feature or aspect of an exemplification is believed at the time of the filing of this patent application to possibly reside broadly in the smartwatch system, wherein: said first smartwatch is configured to permit tactile input to alter at least one parameter of how a first physiological activity, specific to a first user of said first smartwatch, is performed during performance of the first physiological activity by a first user of said first smartwatch; and said second smartwatch is configured to permit tactile input to alter at least one parameter of how a second physiological activity, specific to a second user of said second smartwatch, is performed during performance of the second physiological activity by a second user of said second smartwatch.

Another feature or aspect of an exemplification is believed at the time of the filing of this patent application to possibly reside broadly in the smartwatch system, wherein each of said first and second smartwatches is configured to permit tactile input of a request for assistance in the performance of a physiological activity.

Yet another feature or aspect of an exemplification is believed at the time of the filing of this patent application to possibly reside broadly in the smartwatch system, wherein: said first smartwatch is configured to permit tactile input to request information regarding how at least one parameter of a first physiological activity, specific to a first user of said first smartwatch, should be altered in response to information regarding current performance of the first physiological activity by a first user of said first smartwatch; said second smartwatch is configured to permit tactile input to request information regarding how at least one parameter of a second physiological activity, specific to a second user of said second smartwatch, should be altered in response to information regarding current performance of the second physiological activity by a second user of said second smartwatch; each of said first and second smartwatches is configured to wirelessly transfer performance information and request information to an external communication device for an automated or manual reply; and each of said first and second smartwatches is configured to automatically and wirelessly transmit data regarding performance of a physiological activity and/or status of a user to an external communication device.

Still another feature or aspect of an exemplification is believed at the time of the filing of this patent application to possibly reside broadly in the smartwatch system, wherein: said tracking arrangements of said first and second smartwatches are configured to permit tracking of the location of said first and second smartwatches in a building; and said tracking arrangements are configured to communicate with or be detected by tracking sensors to permit triangulation of the location of said smartwatches in a building.

A further feature or aspect of an exemplification is believed at the time of the filing of this patent application to possibly reside broadly in the smartwatch system, wherein: each of said first and second smartwatches comprises an image detection arrangement configured to detect images of objects; and said image detection arrangements are configured to detect images at different locations in a building to register the locations of said first and second smartwatches and/or retrieve information regarding physiological activities to be performed at the locations.

Another feature or aspect of an exemplification is believed at the time of the filing of this patent application to possibly reside broadly in the smartwatch system, wherein: each of said first and second smartwatches comprises a motion tracker configured to permit detection of angular movement from one point to another over a path of movement; and said first and second smartwatches are configured to capture angular movement data and transmit said angular movement data to an external communication device.

Yet another feature or aspect of an exemplification is believed at the time of the filing of this patent application to possibly reside broadly in the smartwatch system, wherein said first and second smartwatches are configured to transmit location and/or movement information as an alert to an external communication device upon location and/or movement information being outside desired parameters.

Still another feature or aspect of an exemplification is believed at the time of the filing of this patent application to possibly reside broadly in a method of using the smartwatch system, wherein said method comprises the steps of: displaying images and/or information on said first smartwatch relating to a first physiological activity specific to a first user of said first smartwatch; displaying images and/or information on said second smartwatch relating to a second physiological activity specific to a second user of said second smartwatch; and performing tactile input of commands and/or data by said first and second users relating to said first and second physiological activities via said touch screen interfaces of said first and second smartwatches.

The components disclosed in the patents, patent applications, patent publications, and other documents disclosed or incorporated by reference herein, may possibly be used in possible exemplifications of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one exemplification of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various exemplifications may be used with at least one exemplification or all of the exemplifications, if more than one exemplification is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible exemplification of the present application . . . " may possibly not be used or useable in any one or more exemplifications of the application.

The sentence immediately above relates to patents, patent applications, patent publications, and other documents either incorporated by reference or not incorporated by reference.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the exemplifications therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more exemplifications of the patents, patent applications, patent publications, and other documents, are not considered to be incorporated by reference herein for any of the patents, patent applications, patent publications, and other documents cited herein.

The description of the exemplification or exemplifications is believed, at the time of the filing of this patent application, to adequately describe the exemplification or exemplifications of this patent application. However, portions of the description of the exemplification or exemplifications may not be completely applicable to the claims as originally filed in this patent application, as amended during prosecution of this patent application, and as ultimately allowed in any patent issuing from this patent application. Therefore, any statements made relating to the exemplification or exemplifications are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the exemplification or exemplifications, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

The exemplifications of the invention described herein above in the context of the preferred exemplifications are not to be taken as limiting the exemplifications of the invention to all of the provided details thereof, since modifications and variations thereof may be made without departing from the spirit and scope of the exemplifications of the invention.

What is claimed is:

1. A smart device system comprising:
    a first smart device, said first smart device comprising:
        a device housing;
        a securing device configured to secure said device housing to a body portion of the user;
        a battery disposed in said device housing to supply power to said first smart device;
        an audio device disposed in said device housing and configured to emit sound and/or receive sound;
        a motion detection arrangement disposed in said device housing and configured to permit detection of the movement of said first smart device in at least one plane of movement;
        said motion detection arrangement comprising at least one of: motion sensors, gyroscopes, and accelerometers disposed in said device housing;
        a processor disposed in said device housing and configured to control operation of said first smart device;
        a memory disposed in said device housing and configured to store data, including information data specific to the physiological status and activity of a user;
        a wireless communication device disposed in said device housing and configured to wirelessly connect said first smart device to an external communication device;
        a display disposed on the front of said device housing and configured to display digital information and/or visual information comprising data and/or messages and/or images to the user; and
        said display comprising a touch screen interface to permit tactile input of commands and/or data by the user to execute different functions of said first smart device;
    a second smart device, said second smart device comprising:
        a device housing;
        a securing device configured to secure said device housing to a body portion of the user;
        a battery disposed in said device housing to supply power to said second smart device;
        an audio device disposed in said device housing and configured to emit sound and/or receive sound;
        a motion detection arrangement disposed in said device housing and configured to permit detection of the movement of said second smart device in at least one plane of movement;
        said motion detection arrangement comprising at least one of: motion sensors, gyroscopes, and accelerometers disposed in said device housing;
        a processor disposed in said device housing and configured to control operation of said second smart device;
        a memory disposed in said device housing and configured to store data, including information data specific to the physiological status and activity of a user;
        a wireless communication device disposed in said device housing and configured to wirelessly connect said second smart device to an external communication device;
        a display disposed on the front of said device housing and configured to display digital information and/or visual information comprising data and/or messages and/or images to the user; and
        said display comprising a touch screen interface to permit tactile input of commands and/or data by the user to execute different functions of said second smart device; and
    said first smart device being configured to display images and/or information relating to a first physiological activity specific to a first user of said first smart device, and said second smart device being configured to display images and/or information relating to a second physiological activity specific to a second user of said second smart device, wherein each of the first and second physiological activities comprises a physical therapy exercise to be performed by a patient;
    said first smart device being configured to record movement information of said first smart device upon performance of the first physiological activity, and said second smart device being configured to record movement information of said second smart device upon performance of the second physiological activity; and
    said first and second smart devices are configured to transmit actual movement information of the first and second physiological activities to a central computer to permit comparison of the actual movement information with predetermined movement information stored on the central computer, and to permit detection by a clinician of the actual movement information that does not correspond with the predetermined movement information.

2. The smart device system according to claim 1, wherein:
    said first smart device is configured to provide audio and/or video instruction to the first user of how to perform the first physiological activity; and
    said second smart device is configured to provide audio and/or video instruction to the second user of how to perform the second physiological activity.

3. The smart device system according to claim 2, wherein:
    said first smart device is configured to permit tactile input to permit the first user to record duration of the first physiological activity, or is configured to automatically sense and record duration of the first physiological activity;
    said second smart device is configured to permit tactile input to permit the second user to record duration of the second physiological activity, or is configured to automatically sense and record duration of the second physiological activity; and
    said wireless communication devices of said first and second smart devices are configured to wirelessly transmit the duration of the physiological activities to a central computer for storage.

4. The smart device system according to claim 3, wherein:
said first smart device is configured to display a first location in a physical therapy clinic where the first physiological activity is to be performed; and
said second smart device is configured to display a second location in the physical therapy clinic where the second physiological activity is to be performed.

5. The smart device system according to claim 4, wherein:
said first smart device is configured to wirelessly connect with an external communication device to permit determination of a location of the first smart device in the physical therapy clinic; and
said second smart device is configured to wirelessly connect with an external communication device to permit determination of a location of the second smart device in the physical therapy clinic.

6. The smart device system according to claim 5, wherein:
each of said first and second smart devices comprises a motion tracker configured to permit detection of angular movement from one point to another over a path of movement; and
said first and second smart devices are configured to capture angular movement data and wirelessly transmit said angular movement data to an external communication device.

7. The smart device system according to claim 6, wherein:
said first smart device is configured to display:
a description of a third physiological activity comprising a physical therapy exercise, different from the first physiological activity, to be performed by the first user of said first smart device upon completion of the first physiological activity, and
a third location where the third physiological activity is to be performed, which third location may be the same as or different from the first location; and
said second smart device is configured to display:
a description of a fourth physiological activity comprising a physical therapy exercise, different from the second physiological activity, to be performed by the second user of said second smart device upon completion of the second physiological activity, and
a fourth location where the fourth physiological activity is to be performed, which fourth location may be the same as or different from the second location.

8. The smart device system according to claim 7, wherein each of said first and second smart devices is configured to permit tactile input of a request for assistance from a patient to a clinician in the performance of at least one of the physiological activities.

9. The smart device system according to claim 8, wherein:
each of said first and second smart devices is configured to wirelessly receive alterations to at least one parameter of at least one of the physiological activities input by a clinician into an external communication device or a central computer; and
each of said first and second smart devices is configured to wirelessly transmit alterations to at least one parameter of at least one of the physiological activities input by a patient to an external communication device and/or a central computer.

10. The smart device system according to claim 1, wherein:
said first smart device is configured to permit tactile input to permit the first user to record duration of the first physiological activity, or is configured to automatically sense and record duration of the first physiological activity;
said second smart device is configured to permit tactile input to permit the second user to record duration of the second physiological activity, or is configured to automatically sense and record duration of the second physiological activity; and
said wireless communication devices of said first and second smart devices are configured to wirelessly transmit the duration of the physiological activities to a central computer for storage.

11. The smart device system according to claim 1, wherein:
each of said first and second smart devices comprises a motion tracker configured to permit detection of angular movement from one point to another over a path of movement; and
said first and second smart devices are configured to capture angular movement data and wirelessly transmit said angular movement data to an external communication device.

12. The smart device system according to claim 1, wherein:
said first smart device is configured to display:
a description of a third physiological activity comprising a physical therapy exercise, different from the first physiological activity, to be performed by the first user of said first smart device upon completion of the first physiological activity, and
a third location where the third physiological activity is to be performed, which third location may be the same as or different from the first location; and
said second smart device is configured to display:
a description of a fourth physiological activity comprising a physical therapy exercise, different from the second physiological activity, to be performed by the second user of said second smart device upon completion of the second physiological activity, and
a fourth location where the fourth physiological activity is to be performed, which fourth location may be the same as or different from the second location.

13. A method of using a smart device system according to claim 1, wherein said method comprises the steps of:
displaying images and/or information on said first smartwatch relating to a first physiological activity specific to a first user of said first smartwatch, wherein said first physiological activity comprises a physical therapy exercise to be performed by a patient;
displaying images and/or information on said second smartwatch relating to how to perform a second physiological activity specific to a second user of said second smartwatch, wherein said second physiological activity comprises a physical therapy exercise to be performed by a patient;
performing said first and second physiological activities;
recording movement information of said first smart device;
recording movement information of said second smart device;
transmitting actual movement information of the first and second physiological activities to a central computer; and
comparing the actual movement information with predetermined movement information stored on the central computer to permit detection by a clinician of the actual movement information that does not correspond with the predetermined movement information.

14. The method according to claim 13, wherein said method comprises the steps of:

providing audio and/or video instruction via said first smart device to the first user of how to perform the first physiological activity; and providing audio and/or video instruction via said second smart device to the second user of how to perform the second physiological activity.

15. A smart device system comprising:

a first smart device, said first smart device comprising:
  a device housing;
  a securing device configured to secure said device housing to a body portion of the user;
  a battery disposed in said device housing to supply power to said first smart device;
  an audio device disposed in said device housing and configured to emit sound and/or receive sound;
  a motion detection arrangement disposed in said device housing and configured to permit detection of the movement of said first smart device in at least one plane of movement;
  said motion detection arrangement comprising at least one of: motion sensors, gyroscopes, and accelerometers disposed in said device housing;
  a processor disposed in said device housing and configured to control operation of said first smart device;
  a memory disposed in said device housing and configured to store data, including information data specific to the physiological status and activity of a user;
  a wireless communication device disposed in said device housing and configured to wirelessly connect said first smart device to an external communication device;
  a display disposed on the front of said device housing and configured to display digital information and/or visual information comprising data and/or messages and/or images to the user; and
  said display comprising a touch screen interface to permit tactile input of commands and/or data by the user to execute different functions of said first smart device;

a second smart device, said second smart device comprising:
  a device housing;
  a securing device configured to secure said device housing to a body portion of the user;
  a battery disposed in said device housing to supply power to said second smart device;
  an audio device disposed in said device housing and configured to emit sound and/or receive sound;
  a motion detection arrangement disposed in said device housing and configured to permit detection of the movement of said second smart device in at least one plane of movement;
  said motion detection arrangement comprising at least one of: motion sensors, gyroscopes, and accelerometers disposed in said device housing;
  a processor disposed in said device housing and configured to control operation of said second smart device;
  a memory disposed in said device housing and configured to store data, including information data specific to the physiological status and activity of a user;
  a wireless communication device disposed in said device housing and configured to wirelessly connect said second smart device to an external communication device;
  a display disposed on the front of said device housing and configured to display digital information and/or visual information comprising data and/or messages and/or images to the user; and
  said display comprising a touch screen interface to permit tactile input of commands and/or data by the user to execute different functions of said second smart device; and said first smart device being configured to display images and/or information relating to a first physiological activity specific to a first user of said first smart device, and said second smart device being configured to display images and/or information relating to a second physiological activity specific to a second user of said second smart device, wherein each of the first and second physiological activities comprises a physical therapy exercise to be performed by a patient;

said first smart device being configured to record movement information of said first smart device upon performance of the first physiological activity, and said second smart device being configured to record movement information of said second smart device upon performance of the second physiological activity;

said first smart device is configured to display a first location in a physical therapy clinic where the first physiological activity is to be performed; and said second smart device is configured to display a second location in the physical therapy clinic where the second physiological activity is to be performed.

16. A smart device system comprising:

a first smart device, said first smart device comprising:
  a device housing;
  a securing device configured to secure said device housing to a body portion of the user;
  a battery disposed in said device housing to supply power to said first smart device;
  an audio device disposed in said device housing and configured to emit sound and/or receive sound;
  a motion detection arrangement disposed in said device housing and configured to permit detection of the movement of said first smart device in at least one plane of movement;
  said motion detection arrangement comprising at least one of: motion sensors, gyroscopes, and accelerometers disposed in said device housing;
  a processor disposed in said device housing and configured to control operation of said first smart device;
  a memory disposed in said device housing and configured to store data, including information data specific to the physiological status and activity of a user;
  a wireless communication device disposed in said device housing and configured to wirelessly connect said first smart device to an external communication device;
  a display disposed on the front of said device housing and configured to display digital information and/or visual information comprising data and/or messages and/or images to the user; and
  said display comprising a touch screen interface to permit tactile input of commands and/or data by the user to execute different functions of said first smart device;

a second smart device, said second smart device comprising:
  a device housing;
  a securing device configured to secure said device housing to a body portion of the user;
  a battery disposed in said device housing to supply power to said second smart device;

an audio device disposed in said device housing and configured to emit sound and/or receive sound;

a motion detection arrangement disposed in said device housing and configured to permit detection of the movement of said second smart device in at least one plane of movement;

said motion detection arrangement comprising at least one of: motion sensors, gyroscopes, and accelerometers disposed in said device housing;

a processor disposed in said device housing and configured to control operation of said second smart device;

a memory disposed in said device housing and configured to store data, including information data specific to the physiological status and activity of a user;

a wireless communication device disposed in said device housing and configured to wirelessly connect said second smart device to an external communication device;

a display disposed on the front of said device housing and configured to display digital information and/or visual information comprising data and/or messages and/or images to the user; and said display comprising a touch screen interface to permit tactile input of commands and/or data by the user to execute different functions of said second smart device; and said first smart device being configured to display images and/or information relating to a first physiological activity specific to a first user of said first smart device, and said second smart device being configured to display images and/or information relating to a second physiological activity specific to a second user of said second smart device, wherein each of the first and second physiological activities comprises a physical therapy exercise to be performed by a patient;

said first smart device being configured to record movement information of said first smart device upon performance of the first physiological activity, and said second smart device being configured to record movement information of said second smart device upon performance of the second physiological activity;

said first smart device is configured to wirelessly connect with an external communication device to permit determination of a location of the first smart device in the physical therapy clinic; and said second smart device is configured to wirelessly connect with an external communication device to permit determination of a location of the second smart device in the physical therapy clinic.

* * * * *